(12) United States Patent
Mader et al.

(10) Patent No.: US 10,208,310 B2
(45) Date of Patent: Feb. 19, 2019

(54) ANTI-TNF COMPOUNDS

(71) Applicant: Exicure, Inc., Skokie, IL (US)

(72) Inventors: Christopher C. Mader, Cambridge, MA (US); Tiffany L. Halo, Cambridge, MA (US); Sergei Gryaznov, San Mateo, CA (US); Richard Kang, Wilmette, IL (US); Weston Daniel, Evanston, IL (US)

(73) Assignee: Exicure, Inc., Skokie, IL (US)

( * ) Notice: Subject to any disclaimer, the term of this patent is extended or adjusted under 35 U.S.C. 154(b) by 0 days.

(21) Appl. No.: 15/517,064

(22) PCT Filed: Oct. 6, 2015

(86) PCT No.: PCT/US2015/054288
§ 371 (c)(1),
(2) Date: Apr. 5, 2017

(87) PCT Pub. No.: WO2016/057549
PCT Pub. Date: Apr. 14, 2016

(65) Prior Publication Data
US 2017/0306331 A1    Oct. 26, 2017

Related U.S. Application Data

(60) Provisional application No. 62/060,424, filed on Oct. 6, 2014.

(51) Int. Cl.
| | |
|---|---|
| *C07H 21/04* | (2006.01) |
| *C12N 15/113* | (2010.01) |
| *A61K 31/712* | (2006.01) |
| *A61K 31/7125* | (2006.01) |
| *C07H 21/02* | (2006.01) |
| *C07H 21/00* | (2006.01) |
| *A61K 47/48* | (2006.01) |
| *A61K 45/06* | (2006.01) |
| *B82Y 5/00* | (2011.01) |

(52) U.S. Cl.
CPC ........ *C12N 15/1136* (2013.01); *A61K 31/712* (2013.01); *A61K 31/7125* (2013.01); *A61K 45/06* (2013.01); *A61K 47/48046* (2013.01); *A61K 47/48815* (2013.01); *C07H 21/00* (2013.01); *C07H 21/02* (2013.01); *C07H 21/04* (2013.01); *B82Y 5/00* (2013.01); *C12N 2310/11* (2013.01); *C12N 2310/315* (2013.01); *C12N 2310/321* (2013.01); *C12N 2310/341* (2013.01); *C12N 2310/346* (2013.01); *C12N 2310/351* (2013.01); *C12N 2310/3515* (2013.01); *C12N 2310/3517* (2013.01); *C12N 2320/32* (2013.01)

(58) Field of Classification Search
None
See application file for complete search history.

(56) References Cited

U.S. PATENT DOCUMENTS

| | | |
|---|---|---|
| 5,264,618 A | 11/1993 | Felgner et al. |
| 5,472,881 A | 12/1995 | Beebe et al. |
| 5,814,666 A | 9/1998 | Green et al. |
| 5,955,589 A | 9/1999 | Cook et al. |
| 6,051,698 A | 4/2000 | Janjic et al. |
| 6,194,388 B1 | 2/2001 | Krieg et al. |
| 6,207,646 B1 | 3/2001 | Krieg et al. |
| 6,239,116 B1 | 5/2001 | Krieg et al. |
| 6,361,944 B1 | 3/2002 | Mirkin et al. |
| 6,406,705 B1 | 6/2002 | Davis et al. |
| 6,506,564 B1 | 1/2003 | Mirkin et al. |
| 6,677,153 B2 | 1/2004 | Iversen |
| 7,833,992 B2 | 11/2010 | Vargeese et al. |
| 8,323,686 B2 | 12/2012 | Mirkin et al. |
| 8,933,046 B2 | 1/2015 | Machuy et al. |
| 9,216,155 B2 | 12/2015 | Thaxton et al. |
| 9,532,948 B2 | 1/2017 | Mirkin et al. |
| 9,693,957 B2 | 7/2017 | Lin et al. |
| 2002/0172711 A1 | 11/2002 | Martin et al. |
| 2003/0044354 A1 | 3/2003 | Carpenter et al. |
| 2003/0147966 A1 | 8/2003 | Franzen et al. |
| 2003/0170162 A1 | 9/2003 | Nayfeh et al. |
| 2004/0033197 A1 | 2/2004 | Madar et al. |
| 2004/0038891 A1 | 2/2004 | Bisgaier et al. |
| 2004/0053384 A1 | 3/2004 | Sligar et al. |
| 2004/0158051 A1 | 8/2004 | Ozkan et al. |
| 2004/0170560 A1 | 9/2004 | Fossheim et al. |
| 2005/0130167 A1 | 6/2005 | Bao et al. |
| 2006/0014191 A1 | 1/2006 | Lao et al. |
| 2006/0083781 A1 | 4/2006 | Shastri et al. |
| 2006/0292174 A1 | 12/2006 | De Los Rios et al. |
| 2007/0243136 A1 | 10/2007 | Fisher et al. |

(Continued)

FOREIGN PATENT DOCUMENTS

| | | |
|---|---|---|
| CN | 1474831 A | 2/2004 |
| CN | 102036652 A | 4/2011 |

(Continued)

OTHER PUBLICATIONS

Acton et al., Identification of scavenger receptor SR-BI as a high density lipoprotein receptor. Science. Jan. 26, 1996;271(5248):518-20.

(Continued)

*Primary Examiner* — Kimberly Chong

(74) *Attorney, Agent, or Firm* — Wolf, Greenfield & Sacks, P.C.

(57) ABSTRACT

TNFα antisense oligonucleotides are provided herein. Methods of treating TNFα diseases or disorders using the TNFα antisense oligonucleotides and related products are provided.

42 Claims, 16 Drawing Sheets

Specification includes a Sequence Listing.

(56) References Cited

U.S. PATENT DOCUMENTS

| | | |
|---|---|---|
| 2007/0249555 A1 | 10/2007 | Barbaras et al. |
| 2007/0298257 A1 | 12/2007 | Ludwig et al. |
| 2008/0175893 A1 | 7/2008 | Huang |
| 2008/0194463 A1 | 8/2008 | Weller et al. |
| 2008/0274454 A1 | 11/2008 | Mirkin et al. |
| 2008/0306016 A1 | 12/2008 | Mirkin et al. |
| 2008/0311182 A1 | 12/2008 | Ferrari et al. |
| 2009/0018028 A1 | 1/2009 | Lindsay et al. |
| 2009/0053169 A1 | 2/2009 | Castillo et al. |
| 2009/0209629 A1 | 8/2009 | Mirkin et al. |
| 2009/0317802 A1 | 12/2009 | Bhatia et al. |
| 2009/0322327 A1 | 12/2009 | Gao |
| 2009/0324706 A1 | 12/2009 | Mirkin et al. |
| 2010/0136682 A1 | 6/2010 | Mirkin et al. |
| 2010/0184844 A1 | 7/2010 | Mirkin et al. |
| 2010/0233141 A1 | 9/2010 | Polach et al. |
| 2010/0233270 A1 | 9/2010 | Mirkin et al. |
| 2011/0020242 A1 | 1/2011 | Zheng et al. |
| 2011/0052680 A1 | 3/2011 | Hendrickson |
| 2011/0052697 A1 | 3/2011 | Farokhzad et al. |
| 2011/0059156 A9 | 3/2011 | Mirkin et al. |
| 2011/0111974 A1 | 5/2011 | Mirkin et al. |
| 2012/0149843 A1 | 6/2012 | Chien et al. |
| 2012/0244230 A1 | 9/2012 | Mirkin et al. |
| 2013/0034599 A1 | 2/2013 | Thaxton et al. |
| 2013/0089614 A1 | 4/2013 | Zhang et al. |
| 2013/0101512 A1 | 4/2013 | Mirkin et al. |
| 2013/0149374 A1 | 6/2013 | Lee et al. |
| 2013/0195759 A1 | 8/2013 | Mirkin et al. |
| 2013/0196951 A1 | 8/2013 | Schoenfisch et al. |
| 2013/0295129 A1 | 11/2013 | Irvine et al. |
| 2014/0005258 A1 | 1/2014 | Mirkin et al. |
| 2014/0065425 A1 | 3/2014 | Bogdanov |
| 2014/0134658 A1 | 5/2014 | Ahrens et al. |
| 2014/0294927 A1 | 10/2014 | Thaxton et al. |
| 2015/0064255 A1 | 3/2015 | Thaxton et al. |
| 2015/0086985 A1 | 3/2015 | Giljohann et al. |
| 2015/0111790 A1 | 4/2015 | Ategeka et al. |
| 2016/0184226 A1 | 6/2016 | Thaxton et al. |
| 2016/0186178 A1 | 6/2016 | Radovic-Moreno et al. |
| 2016/0193361 A1 | 7/2016 | Thaxton et al. |
| 2016/0194642 A1 | 7/2016 | Gryaznov et al. |
| 2016/0274134 A1 | 9/2016 | Mutharasan et al. |
| 2016/0310425 A1 | 10/2016 | Mirkin et al. |
| 2017/0157048 A1 | 6/2017 | Radovic-Moreno et al. |
| 2017/0175121 A1 | 6/2017 | Gryaznov |
| 2017/0240960 A1 | 8/2017 | Giljohann et al. |
| 2017/0306331 A1 | 10/2017 | Mader et al. |
| 2017/0312365 A1 | 11/2017 | Thaxton et al. |
| 2017/0354711 A1 | 12/2017 | Thaxton et al. |
| 2018/0042848 A1 | 2/2018 | Gryaznov et al. |

FOREIGN PATENT DOCUMENTS

| | | |
|---|---|---|
| CN | 102165061 | 8/2011 |
| EP | 1889911 A2 | 2/2008 |
| EP | 2399608 A1 | 12/2011 |
| EP | 2656858 A1 | 10/2013 |
| JP | 2011-507807 | 3/2011 |
| JP | 2011-518826 | 6/2011 |
| KR | 20110039798 A | 4/2011 |
| WO | WO 1992/021330 | 12/1992 |
| WO | WO 1993/021528 A1 | 10/1993 |
| WO | WO 1995/034289 A1 | 12/1995 |
| WO | WO 1997/048715 A1 | 12/1997 |
| WO | WO 1998/004740 A1 | 2/1998 |
| WO | WO 2000/020645 | 4/2000 |
| WO | WO 2001/003709 A1 | 1/2001 |
| WO | WO 2003/008539 A2 | 1/2003 |
| WO | WO 2005/063201 A2 | 7/2005 |
| WO | WO 2005/063288 A1 | 7/2005 |
| WO | WO 2006/110350 A2 | 10/2006 |
| WO | WO 2006/110350 A3 | 10/2006 |
| WO | WO 2006/128121 A2 | 11/2006 |
| WO | WO 2006/138145 A1 | 12/2006 |
| WO | WO 2007/008463 A2 | 1/2007 |
| WO | WO 2007/089607 A2 | 8/2007 |
| WO | WO 2007/106683 A2 | 9/2007 |
| WO | WO 2008/014979 A2 | 2/2008 |
| WO | WO 2008/106660 A2 | 9/2008 |
| WO | WO 2008/127789 A2 | 10/2008 |
| WO | WO 2009/012786 A2 | 1/2009 |
| WO | WO 2009/051451 A2 | 4/2009 |
| WO | WO 2009/061515 A1 | 5/2009 |
| WO | WO 2009/073984 A1 | 6/2009 |
| WO | WO 2009/105260 | 8/2009 |
| WO | WO 2009/131704 | 10/2009 |
| WO | WO 2009/131931 A1 | 10/2009 |
| WO | WO 2010/017152 | 2/2010 |
| WO | WO 2010/017154 | 2/2010 |
| WO | WO 2010/085959 A1 | 8/2010 |
| WO | WO 2010/120420 | 10/2010 |
| WO | WO 2011/017456 A2 | 2/2011 |
| WO | WO 2011/017690 A2 | 2/2011 |
| WO | WO 2011/053940 A2 | 5/2011 |
| WO | WO 2011/072133 A1 | 6/2011 |
| WO | WO 2011/079290 A1 | 6/2011 |
| WO | WO 2011/091065 A2 | 7/2011 |
| WO | WO 2011/113054 A2 | 9/2011 |
| WO | WO 2012/022948 A1 | 2/2012 |
| WO | WO 2012/055933 A1 | 5/2012 |
| WO | WO 2012/068470 A2 | 5/2012 |
| WO | WO 2012/097177 | 7/2012 |
| WO | WO 2013/012628 A2 | 1/2013 |
| WO | WO 2013/151771 A1 | 10/2013 |
| WO | WO 2014/025795 A1 | 2/2014 |
| WO | WO 2014/052188 A1 | 4/2014 |
| WO | WO 2014/169264 A2 | 10/2014 |
| WO | WO 2015/013673 | 1/2015 |
| WO | WO 2015/013675 | 1/2015 |
| WO | WO 2015/153975 A1 | 10/2015 |
| WO | WO 2015/187966 A1 | 12/2015 |
| WO | WO 2015/195628 A2 | 12/2015 |
| WO | WO 2016/057549 A1 | 4/2016 |
| WO | WO 2016/115320 A1 | 7/2016 |
| WO | WO 2017/035278 A1 | 3/2017 |

OTHER PUBLICATIONS

Akhter et al., Gold nanoparticles in theranostic oncology: current state-of-the-art. Expert Opin Drug Deliv. Oct. 2012;9(10):1225-43. Epub Aug. 16, 2012.

Ali et al., Vaccines Combined with Immune Checkpoint Antibodies Promote Cytotoxic T-cell Activity and Tumor Eradication. Cancer Immunol Res. Feb. 2016;4(2):95-100. doi: 10.1158/2326-6066.CIR-14/0126. Epub Dec. 15, 2015.

Asthana et al., Mannosylated chitosan nanoparticles for delivery of antisense oligonucleotides for macrophage targeting. Biomed Res Int. 2014;2014:526391. doi: 10.1155/2014/526391. Epub Jun. 26, 2014.

Aurasense Therapeutics, NIH grant, Topically-delivered Target Gene Suppression of Immune Activation in Psoriasis—David Giljohann, Accessed on Aug. 2, 2017 from http://grantome.com/grant/NIH/R41-AR066438-01. Accessible online on Feb. 21, 2016 as verified through Wayback Machine.

Bae et al., Targeted drug delivery to tumors: myths, reality and possibility. J Control Release. Aug. 10, 2011;153(3):198-205. doi: 10.1016/j.jconrel.2011.06.001. Epub Jun. 6, 2011.

Banchelli, M. et al., Phospholipid Membranes Decorated by Cholesterol-Based Oligonucleotides as Soft Hybrid Nanostructures, J. Phys. Chem., 2008, 112 (35), 10942-10952.

Banga et al., Liposomal spherical nucleic acids. J Am Chem Soc. Jul. 16, 2014;136(28):9866-9. doi: 10.1021/ja504845f. Epub Jul. 1, 2014.

Barrat et al., Nucleic acids of mammalian origin can act as endogenous ligands for Toll-like receptors and may promote systemic lupus erythematosus. J Exp Med. Oct. 17, 2005;202(8):1131-9.

Bhattarai et al., Enhanced Gene and siRNA Delivery by Polycation-Modified Mesoporous Silica Nanoparticles Loaded with Chloroquine, Pharm. Res., 2010, 27, 2556-2568.

(56) References Cited

OTHER PUBLICATIONS

Boudreault et al., Nanoscale tools to selectively destroy cancer cells. Chem Commun. May 14, 2008;(18):2118-20. doi: 10.1039/b800528a. Epub Apr. 7, 2008.

Chen et al., Kinetics and thermodynamics of DNA hybridization on gold nanoparticles. Nucleic Acids Res. Jun. 2009;37(11):3756-65. doi: 10.1093/nar/gkp230. Epub Apr. 20, 2009.

Cheng et al., Interdigitated phospholipid/alkanethiol bilayers assembled on APTMS-supported gold colloid electrodes. Electroanalysis. 2004;16(1-2): 127-31. doi:10.1002/elan.200302929.

Cheng et al., Tandem synthesis of core-shell brush copolymers and their transformation to peripherally cross-linked and hollowed nanostructures. J Am Chem Soc. May 31, 2006;128(21):6808-9. Published on web May 6, 2006.

Chinnathambi et al., Binding mode of CpG Oligodeoxynucleotides to nanoparticles regulates bifurcated cytokine induction via Toll-like Receptor 9. Sci Reports. 2012;2:1-9.

Cho et al., Targeted delivery of siRNA-generating DNA nanocassettes using multifunctional nanoparticles. Small. Jun. 10, 2013;9(11):1964-73. doi: 10.1002/smll.201201973. Epub Jan. 6, 2013.

Cho et al., Therapeutic nanoparticles for drug delivery in cancer. Clin Cancer Res. Mar. 1, 2008;14(5):1310-6. doi: 10.1158/1078-0432.CCR-07-1441.

Cormode, D.P. et al., Nanocrystal Core High-Density Lipoproteins: A Multimodality Contrast Agent Platform, Nano Lett., 2008, 8 (11), 3715-3723.

Cutler et al., Polyvalent nucleic acid nanostructures. J Am Chem Soc. Jun. 22, 2011;133(24):9254-7. doi:10.1021/ja203375n. Epub Jun. 1, 2011.

Cutler et al., Polyvalent oligonucleotide iron oxide nanoparticle click conjugates. Nano Lett. Apr. 14, 2010;10(4):1477-80. doi:10.1021/n1100477m.

Cutler et al., Spherical nucleic acids. J Am Chem Soc. Jan. 25, 2012;134(3):1376-91. doi: 10.1021/ja209351u. Epub Jan. 9, 2012.

Daniel et al., Gold nanoparticles: assembly, supramolecular chemistry, quantum-size-related properties, and applications toward biology, catalysis, and nanotechnology. Chem Rev. Jan. 2004;104(1):293-346.

Dave et al., Programmable assembly of DNA-functionalized liposomes by DNA. ACS Nano. Feb. 22, 2011;5(2):1304-12. doi: 10.1021/nn1030093. Epub Jan. 4, 2011.

Dhar et al., Polyvalent oligonucleotide gold nanoparticle conjugates as delivery vehicles for platinum (IV) warheads. J Am Chem Soc. Oct. 21, 2009;131(41):14652-3. doi: 10.1021/ja907182.

Dikmen et al., Targeting critical steps of cancer metastasis and recurrence using telomerase template antagonists. Biochim Biophys Acta. Apr. 2009;1792(4):240-7. doi: 10.1016/j.bbadis.2009.01.018. Epub Feb. 9, 2009.

Elbakry et al., Layer-by-Layer Assembled Gold Nanoparticles for siRNA Delivery, Nano Lett., 2009, 9 (5), 2059-2064.

Fan et al., Self-Assembly of Ordered, Robust, Three-Dimensional Gold Nanocrystal/Silica Arrays, Science, 2004, 403, 567-571.

Ferrari, Cancer nanotechnology: opportunities and challenges. Nature Reviews Cancer. 2005;5: 161-71.

Frias, J. C. et al., Properties of a Versatile Nanoparticle Platform Contrast Agent to Image and Characterize Atherosclerotic Plaques by Magnetic Resonance Imaging, Nano Lett., 2006, 6 (10), 2220-2224.

Giljohann et al., Gene regulation with polyvalent siRNA-nanoparticle conjugates. J Am Chem Soc. Feb. 18, 2009;131(6):2072-3.

Giljohann et al., Gold nanoparticles for biology and medicine. Angew Chem Int Ed Engl. Apr. 26, 2010;49(19):3280-94. doi: 10.1002/anie.200904359.

Giljohann et al., Oligonucleotide loading determines cellular uptake of DNA-modified gold nanoparticles. Nano Lett. Dec. 2007;7(12):3818-21. Epub Nov. 13, 2007.

Gissot et al., Nucleoside, nucleotide and oligonucleotide based amphiphiles: a successful marriage of nucleic acids with lipids. Org. Biomol. Chem. 2008;6:1324-33.

Godard, G. et al., Antisense Effects of Cholesterol-Oligodeoxynucleotide Conjugates Associated with Poly(alkylcyanoacrylate) Nanoparticles, Eur. J. Biochem., 1995, 232 (2), 404-410.

Grijalvo et al., Oligonucleotide delivery: a patent review (2010-2013). Expert Opin Ther Pat. Jul. 2014;24(7):801-19. doi:10.1517/13543776.2014.915944. Epub May 5, 2014.

Gryaznov, Oligonucleotide n3'→p5' phosphoramidates and thiophoshoramidates as potential therapeutic agents. Chem Biodivers. Mar. 2010;7(3):477-93. doi: 10.1002/cbdv.200900187. Review.

Gursel et al., Repetitive elements in mammalian telomeres suppress bacterial DNA-induced immune activation. J Immunol. Aug. 1, 2003;171(3):1393-400.

Han et al., Drug and gene delivery using gold nanoparticles. NanoBiotechnology. Mar. 2007;3(1):40-5.

Hashmi et al., Gold catalysis. Angew Chem Int Ed Engl. Dec. 4, 2006;45(47):7896-936.

Hashmi, Gold-catalyzed organic reactions. Chem Rev. Jul. 2007;107(7):3180-211. Epub Jun. 20, 2007.

He et al., Phospholipid-stabilized Au-nanoparticles. Biomacromolecules. May-Jun. 2005;6(3):1224-5.

Houot et al., T-cell modulation combined with intratumoral CpG cures lymphoma in a mouse model without the need for chemotherapy. Blood. Apr. 9, 2009;113(15):3546-52. doi: 10.1182/blood-2008-07-170274. Epub Oct. 21, 2008.

Hurst, S. et al., Maximizing DNA Loading on a Range of Gold Nanoparticle Sizes, Anal. Chem., 2006, 78 (24), 8313-8318.

Jayawickramarajah et al., Allosteric control of self-assembly: modulating the formation of guanine quadruplexes through orthogonal aromatic interactions. Angew Chem Int Ed Engl. 2007;46(40):7583-6.

Jones, Simultaneous labeling of lipoprotein intracellular trafficking in pigeon monocyte-derived macrophages. Am J Pathol. Mar. 1997;150(3):1113-24.

Kandimalla et al., Secondary structures in CpG oligonucleotides affect immunostimulatory activity. Biochem Biophys Res Commun. Jul. 11, 2003;306(4):948-53.

Kerkmann et al., Immunostimulatory properties of CpG-oligonucleotides are enhanced by the use of protamine nanoparticles. Oligonucleotides. 2006 Winter;16(4):313-22.

Khmelinskaia et al., Effect of anchor positioning on binding and diffusion of elongated 3D DNA nanostructures on lipid membranes. J. Phys. D: Appl Phys. Apr. 13, 2016;49(19):194001.

Kim et al., Cationic solid lipid nanoparticles reconstituted from low density lipoprotein components for delivery of siRNA. Mol Pharm. Jul.-Aug. 2008;5(4):622-31. doi: 10.1021/mp8000233. Epub May 8, 2008.

Kim, S. et al., Systemic and Specific Delivery of Small Interfering RNAs to the Liver Mediated by Apolipoprotein A-I, Mol. Ther., 2007, 15 (6), 1145-1152.

Kong et al., Cationic lipid-coated gold nanoparticles as efficient and non-cytotoxic intracellular siRNA delivery vehicles. Pharm Res. Feb. 2012;29(2):362-74. doi: 10.1007/s11095-011-0554-y. Epub Aug. 13, 2011.

Kwoh et al., Stabilization of poly-L-lysine/DNA polyplexes for in vivo gene delivery to the liver. Biochim Biophys Acta. Feb. 16, 1999;1444(2):171-90.

Leander, D., Mixed-Monolayer Gold Nanoparticles for Cancer Therapeutics, Nanoscape, 2010, 7 (1), 11-14.

Lee et al., All-in-one target-cell-specific magnetic nanoparticles for simultaneous molecular imaging and siRNA delivery. Angew Chem Int Ed Engl. 2009;48(23):4174-9. doi:10.1002/anie.200805998.

Lee et al., Imageable antigen-presenting gold nanoparticle vaccines for effective cancer immunotherapy in vivo. Angew Chem Int Ed Engl. Aug. 27, 2012;51(35):8800-5. doi: 10.1002/anie.201203193.

Lenert et al., Inhibitory oligonucleotides block the induction of AP-1 transcription factor by stimulatory CpG oligonucleotides in B cells. Antisense Nucleic Acid Drug Dev. 2003;13(3):143-50.

Lennox et al., Characterization of modified antisense oligonucleotides in Xenopus laevis embryos. Oligonucleotides. 2006 Spring;16(1):26-42.

(56) References Cited

OTHER PUBLICATIONS

Lewandowski et al., Topically delivered spherical nucleic acid nanoconjugates targeting TNF improve the psoriatic phenotype. J Invest Dermatol. 2015 135:S71. Abstract 413.

Li et al., Combination delivery of antigens and CpG by lanthanides-based core-shell nanoparticles for enhanced immune response and dual-mode imaging. Adv Healthc Mater. Oct. 2013;2(10):1309-13. doi:10.1002/adhm.201200364. Epub Mar. 25, 2013.

Li et al., Nanofabrication by DNA self-assembly. Materials Today. Elsevier Science. May 1, 2009;12(5)24-32.

Lin et al., Gold nanoparticle delivery of modified CpG stimulates macrophages and inhibits tumor growth for enhanced immunotherapy. PLoS One. May 15, 2013;8(5):e63550. doi: 10.1371/journal.pone. 0063550. Print 2013.

Liu et al., Membrane anchored immunostimulatory oligonucleotides for in vivo cell modification and localized immunotherapy. Angew Chem Int Ed Engl. Jul. 25, 2011;50(31):7052-5. doi: 10.1002/anie.201101266. Epub Jun. 17, 2011.

Liu et al., Structure-based programming of lymph-node targeting in molecular vaccines. Nature. Mar. 27, 2014;507(7493):519-22. doi: 10.1038/nature12978.

Liu, J. et al., Silica Nanoparticle Supported Lipid Bilayers for Gene Delivery, Chem. Commun., 2009, 5100-5102.

Luthi et al., Nanotechnology for synthetic high-density lipoproteins. Trens Mol Med. Dec. 2010;16(12):553-60. doi: 10.1016/j.molmed. 2010.10.006. Epub Nov. 17, 2010.

Lytton-Jean et al., A thermodynamic investigation into the binding properties of DNA functionalized gold nanoparticle probes and molecular fluorophore probes. J Am Chem Soc. Sep. 21, 2005;127(37):12754-5.

Major, M. et al., Characterisation and Phase Behaviour of Phospholipid Bilayers Adsorbed on Spherical Polysaccharidic Nanoparticles, Biochimica et Biophysica Acta, 1997, 1327, 32-40.

Mangsbo et al., Enhanced tumor eradication by combining CTLA-4 or PD-1 blockade with CpG therapy. J Immunother. Apr. 2010;33(3):225-35. doi: 10.1097/CJI.0b013e3181c01fcb.

Marquele-Oliveira et al., Development of nitrosyl ruthenium complex-loaded lipid carriers for topical administration: improvement in skin stability and in nitric oxide release by visible light irradiation. J Pharm Biomed Anal. Dec. 1, 2010;53(4):843-51. doi: 10.1016/j.jpba.2010.06.007. Epub Jun. 19, 2010.

Massich et al., Regulating immune response using polyvalent nucleic acid-gold nanoparticle conjugates. Mol Pharm. Nov.-Dec. 2009;6(6):1934-40.

Matsunaga, T. et al., Biomagnetic Nanoparticle Formation and Application, Supramolecular Science, 1998, 5 (3-4), 391-394.

McBain, S. et al., Polyethyleneimine Functionalized Iron Oxide Nanoparticles as Agents for DNA Deliver and Transfection, J. Mater. Chem., 2007, 17, 2561-2565.

McKay et al., Characterization of a potent and specific class of antisense oligonucleotide inhibitor of human protein kinase C-alpha expression. J Biol Chem. Jan. 15, 1999;274(3):1715-22.

McMahon et al., Biomimetic high density lipoprotein nanoparticles for nucleic acid delivery. Nano Lett. Mar. 9, 2011;11(3):1208-14. doi: 10.1021/nl1041947. Epub Feb. 14, 2011.

Medintz et al., A reactive peptidic linker for self-assembling hybrid quantum dot-DNA bioconjugates. Nano Lett. Jun. 2007;7(6):1741-8. Epub May 26, 2007.

Mirza et al., Preparation and characterization of doxorubicin functionalized gold nanoparticles. Eur J Med Chem. May 2011;46(5):1857-60. doi: 10.1016/j.ejmech.2011.02.048. Epub Feb. 24, 2011.

Mohamed et al., Effect of toll-like receptor 7 and 9 targeted therapy to prevent the development of hepatocellular carcinoma. Liver Int. Mar. 2015;35(3):1063-76. doi: 10.1111/liv.12626. Epub Jul. 30, 2014.

Monia et al., Nuclease resistance and antisense activity of modified oligonucleotides targeted to Ha-ras. J Biol Chem. Jun. 14, 1996;271(24):14533-40.

Nam et al., Nanoparticle-based bio-bar codes for the ultrasensitive detection of proteins. Science. Sep. 26, 2003;301(5641):1884-6.

Niemeyer, C. et al., Bifunctional DNA-Gold Nanoparticle Conjugates as Building Blocks for the Self-Assembly of Cross-Linked Particle Layers, Biochemical and Biophysical Research Communications, 2003, 311 (4), 995-999.

Nikolov et al., Bias-dependent admittance in hybrid bilayer membranes. Langmuir. Aug. 15, 2006;22(17):7156-8.

Pan et al., Dendrimer-Modified Magnetic Nanoparticles Enhance Efficiency of Gene Delivery System. Cancer Res. 2007;67:8156-8163.

Patel et al., Peptide antisense nanoparticles. Proc Natl Acad Sci U S A. Nov. 11, 2008;105(45):17222-6. doi: 10.1073/pnas. 0801609105.

Patil et al., Evidence for Novel Interdigitated Bilayer Formation of Fatty Acids During Three-Dimensional Self-Assembly on Silver Colloidal Particles, J. Am. Chem. Soc., 1997, 119 (39), 9281-9282.

Patwa et al., Hybrid lipid oligonucleotide conjugates: synthesis, self-assemblies and biomedical applications. Chem Soc Rev. 2011;40:5844-54.

Paul, New Way to Kill Lymphoma without Chemotherapy uses Golden Nanoparticles. Feinberg School of Medicine: Northwestern University. Jan. 22, 2013. 4 pages. ww.feinberg.northwestern.edu/news/2013/01/lymphoma_nanoparticales.html.

Peter et al., Characterization of suppressive oligodeoxynucleotides that inhibit Toll-like receptor-9-mediated activation of innate immunity. Immunology. Jan. 2008;123(1):118-28. Epub Oct. 23, 2007.

Plant et al., Self-assembled phospholipid/alkanethiol biomimetic bilayers on gold. Langmuir. 1993;9:2764-7.

Pokholenko et al., Lipid oligonucleotide conjugates as responsive nanomaterials for drug delivery. J of Materials Chemistry B. 2013;5329-34.

Polizzi et al., Water-soluble nitric oxide-releasing gold nanoparticles. Langmuir. Apr. 24, 2007;23(9):4938-43. Epub Mar. 22, 2007.

Ponnappa et al., Inhibition of tumor necrosis factor alpha secretion and prevention of liver injury in ethanol-fed rats by antisense oligonucleotides. Biochem Pharmacol. Feb. 15, 2005;69(4):569-77. Epub Dec. 30, 2004.

Qin et al., Significantly improved analytical sensitivity of lateral flow immunoassays by using thermal contrast. Angew Chem Int Ed Engl. Apr. 27, 2012;51(18):4358-61. doi:10.1002/anie.201200997. Epub Mar. 23, 2012.

Radovic-Moreno et al., Immunomodulatory spherical nucleic acids. Proc Natl Acad Sci U S A. Mar. 31, 2015;112(13):3892-7. doi: 10.1073/pnas.1502850112. Epub Mar. 16, 2015.

Rana et al., Monolayer coated gold nanoparticles for delivery applications. Adv Drug Deliv Rev. Feb. 2012;64(2):200-16. doi: 10.1016/j.addr.2011.08.006. Epub Sep. 6, 2011.

Rojanasakul et al., Antisense inhibition of silica-induced tumor necrosis factor in alveolar macrophages. J Biol Chem. Feb. 14, 1997;272(7):3910-4.

Romanucci et al., Synthesis, biophysical characterization and anti-HIV activity of d(TG3AG) Quadruplexes bearing hydrophobic tails at the 5'-end. Bioorg Med Chem. Feb. 1, 2014;22(3):960-6. doi: 10.1016/j.bmc.2013.12.051. Epub Jan. 4, 2014.

Rosi et al., Oligonucleotide-modified gold nanoparticles for intracellular gene regulation. Science. May 19, 2006;312(5776):1027-30.

Rothrock et al., Synthesis of nitric oxide-releasing gold nanoparticles. J Am Chem Soc. Jul. 6, 2005;127(26):9362-3.

Rush et al., Intracellular mRNA regulation with self-assembled locked nucleic acid polymer nanoparticles. J Am Chem Soc. May 28, 2014;136(21):7615-8. doi: 10.1021/ja503598z. Epub May 14, 2014.

Saraiva et al., Nanocarriers for nitric oxide delivery. J Drug Deliv. 2011;2011:936438. doi: 10.1155/2011/936438. Epub Aug. 22, 2011.

Seferos et al., Polyvalent DNA nanoparticle conjugates stabilize nucleic acids. Nano Lett. Jan. 2009;9(1):308-11.

Shahzad et al., Targeted delivery of small interfering RNA using reconstituted high-density lipoprotein nanoparticles. Neoplasia. Apr. 2011;13(4):309-19.

Shin et al., pH-responsive high-density lipoprotein-like nanoparticles to release paclitaxel at acidic pH in cancer chemotherapy. Int J Nanomedicine. 2012;7:2805-16. doi: 10.2147/IJN.S29817. Epub Jun. 6, 2012.

(56) References Cited

OTHER PUBLICATIONS

Shukoor et al., CpG-DNA loaded multifunctional MnO nanoshuttles for TLR9-specific cellular cargo delivery, selective immune-activation and MRI. J. Mater. Chem., 2012,22, 8826-8834.

Sokolova et al., The use of calcium phosphate nanoparticles encapsulating Toll-like receptor ligands and the antigen hemagglutinin to induce dendritic cell maturation and T cell activation. Biomaterials. Jul. 2010;31(21):5627-33. doi: 10.1016/j.biomaterials.2010.03.067. Epub Apr. 24, 2010.

Sood, 'Good cholesterol' nanoparticles seek and destroy cancer cells. The University of Texas MD Anderson Cancer Center. 2011. Downloaded Apr. 4, 2011. http://healthorbit.ca/newsdetail.asp?opt=1&nltid=164032911.

Stunz et al., Inhibitory oligonucleotides specifically block effects of stimulatory CpG oligonucleotides in B cells. Eur J Immunol. May 2002;32(5):1212-22.

Switaj et al., CpG immunostimulatory oligodeoxynucleotide 1826 enhances antitumor effect of interleukin 12 gene-modified tumor vaccine in a melanoma model in mice. Clin Cancer Res. Jun. 15, 2004;10(12 Pt 1):4165-75.

Tang et al., Probing hydroxyl radicals and their imaging in living cells by use of FAM-DNA-Au nanoparticles. Chemistry. Jan. 7, 2008;14(2):522-8.

Thaxton, C.S. et al., Templated Spherical High Density Lipoprotein Nanoparticles, J. Am. Chem. Soc., 2009, 131 (4), 1384-1385.

Thompson et al., Smart lipids for programmable nanomaterials. Nano Lett. Jul. 14, 2010;10(7):2690-3. doi: 10.1021/nl101640k.

Tincer et al., Immunostimulatory activity of polysaccharide-poly(I:C) nanoparticles. Biomaterials. Jun. 2011;32(18):4275-82. doi: 10.1016/j.biomaterials.2011.01.028.Epub Apr. 2, 2011.

Tiwari et al., Functionalized gold nanoparticles and their biomedical applications. Nanomaterials. 2011;1:31-63. doi: 10.3390/nano1010031.

Tripathy et al., High Density Lipoprotein Nanoparticles Deliver RNAi to Endothelial Cells to Inhibit Angiogenesis. Part Part Syst Charact. Nov. 1, 2014;31(11):1141-1150.

Wang et al., Doxorubicin-tethered responsive gold nanoparticles facilitate intracellular drug delivery for overcoming multidrug resistance in cancer cells. ACS Nano. May 24, 2011;5(5):3679-92. doi: 10.1021/nn200007z. Epub Apr. 12, 2011.

Wei et al., Polyvalent immunostimulatory nanoagents with self-assembled CpG oligonucleotide-conjugated gold nanoparticles. Angew Chem Int Ed Engl. Jan. 27, 2012;51(5):1202-6. doi:10.1002/anie. 201105187. Epub Dec. 21, 2011.

Wilson et al., pH-Responsive nanoparticle vaccines for dual-delivery of antigens and immunostimulatory oligonucleotides. ACS Nano. May 28, 2013;7(5):3912-25. doi: 10.1021/nn305466z. Epub Apr. 30, 2013.

Wilton et al. Antisense oligonucleotide-induced exon skipping across the human dystrophin gene transcript. Mol Ther. Jul. 2007;15(7):1288-96. Epub Feb. 6, 2007.

Wolfrum et al., Mechanisms and optimization of in vivo delivery of lipophilic siRNAs. Nat Biotechnol. Oct. 2007;25(10):1149-57. Epub Sep. 16, 2007.

Wu et al., DNA aptamer-micelle as an efficient detection/delivery vehicle toward cancer cells. Proc Natl Acad Sci U S A. Jan. 5, 2010;107(1):5-10. doi: 10.1073/pnas.0909611107. Epub Dec. 22, 2009.

Xiao et al., Mannosylated bioreducible nanoparticle-mediated macrophage-specific TNF-$\alpha$ RNA interference for IBD therapy. Biomaterials. Oct. 2013;34(30):7471-82. doi: 10.1016/j.biomaterials.2013.06. 008. Epub Jun. 29, 2013.

Yang et al., Biomimetic, synthetic HDL nanostructures for lymphoma. Proc Natl Acad Sci U S A. Feb. 12, 2013;110(7):2511-6. doi: 10.1073/pnas.1213657110. Epub Jan. 23, 2013.

Yang et al., Inhibition of a C-rich oligodeoxynucleotide on activation of immune cells in vitro and enhancement of antibody response in mice. Immunology. Dec. 2010;131(4):501-12. doi: 10.1111/j. 1365-2567.2010.03322.x.

Yin et al., Supramolecular self-assembled nanoparticles mediate oral delivery of therapeutic TNF-$\alpha$ siRNA against systemic inflammation. Angew Chem Int Ed Engl. May 27, 2013;52(22):5757-61. doi: 10.1002/anie.201209991. Epub Apr. 22, 2013.

Zhang et al., A general approach to DNA-programmable atom equivalents. Nat Mater. Aug. 2013;12(8):741-6. doi: 10.1038/nmat3647. Epub May 19, 2013.

Zhang et al., Informational liposomes: Complexes derived from cholesteryl-conjugated oligonucleotides and liposomes. Tetrahedron Letters. 1996. 37(35):6243-6.

Zhang et al., Nanopod formation through gold nanoparticle templated and catalyzed cross-linking of polymers bearing pendant propargyl ethers. J Am Chem Soc. Nov. 3, 2010;132(43):15151-3.

Zhang et al., Self-assembled monolayers of terminal alkynes on gold. J Am Chem Soc. Apr. 25, 2007;129(16):4876-7. Epub Mar. 31, 2007.

Zheng et al., A spherical nucleic acid platform based on self-assembled DNA biopolymer for high-performance cancer therapy. ACS Nano. Aug. 27, 2013;7(8):6545-54. doi: n402344v. Epub Jul. 23, 2013.

Zheng et al., Topical delivery of siRNA-based spherical nucleic acid nanoparticle conjugates for gene regulation. Proc Natl Acad Sci U S A. Jul. 24, 2012;109(30):11975-80. doi: 10.1073/pnas. 1118425109. Epub Jul. 6, 2012.

Knockdown of TNF by Spherical Nucleic Acids in Stimulated HKCs

| Compound | IC$_{50}$ |
|---|---|
| Oligo 3657 | 1.8 nM |
| Oligo 3661 | >100nM |

Effect of Additional Phosphorothiate Modification on Oligo 3657 Modified Spherical Nucleic Acids

| Construct | EC$_{50}$ |
|---|---|
| Oligo 5196 | 1.9 nM |
| Oligo 5289 | 1.4 nM |
| Oligo 5290 | 4.6 nM |
| Oligo 5291 | 3.0 nM |
| Oligo 5292 | 12.7 nM |
| Oligo 5293 | 12.2 nM |

TNF Knockdown with Hollow Spherical
Nucleic Acids

| Compound | IC$_{50}$ |
|---|---|
| 568T | 0.41 µM |
| ControlT | 3.6 µM |

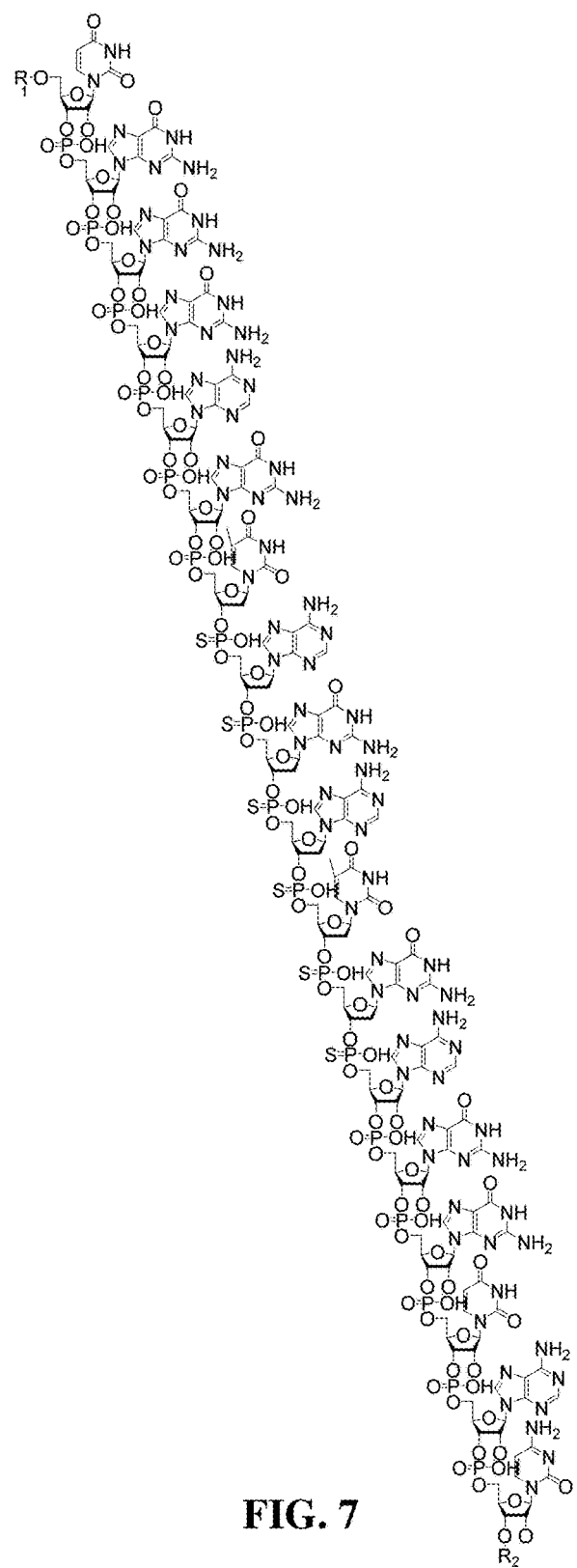
FIG. 7  SEQ ID NO: 16

SEQ ID NO: 16

SEQUENCE LISTING

<160> NUMBER OF SEQ ID NOS: 46

<210> SEQ ID NO 1
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 1
catggtgtcc tttccagg                                         18

<210> SEQ ID NO 2
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 2
tcagtgctca tggtgtcc                                         18

<210> SEQ ID NO 3
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 3
catgctttca gtgctcat                                         18

<210> SEQ ID NO 4
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 4
tgggagtaga tgaggtac                                                 18

<210> SEQ ID NO 5
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 5
ttgaccttgg tctggtag                                                 18

<210> SEQ ID NO 6
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 6
gatggcagag aggaggtt                                                 18

<210> SEQ ID NO 7
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 7
ttatctctca gctccacg                                                 18

<210> SEQ ID NO 8
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 8
atggagcaaa acccgcag                                                 18

<210> SEQ ID NO 9
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(18)
<223> OTHER INFORMATION: Modified with phosphorothioate bond

<400> SEQUENCE: 9
tgggagtaga tgaggtac                                                 18

<210> SEQ ID NO 10

-continued

<210> SEQ ID NO 10
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(18)
<223> OTHER INFORMATION: Modified with O methyl

<400> SEQUENCE: 10
ugggaguaga ugagguac                                                 18

<210> SEQ ID NO 11
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(18)
<223> OTHER INFORMATION: Modified with O methyl

<400> SEQUENCE: 11
auggagcaaa acccgcag                                                 18

<210> SEQ ID NO 12
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(18)
<223> OTHER INFORMATION: Modified with phosphorothioate bond

<400> SEQUENCE: 12
tgggagtaga tgaggtac                                                 18

<210> SEQ ID NO 13
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(18)
<223> OTHER INFORMATION: Modified with phosphorothioate bond

<400> SEQUENCE: 13
atggagcaaa acccgcag                                                 18

<210> SEQ ID NO 14
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(18)
<223> OTHER INFORMATION: Modified with phosphorothioate bond
<220> FEATURE:
<221> NAME/KEY: misc_feature
<222> LOCATION: (1)..(18)
<223> OTHER INFORMATION: Modified with O methyl

<400> SEQUENCE: 14
ugggaguaga ugagguac                                                 18

<210> SEQ ID NO 15
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(18)
<223> OTHER INFORMATION: Modified with phosphorothioate bond
<220> FEATURE:
<221> NAME/KEY: misc_feature
<222> LOCATION: (1)..(18)
<223> OTHER INFORMATION: Modified with O methyl

<400> SEQUENCE: 15
auggagcaaa acccgcag                                                 18

<210> SEQ ID NO 16
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with O methyl
<220> FEATURE:
<221> NAME/KEY: misc_feature
<222> LOCATION: (7)..(13)
<223> OTHER INFORMATION: Modified with phosphorothioate bond
<220> FEATURE:
<221> NAME/KEY: misc_feature
<222> LOCATION: (13)..(18)
<223> OTHER INFORMATION: Modified with O methyl

<400> SEQUENCE: 16
ugggagtaga tgagguac                                                 18

<210> SEQ ID NO 17
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with O methyl
<220> FEATURE:
<221> NAME/KEY: misc_feature
<222> LOCATION: (7)..(13)
<223> OTHER INFORMATION: Modified with phosphorothioate bond
<220> FEATURE:
<221> NAME/KEY: misc_feature
<222> LOCATION: (13)..(18)
<223> OTHER INFORMATION: Modified with O methyl

<400> SEQUENCE: 17
auggagcaaa acccgcag                                                 18

<210> SEQ ID NO 18
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:

<221> NAME/KEY: misc_feature
<222> LOCATION: (1)..(6)
<223> OTHER INFORMATION: Modified with O methyl
<220> FEATURE:
<221> NAME/KEY: misc_feature
<222> LOCATION: (1)..(18)
<223> OTHER INFORMATION: Modified with phosphorothioate bond
<220> FEATURE:
<221> NAME/KEY: misc_feature
<222> LOCATION: (13)..(18)
<223> OTHER INFORMATION: Modified with O methyl

<400> SEQUENCE: 18
ugggagtaga tgagguac                                                   18

<210> SEQ ID NO 19
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with O methyl
<220> FEATURE:
<221> NAME/KEY: misc_feature
<222> LOCATION: (1)..(18)
<223> OTHER INFORMATION: Modified with phosphorothioate bond
<220> FEATURE:
<221> NAME/KEY: misc_feature
<222> LOCATION: (13)..(18)
<223> OTHER INFORMATION: Modified with O methyl

<400> SEQUENCE: 19
auggagcaaa acccgcag                                                   18

<210> SEQ ID NO 20
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with O methyl
<220> FEATURE:
<221> NAME/KEY: misc_feature
<222> LOCATION: (1)..(18)
<223> OTHER INFORMATION: Modified with phosphorothioate bond
<220> FEATURE:
<221> NAME/KEY: misc_feature
<222> LOCATION: (13)..(18)
<223> OTHER INFORMATION: Modified with O methyl
<220> FEATURE:
<221> NAME/KEY: misc_feature
<222> LOCATION: (18)..(18)
<223> OTHER INFORMATION: Modified with /iSp18//iSp18//3ThioMC3-D/

<400> SEQUENCE: 20
ugggagtaga tgagguac                                                   18

<210> SEQ ID NO 21
<211> LENGTH: 17
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with O methyl

```
<220> FEATURE:
<221> NAME/KEY: misc_feature
<222> LOCATION: (1)..(18)
<223> OTHER INFORMATION: Modified with phosphorothioate bond
<220> FEATURE:
<221> NAME/KEY: misc_feature
<222> LOCATION: (13)..(18)
<223> OTHER INFORMATION: Modified with O methyl
<220> FEATURE:
<221> NAME/KEY: misc_feature
<222> LOCATION: (18)..(18)
<223> OTHER INFORMATION: Modified with /iSp18//iSp18//3ThioMC3-D/

<400> SEQUENCE: 21
auggagcaaa acccgca                                                        17

<210> SEQ ID NO 22
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with O methyl
<220> FEATURE:
<221> NAME/KEY: misc_feature
<222> LOCATION: (7)..(13)
<223> OTHER INFORMATION: Modified with phosphorothioate bond
<220> FEATURE:
<221> NAME/KEY: misc_feature
<222> LOCATION: (13)..(18)
<223> OTHER INFORMATION: Modified with O methyl
<220> FEATURE:
<221> NAME/KEY: misc_feature
<222> LOCATION: (18)..(18)
<223> OTHER INFORMATION: Modified with /iSp18//iSp18//3ThioMC3-D/

<400> SEQUENCE: 22
ugggagtaga tgagguac                                                       18

<210> SEQ ID NO 23
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with O methyl
<220> FEATURE:
<221> NAME/KEY: misc_feature
<222> LOCATION: (7)..(13)
<223> OTHER INFORMATION: Modified with phosphorothioate bond
<220> FEATURE:
<221> NAME/KEY: misc_feature
<222> LOCATION: (13)..(18)
<223> OTHER INFORMATION: Modified with O methyl
<220> FEATURE:
<221> NAME/KEY: misc_feature
<222> LOCATION: (18)..(18)
<223> OTHER INFORMATION: Modified with /iSp18//iSp18//3ThioMC3-D/

<400> SEQUENCE: 23
auggagcaaa acccgcag                                                       18

<210> SEQ ID NO 24
<211> LENGTH: 18
<212> TYPE: DNA
<213> ORGANISM: Artificial Sequence
<220> FEATURE:
```

```
<223> OTHER INFORMATION: Synthetic Polynucleotide
<220> FEATURE:
<221> NAME/KEY: misc_feature
<222> LOCATION: (18)..(18)
<223> OTHER INFORMATION: Modified with /iSp18//iSp18//3ThioMC3-D/

<400> SEQUENCE: 24
tgggagtaga tgaggtac                                                 18

<210> SEQ ID NO 25
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (18)..(18)
<223> OTHER INFORMATION: Modified with /iSp18//iSp18//3ThioMC3-D/

<400> SEQUENCE: 25
atggagcaaa acccgcag                                                 18

<210> SEQ ID NO 26
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with O methyl
<220> FEATURE:
<221> NAME/KEY: misc_feature
<222> LOCATION: (7)..(13)
<223> OTHER INFORMATION: Modified with phosphorothioate bond
<220> FEATURE:
<221> NAME/KEY: misc_feature
<222> LOCATION: (13)..(18)
<223> OTHER INFORMATION: Modified with O methyl
<220> FEATURE:
<221> NAME/KEY: misc_feature
<222> LOCATION: (18)..(18)
<223> OTHER INFORMATION: Modified with /isp18//isp18//3thiomc3-d/

<400> SEQUENCE: 26
ugggagtaga tgagguac                                                 18

<210> SEQ ID NO 27
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with O methyl
<220> FEATURE:
<221> NAME/KEY: misc_feature
<222> LOCATION: (5)..(13)
<223> OTHER INFORMATION: Modified with phosphorothioate bond
<220> FEATURE:
<221> NAME/KEY: misc_feature
<222> LOCATION: (13)..(18)
<223> OTHER INFORMATION: Modified with O methyl
<220> FEATURE:
<221> NAME/KEY: misc_feature
<222> LOCATION: (18)..(18)
<223> OTHER INFORMATION: Modified with /isp18//isp18//3thiomc3-d/

<400> SEQUENCE: 27
```

```
ugggagtaga tgagguac                                                 18

<210> SEQ ID NO 28
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with O methyl
<220> FEATURE:
<221> NAME/KEY: misc_feature
<222> LOCATION: (4)..(13)
<223> OTHER INFORMATION: Modified with phosphorothioate bond
<220> FEATURE:
<221> NAME/KEY: misc_feature
<222> LOCATION: (13)..(18)
<223> OTHER INFORMATION: Modified with O methyl
<220> FEATURE:
<221> NAME/KEY: misc_feature
<222> LOCATION: (18)..(18)
<223> OTHER INFORMATION: Modified with /isp18//isp18//3thiomc3-d/

<400> SEQUENCE: 28
ugggagtaga tgagguac                                                 18

<210> SEQ ID NO 29
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with O methyl
<220> FEATURE:
<221> NAME/KEY: misc_feature
<222> LOCATION: (3)..(13)
<223> OTHER INFORMATION: Modified with phosphorothioate bond
<220> FEATURE:
<221> NAME/KEY: misc_feature
<222> LOCATION: (13)..(18)
<223> OTHER INFORMATION: Modified with O methyl
<220> FEATURE:
<221> NAME/KEY: misc_feature
<222> LOCATION: (18)..(18)
<223> OTHER INFORMATION: Modified with /isp18//isp18//3thiomc3-d/

<400> SEQUENCE: 29
ugggagtaga tgagguac                                                 18

<210> SEQ ID NO 30
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with O methyl
<220> FEATURE:
<221> NAME/KEY: misc_feature
<222> LOCATION: (2)..(13)
<223> OTHER INFORMATION: Modified with phosphorothioate bond
<220> FEATURE:
<221> NAME/KEY: misc_feature
<222> LOCATION: (13)..(18)
<223> OTHER INFORMATION: Modified with O methyl
<220> FEATURE:
```

```
<221> NAME/KEY: misc_feature
<222> LOCATION: (18)..(18)
<223> OTHER INFORMATION: Modified with /isp18//isp18//3thiomc3-d/

<400> SEQUENCE: 30
ugggagtaga tgagguac                                                18

<210> SEQ ID NO 31
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with O methyl
<220> FEATURE:
<221> NAME/KEY: misc_feature
<222> LOCATION: (1)..(13)
<223> OTHER INFORMATION: Modified with phosphorothioate bond
<220> FEATURE:
<221> NAME/KEY: misc_feature
<222> LOCATION: (13)..(18)
<223> OTHER INFORMATION: Modified with O methyl
<220> FEATURE:
<221> NAME/KEY: misc_feature
<222> LOCATION: (18)..(18)
<223> OTHER INFORMATION: Modified with /isp18//isp18//3thiomc3-d/

<400> SEQUENCE: 31
ugggagtaga tgagguac                                                18

<210> SEQ ID NO 32
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with O methyl
<220> FEATURE:
<221> NAME/KEY: misc_feature
<222> LOCATION: (7)..(13)
<223> OTHER INFORMATION: Modified with phosphorothioate bond
<220> FEATURE:
<221> NAME/KEY: misc_feature
<222> LOCATION: (13)..(18)
<223> OTHER INFORMATION: Modified with O methyl
<220> FEATURE:
<221> NAME/KEY: misc_feature
<222> LOCATION: (18)..(18)
<223> OTHER INFORMATION: Modified with /iSp18//iSp18//toco/

<400> SEQUENCE: 32
ugggagtaga tgagguac                                                18

<210> SEQ ID NO 33
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with O methyl
<220> FEATURE:
<221> NAME/KEY: misc_feature
<222> LOCATION: (7)..(13)
<223> OTHER INFORMATION: Modified with phosphorothioate bond
```

```
<220> FEATURE:
<221> NAME/KEY: misc_feature
<222> LOCATION: (13)..(18)
<223> OTHER INFORMATION: Modified with O methyl
<220> FEATURE:
<221> NAME/KEY: misc_feature
<222> LOCATION: (18)..(18)
<223> OTHER INFORMATION: Modified with /iSp18//iSp18//toco/

<400> SEQUENCE: 33
auggagcaaa acccgcag                                                   18

<210> SEQ ID NO 34
<211> LENGTH: 3634
<212> TYPE: DNA
<213> ORGANISM: Artificial Sequence
<220> FEATURE:
<223> OTHER INFORMATION: Synthetic Polynucleotide

<400> SEQUENCE: 34
gaattccggg tgatttcact cccggctgtc caggcttgtc ctgctacccc acccagcctt     60
tcctgaggcc tcaagcctgc caccaagccc ccagctcctt ctcccgcag  gacccaaaca    120 caggcctcag gactcaacac agcttttccc tccaacccgt tttctctccc tcaacggact    180
cagctttctg aagcccctcc cagttctagt tctatctttt tcctgcatcc tgtctggaag    240
ttagaaggaa acagaccaca gacctggtcc ccaaaagaaa tggaggcaat aggttttgag    300
gggcatgggg acggggttca gcctccaggg tcctacacac aaatcagtca gtggcccaga    360 agaccccct  cggaatcgga gcagggagga tggggagtgt gaggggtatc cttgatgctt    420
gtgtgtcccc aactttccaa atccccgccc ccgcgatgga gaagaaaccg agacagaagg    480 tgcaggccc  actaccgctt cctccagatg agctcatggg tttctccacc aaggaagttt    540
tccgctggtt gaatgattct ttccccgccc tcctctcgcc ccagggacat ataaaggcag    600
ttgttggcac acccagccag cagacgctcc ctcagcaagg acagcagagg accagctaag    660
agggagagaa gcaactacag acccccctg  aaaacaaccc tcagacgcca catcccctga    720
caagctgcca ggcaggttct cttcctctca catactgacc cacggcttca ccctctctcc    780
cctggaaagg acaccatgag cactgaaagc atgatccggg acgtgagct  ggccgaggag    840 gcgctcccca agaagacagg ggggcccag  ggctccaggc ggtgcttgtt cctcagcctc    900
ttctccttcc tgatcgtggc aggcgccacc acgctcttct gctgctgca  ctttggagtg    960 atcggccccc agagggaaga ggtgagtgcc tggccagcct tcatccactc tcccacccaa   1020
ggggaaatga gagacgcaag agaggggagag atagggatg  ggtgaaagat gtgcgctgat   1080
agggagggat gagagagaaa aaaacatgga gaaagacggg gatgcagaaa gagatgtggc   1140
aagagatggg gaagagagag agagaaagat ggagagacag gatgtctggc acatggaagg   1200
tgctcactaa gtgtgtatgg agtgaatgaa tgaatgaatg aatgaacaag cagatatata   1260
aataagatat ggagacagat gtggggtgtg agagagaga  tggggaaga  aacaagtgat   1320 atgaataaag atggtgagac agaaagagcg ggaaatatga cagctaagga gagagatggg   1380
ggagataagg agagaagaag ataggggtgtc tggcacacag aagacactca gggaaagagc   1440
tgttgaatgc tggaaggtga atacacagat gaatggagag agaaaaccag acacctcagg   1500
gctaagagcg caggccagac aggcagccag ctgttcctcc tttaagggtg actccctcga   1560
tgttaaccat tctccttctc cccaacagtt ccccagggac ctctctctaa tcagccctct   1620
ggcccaggca gtcagtaagt gtctccaaac ctctttccta attctgggtt tgggtttggg   1680
```

| | |
|---|---|
| ggtagggtta gtaccggtat ggaagcagtg ggggaaattt aaagttttgg tcttgggga | 1740 |
| ggatggatgg aggtgaaagt aggggggtat tttctaggaa gtttaagggt ctcagctttt | 1800 |
| tcttttctct ctcctcttca ggatcatctt ctcgaacccc gagtgacaag cctgtagccc | 1860 |
| atgttgtagg taagagctct gaggatgtgt cttggaactt ggagggctag gatttgggga | 1920 |
| ttgaagcccg gctgatggta ggcagaactt ggagacaatg tgagaaggac tcgctgagct | 1980 |
| caagggaagg gtggaggaac agcacaggcc ttagtgggat actcagaacg tcatggccag | 2040 |
| gtgggatgtg ggatgacaga cagagaggac aggaaccgga tgtggggtgg gcagagctcg | 2100 |
| agggccagga tgtggagagt gaaccgacat ggccacactg actctcctct ccctctctcc | 2160 |
| ctccctccag caaaccctca agctgagggg cagctccagt ggctgaaccg ccgggccaat | 2220 |
| gccctcctgg ccaatggcgt ggagctgaga gataaccagc tggtggtgcc atcagagggc | 2280 |
| ctgtacctca tctactccca ggtcctcttc aagggccaag gctgcccctc cacccatgtg | 2340 |
| ctcctcaccc acaccatcag ccgcatcgcc gtctcctacc agaccaaggt caacctcctc | 2400 |
| tctgccatca agagccctg ccagagggag accccgagg gggctgaggc caagcccctgg | 2460 |
| tatgagccca tctatctggg agggtcttc cagctggaga agggtgaccg actcagcgct | 2520 |
| gagatcaatc ggcccgacta tctcgacttt gccgagtctg ggcaggtcta ctttgggatc | 2580 |
| attgccctgt gaggaggacg aacatccaac cttcccaaac gcctcccctg ccccaatccc | 2640 |
| tttattaccc cctccttcag acaccctcaa cctcttctgg ctcaaaaaga gaattggggg | 2700 |
| cttagggtcg gaacccaagc ttagaacttt aagcaacaag accaccactt cgaaacctgg | 2760 |
| gattcaggaa tgtgtggcct gcacagtgaa gtgctggcaa ccactaagaa ttcaaactgg | 2820 |
| ggcctccaga actcactggg gcctacagct ttgatccctg acatctggaa tctggagacc | 2880 |
| agggagcctt tggttctggc cagaatgctg caggacttga gaagacctca cctagaaatt | 2940 |
| gacacaagtg gaccttaggc cttcctctct ccagatgttt ccagacttcc ttgagacacg | 3000 |
| gagcccagcc ctccccatgg agccagctcc ctctatttat gtttgcactt gtgattattt | 3060 |
| attatttatt tattatttat ttatttacag atgaatgtat ttatttggga gaccggggta | 3120 |
| tcctggggga cccaatgtag gagctgcctt ggctcagaca tgttttccgt gaaaacggag | 3180 |
| ctgaacaata ggctgttccc atgtagcccc ctggcctctg tgccttcttt tgattatgtt | 3240 |
| ttttaaaata tttatctgat taagttgtct aaacaatgct gatttggtga ccaactgtca | 3300 |
| ctcattgctg agcctctgct ccccagggga gttgtgtctg taatcgccct actattcagt | 3360 |
| ggcgagaaat aaagtttgct tagaaaagaa acatggtctc cttcttggaa ttaattctgc | 3420 |
| atctgcctct tcttgtgggt gggaagaagc tccctaagtc ctctctccac aggctttaag | 3480 |
| atccctcgga cccagtccca tccttagact cctagggccc tggagaccct acataaacaa | 3540 |
| agcccaacag aatattcccc atccccagg aaacaagagc ctgaacctaa ttacctctcc | 3600 |
| ctcagggcat gggaatttcc aactctggga attc | 3634 |

<210> SEQ ID NO 35
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with O methyl
<220> FEATURE:
<221> NAME/KEY: misc_feature
<222> LOCATION: (7)..(13)
<223> OTHER INFORMATION: Modified with phosphorothioate bond
<220> FEATURE:
<221> NAME/KEY: misc_feature
<222> LOCATION: (13)..(18)
<223> OTHER INFORMATION: Modified with O methyl
<220> FEATURE:
<221> NAME/KEY: misc_feature
<222> LOCATION: (18)..(18)
<223> OTHER INFORMATION: Modified with /iSp18//iSp18//iSp18//3CholTEG/

<400> SEQUENCE: 35
ugggagtaga tgagguac                                            18

<210> SEQ ID NO 36
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with O methyl
<220> FEATURE:
<221> NAME/KEY: misc_feature
<222> LOCATION: (7)..(13)
<223> OTHER INFORMATION: Modified with phosphorothioate bond
<220> FEATURE:
<221> NAME/KEY: misc_feature
<222> LOCATION: (13)..(18)
<223> OTHER INFORMATION: Modified with O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 36
ugggagtaga tgagguac                                            18

<210> SEQ ID NO 37
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with O methyl
<220> FEATURE:
<221> NAME/KEY: misc_feature
<222> LOCATION: (7)..(13)
<223> OTHER INFORMATION: Modified with phosphorothioate bond
<220> FEATURE:
<221> NAME/KEY: misc_feature
<222> LOCATION: (13)..(18)
<223> OTHER INFORMATION: Modified with O methyl
<220> FEATURE:
<221> NAME/KEY: misc_feature
<222> LOCATION: (18)..(18)
<223> OTHER INFORMATION: Modified with /iSp18//3CholTEG/

<400> SEQUENCE: 37
ugggagtaga tgagguac                                            18

<210> SEQ ID NO 38
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:

```
<221> NAME/KEY: misc_feature
<222> LOCATION: (1)..(6)
<223> OTHER INFORMATION: Modified with O methyl
<220> FEATURE:
<221> NAME/KEY: misc_feature
<222> LOCATION: (7)..(13)
<223> OTHER INFORMATION: Modified with phosphorothioate bond
<220> FEATURE:
<221> NAME/KEY: misc_feature
<222> LOCATION: (13)..(18)
<223> OTHER INFORMATION: Modified with O methyl
<220> FEATURE:
<221> NAME/KEY: misc_feature
<222> LOCATION: (18)..(18)
<223> OTHER INFORMATION: Modified with /3CholTEG/

<400> SEQUENCE: 38
ugggagtaga tgagguac                                                  18

<210> SEQ ID NO 39
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with O methyl
<220> FEATURE:
<221> NAME/KEY: misc_feature
<222> LOCATION: (7)..(13)
<223> OTHER INFORMATION: Modified with phosphorothioate bond
<220> FEATURE:
<221> NAME/KEY: misc_feature
<222> LOCATION: (13)..(18)
<223> OTHER INFORMATION: Modified with O methyl
<220> FEATURE:
<221> NAME/KEY: misc_feature
<222> LOCATION: (18)..(18)
<223> OTHER INFORMATION: Modified with /iSp18//iSp18//iSp18//3CholTEG/

<400> SEQUENCE: 39
auggagcaaa acccgcag                                                  18

<210> SEQ ID NO 40
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with O methyl
<220> FEATURE:
<221> NAME/KEY: misc_feature
<222> LOCATION: (7)..(13)
<223> OTHER INFORMATION: Modified with phosphorothioate bond
<220> FEATURE:
<221> NAME/KEY: misc_feature
<222> LOCATION: (13)..(18)
<223> OTHER INFORMATION: Modified with O methyl
<220> FEATURE:
<221> NAME/KEY: misc_feature
<222> LOCATION: (18)..(18)
<223> OTHER INFORMATION: Modified with /iSp18//iSp18//3CholTEG/

<400> SEQUENCE: 40
auggagcaaa acccgcag                                                  18

<210> SEQ ID NO 41
<211> LENGTH: 18
```

```
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with O methyl
<220> FEATURE:
<221> NAME/KEY: misc_feature
<222> LOCATION: (7)..(13)
<223> OTHER INFORMATION: Modified with phosphorothioate bond
<220> FEATURE:
<221> NAME/KEY: misc_feature
<222> LOCATION: (13)..(18)
<223> OTHER INFORMATION: Modified with O methyl
<220> FEATURE:
<221> NAME/KEY: misc_feature
<222> LOCATION: (18)..(18)
<223> OTHER INFORMATION: Modified with /iSp18//3CholTEG/

<400> SEQUENCE: 41
auggagcaaa acccgcag                                                 18

<210> SEQ ID NO 42
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with O methyl
<220> FEATURE:
<221> NAME/KEY: misc_feature
<222> LOCATION: (7)..(13)
<223> OTHER INFORMATION: Modified with phosphorothioate bond
<220> FEATURE:
<221> NAME/KEY: misc_feature
<222> LOCATION: (13)..(18)
<223> OTHER INFORMATION: Modified with O methyl
<220> FEATURE:
<221> NAME/KEY: misc_feature
<222> LOCATION: (18)..(18)
<223> OTHER INFORMATION: Modified with /3CholTEG/

<400> SEQUENCE: 42
auggagcaaa acccgcag                                                 18

<210> SEQ ID NO 43
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with O methyl
<220> FEATURE:
<221> NAME/KEY: misc_feature
<222> LOCATION: (7)..(13)
<223> OTHER INFORMATION: Modified with phosphorothioate bond
<220> FEATURE:
<221> NAME/KEY: misc_feature
<222> LOCATION: (13)..(18)
<223> OTHER INFORMATION: Modified with O methyl
<220> FEATURE:
<221> NAME/KEY: misc_feature
<222> LOCATION: (18)..(18)
<223> OTHER INFORMATION: Modified with /iSp18//iSp18//3Toco/

<400> SEQUENCE: 43
```

```
guuucaccac ccaauucc                                                    18
```

```
<210> SEQ ID NO 44
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with O methyl
<220> FEATURE:
<221> NAME/KEY: misc_feature
<222> LOCATION: (7)..(13)
<223> OTHER INFORMATION: Modified with phosphorothioate bond
<220> FEATURE:
<221> NAME/KEY: misc_feature
<222> LOCATION: (13)..(18)
<223> OTHER INFORMATION: Modified with O methyl
<220> FEATURE:
<221> NAME/KEY: misc_feature
<222> LOCATION: (18)..(18)
<223> OTHER INFORMATION: Modified with /iSp18//iSp18//3Toco/

<400> SEQUENCE: 44
ugggagtaga caagguac                                                    18
```

```
<210> SEQ ID NO 45
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with O methyl
<220> FEATURE:
<221> NAME/KEY: misc_feature
<222> LOCATION: (7)..(13)
<223> OTHER INFORMATION: Modified with phosphorothioate bond
<220> FEATURE:
<221> NAME/KEY: misc_feature
<222> LOCATION: (13)..(18)
<223> OTHER INFORMATION: Modified with O methyl
<220> FEATURE:
<221> NAME/KEY: misc_feature
<222> LOCATION: (18)..(18)
<223> OTHER INFORMATION: Modified with /iSp18// iSp18//chol/

<400> SEQUENCE: 45
ugggagtaga tgagguac                                                    18
```

```
<210> SEQ ID NO 46
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with O methyl
<220> FEATURE:
<221> NAME/KEY: misc_feature
<222> LOCATION: (7)..(13)
<223> OTHER INFORMATION: Modified with phosphorothioate bond
<220> FEATURE:
<221> NAME/KEY: misc_feature
<222> LOCATION: (13)..(18)
<223> OTHER INFORMATION: Modified with O methyl
<220> FEATURE:
<221> NAME/KEY: misc_feature
```

```
<222> LOCATION: (18)..(18)
<223> OTHER INFORMATION: Modified with /iSp18//iSp18//3Chol/

<400> SEQUENCE: 46
ugggagtaga caagguac                                                    18
```

ANTI-TNF COMPOUNDS

RELATED APPLICATION

This application is a national stage filing under U.S.C. § 371 of PCT International Application PCT/US2015/054288, which claims priority under 35 U.S.C. § 119(e) to U.S. Provisional Application Ser. No. 62/060,424, entitled "ANTI-TNF COMPOUNDS" filed on Oct. 6, 2014, which are herein incorporated by reference in their entirety.

FIELD OF INVENTION

The invention relates to anti-TNF nucleic acid compounds, as well as methods of use thereof and compositions thereof.

BACKGROUND OF INVENTION

TNF-α (tumor necrosis factor-alpha) is a pleiotropic cytokine produced by activated macrophages/monocytes and lymphocytes which often promotes inflammatory responses leading to a variety of diseases. TNF-α is released from macrophages, monocytes and natural killer cells and play an important role in inflammatory and immune responses, including the recruitment of leukocytes to injured tissues during bacterial and other microbial infections, and following stimulation with inflammatory substances. When present in excessive quantities, TNF-α is known to cause tissue injury, and has been implicated in the pathology associated with inflammatory and autoimmune diseases.

TNF-α mediates biological effects through two distinct membrane-protein receptors, TNF-RI and TNF-RII, which differ in sequence and molecular mass. TNF-RI is reported to be present at low levels in most, if not all, human cell types, and expression of the TNF-RI gene in humans can be upregulated by infection, interferons, and modulators of second messengers, such as phorbol esters. The extracellular portions of both TNF receptors also exist in soluble forms, which are derived from membrane-bound forms of the receptors by proteolytic cleavage at the cell surface. The soluble TNF receptors retain the ability to bind TNF-α in solution. Soluble TNF receptors have been identified in urine and sera from healthy individuals, and have been shown to be elevated in some chronic diseases and following inoculation with agents that induce TNF-α.

SUMMARY OF INVENTION

In some aspects, the invention is a compound comprising the structure depicted in FIG. 7 (SEQ ID NO: 16) or salts thereof. In some embodiments the compound is 18 nucleotides in length. In other embodiments the compound is formulated in a composition with a carrier. In another embodiments, the compound is a sodium salt. In other embodiments the compound is the structure depicted in FIG. 8 (SEQ ID NO: 16).

In some embodiments the compound further comprises a molecular species at one of the ends. In other embodiments the compound further comprises a molecular species at both ends.

In yet another embodiment the molecular species is selected from the group consisting of a spacer, a lipid, a sterol, cholesterol, stearyl, C16 alkyl chain, bile acids, cholic acid, taurocholic acid, deoxycholate, oleyl litocholic acid, oleoyl cholenic acid, glycolipids, phospholipids, sphingolipids, isoprenoids, such as steroids, vitamins, such as vitamin E, saturated fatty acids, unsaturated fatty acids, fatty acid esters, such as triglycerides, pyrenes, porphyrines, Texaphyrine, adamantane, acridines, biotin, coumarin, fluorescein, rhodamine, Texas-Red, digoxygenin, dimethoxytrityl, t-butyldimethylsilyl, t-butyldiphenylsilyl, cyanine dyes (e.g. Cy3 or Cy576), Hoechst 33258 dye, psoralen, and ibuprofen.

In another embodiment the molecular species is a selected from the group consisting of a lipophilic moiety; a folic acid radical; a steroid radical; a carbohydrate radical; a vitamin A radical; a vitamin E radical; or a vitamin K radical.

In another embodiment the molecular species is connected directly to the compound through a linkage selected from the group consisting of phosphodiester, phosphorothioate, methylphosphonate, and amide linkages. In some embodiments the molecular species is connected indirectly to the compound through a linker.

In other embodiments the linker is a non-nucleotidic linker selected from the group consisting of abasic residues (dSpacer), oligoethyleneglycol, such as triethyleneglycol (spacer 9) or hexaethylenegylcol (spacer 18), and alkanediol, such as butanediol.

Another aspect of the invention is an oligonucleotide comprising mUmGmGmGmAmGT*A*G*A*T*G*mAmGmGmUm AmC (SEQ ID NO. 16), wherein the oligonucleotide is 18 nucleotides in length, wherein m is a 2'O methyl, and wherein * is a phosphorothioate modification. In some embodiments the oligonucleotide is formulated in a composition with a carrier. In other embodiments the carrier is a lipid based carrier. In another embodiment the carrier is a nanoparticle.

In another embodiment the oligonucleotide further comprises a molecular species at the 3' or 5' end. In some embodiments the oligonucleotide further comprises a molecular species at both the 3' and 5' ends.

In other embodiments the molecular species is selected from the group consisting of a spacer, a lipid, a sterol, cholesterol, stearyl, C16 alkyl chain, bile acids, cholic acid, taurocholic acid, deoxycholate, oleyl litocholic acid, oleoyl cholenic acid, glycolipids, phospholipids, sphingolipids, isoprenoids, such as steroids, vitamins, such as vitamin E, saturated fatty acids, unsaturated fatty acids, fatty acid esters, such as triglycerides, pyrenes, porphyrines, Texaphyrine, adamantane, acridines, biotin, coumarin, fluorescein, rhodamine, Texas-Red, digoxygenin, dimethoxytrityl, t-butyldimethylsilyl, t-butyldiphenylsilyl, cyanine dyes (e.g. Cy3 or Cy576), Hoechst 33258 dye, psoralen, and ibuprofen.

In some embodiments the molecular species is a selected from the group consisting of a lipophilic moiety; a folic acid radical; a steroid radical; a carbohydrate radical; a vitamin A radical; a vitamin E radical; or a vitamin K radical. In another embodiment the molecular species is connected directly to the compound through a linkage selected from the group consisting of phosphodiester, phosphorothioate, methylphosphonate, and amide linkages. In yet another embodiment the molecular species is connected indirectly to the compound through a linker.

In some embodiments the linker is a non-nucleotidic linker selected from the group consisting of abasic residues (dSpacer), oligoethyleneglycol, such as triethyleneglycol (spacer 9) or hexaethylenegylcol (spacer 18), and alkanediol, such as butanediol.

In other aspects the invention is an oligonucleotide comprising 5' TGGGAGTAGATGAGGTAC 3' (SEQ ID NO. 4), wherein the oligonucleotide is 18-19 nucleotides in length, wherein 4-6 nucleotides at the 5' end and 4-6 nucleotides at the 3' end of the oligonucleotide include a 2'O methyl, and wherein 4-10 nucleotides have a phosphorothioate modification. In some embodiments the 6 nucleotides at the 5' end and 6 nucleotides at the 3' end of the oligonucleotide include a 2'O methyl. In other embodiments 6 nucleotides have a phosphorothioate modification. In another embodiment 7 nucleotides have a phosphorothioate modification. In yet another embodiment 8 nucleotides have a phosphorothioate modification.

In other embodiments the phosphorothioate modified nucleotides are in a central region of the oligonucleotide.

In another embodiment the internucleotide linkage associated with the seventh, eighth, ninth, tenth, eleventh, and twelfth nucleotide from the 5' end of the oligonucleotide is phosphorothioate modified.

In another embodiment each nucleotide has either a 2'O methyl modification or phosphorothioate internucleotide linkage. In some embodiments only one nucleotide has both a 2'O methyl modification and a phosphorothioate internucleotide linkage. In other embodiments only one nucleotide has a 2'-modified nucleotide.

In some embodiments the 2'-modification is selected from the group of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-dimethylaminopropyl (2'-O-DMAP), 2'-O-dimethylaminoethyloxyethyl(2'-O-DMAEOE), and 2'-O—N-methylacetamido (2'-O-NMA).

One aspect of the invention is a stable self-assembling nanostructure, comprising an antisense oligonucleotide of 18-19 nucleotides in length comprising TGGGAGTAGATGAGGTAC (SEQ ID NO. 4), wherein a hydrophobic group at the 3' or 5' terminus self-associates to form the core of the nanostructure in water or other suitable solvents. Self-assembling nanostructures are generally formed when oligonucleotide is at concentrations above 5 µM in DNase and RNase free water or other suitable solvents. In some embodiments the antisense oligonucleotide is 18 nucleotides in length. In other embodiments the antisense oligonucleotide has phosphodiester internucleotide linkages. In another embodiment less than all of the internucleotide linkages are phosphodiester.

Another aspect of the invention is a stable self-assembling nanostructure, comprising an antisense oligonucleotide of 18-19 nucleotides in length comprising TGGGAGTAGATGAGGTAC (SEQ ID NO. 4), wherein the antisense oligonucleotide is associated with a core. In some embodiments the antisense oligonucleotide is 18 nucleotides in length. In other embodiments the antisense oligonucleotide has phosphodiester internucleotide linkages. In another embodiment less than all of the internucleotide linkages are phosphodiester.

In other embodiments the antisense oligonucleotide has phosphorothioate internucleotide linkages. In some embodiments less than all of the internucleotide linkages are phosphorothioate.

In some embodiments the antisense oligonucleotide has 2'O methyl modifications. In other embodiment less than all of the nucleotides include a 2'O methyl modification.

In another embodiment the antisense oligonucleotide has 17 internucleotide linkages and wherein the 6 central internucleotide linkages are phosphorothioate. In other embodiments the first 6 internucleotide linkages at the 5' end of the oligonucleotide are phosphodiester internucleotide linkages. In yet another embodiment the first 6 nucleotides at the 5' end of the oligonucleotide are 2'O methyl modified nucleotides.

In other embodiments the last 5 nucleotides at the 3' end of the oligonucleotide are 2'O methyl modified nucleotides.

In another embodiment the antisense oligonucleotide is selected from the group consisting of T-G-G-G-A-G-T-A-G-A-T-G-A-G-G-T-A-C (SEQ ID NO. 4), mUmGmGmGmAmGmUmAmGmAmUmGmAmGmGmUmAmC (SEQ ID NO. 10, Oligo 3742), T*G*G*G*A*G*T*A*G*A*T*G*A*G*G*T*A*C (SEQ ID NO. 9, Oligo 3500), mUmGmGmGmAmGT*A*G*A*T*G*mAmGmGmUm AmC (SEQ ID NO. 16, Oligo 3534), and mU*mG*mG*mG*mA*mG*T*A*G*A*T*G*mA*mG* mG*mU*mA*mC (SEQ ID NO. 18, Oligo 3509) wherein— refers to a phosphodiester bond, * refers to a phosphorothioate bond, and m refers to a O methyl.

In another embodiment the antisense oligonucleotide is linked to the exterior of the core. In some embodiments the nanostructure includes 2-1,000 copies of the antisense oligonucleotide.

In other embodiments the nanostructure includes at least one oligonucleotide structurally distinct from the antisense oligonucleotide.

In some embodiments the antisense oligonucleotide has its 5'-terminus exposed to the outside surface of the nanostructure. In other embodiments the antisense oligonucleotide has its 3'-terminus exposed to the outside surface of the nanostructure. In some embodiments the antisense oligonucleotide is positioned laterally on the surface of the nanostructure.

In another embodiment the antisense oligonucleotide is indirectly linked to the core through a linker. In some embodiments the antisense oligonucleotide is indirectly linked to the core through more than one linker.

In some embodiments the core is a solid or hollow core. In other embodiments the core is inert, paramagnetic or superparamagnetic. In another embodiment the core is a solid core.

In other embodiments the solid core is comprised of noble metals, including gold and silver, transition metals including iron and cobalt, metal oxides including silica, polymers or combinations thereof. In another embodiments the core is a polymeric core and wherein the polymeric core is comprised of amphiphilic block copolymers, hydrophobic polymers including polystyrene, poly(lactic acid), poly(lactic co-glycolic acid), poly(glycolic acid), poly(caprolactone) and other biocompatible polymers.

In yet another embodiment the core is a liposomal core.

Another aspect of the invention is a composition comprising the previously discussed embodiments of the compound, the oligonucleotide or the nanostructure, further comprising a therapeutic agent for treating a TNF disorder associated with the nanostructure. In some embodiments the therapeutic agent is linked to the oligonucleotide.

Each of the compositions and nucleic acids described herein may be formulated in a variety of carriers. In some embodiments the compounds of the invention are formulated in a topical carrier. In some embodiments the topical formulation is a cream. In other embodiments the topical formulation is a gel.

Another aspect of the invention is a method for treating a TNF disorder, comprising administering to a subject having a TNF disorder a composition comprising the previously described aspects of the compound, the oligonucleotide or the nanostructure in an effective amount to treat the TNF disorder.

In another embodiment the TNF disorder is selected from the group consisting of an autoimmune disease, an infectious disease, transplant rejection or graft-versus-host disease, malignancy, a pulmonary disorder, an intestinal disorder, a cardiac disorder, sepsis, a spondyloarthropathy, a metabolic disorder, anemia, pain, a hepatic disorder, a skin disorder, a nail disorder, rheumatoid arthritis, psoriasis, psoriasis in combination with psoriatic arthritis, ulcerative colitis, Crohn's disease, vasculitis, Behcet's disease, ankylosing spondylitis, asthma, chronic obstructive pulmonary disorder (COPD), idiopathic pulmonary fibrosis (IPF), restenosis, diabetes, anemia, pain, a Crohn's disease-related disorder, juvenile rheumatoid arthritis (JRA), a hepatitis C virus infection, psoriatic arthritis, and chronic plaque psoriasis.

In some embodiments the autoimmune disorder is selected from the group consisting of rheumatoid arthritis, rheumatoid spondylitis, osteoarthritis, gouty arthritis, allergy, multiple sclerosis, autoimmune diabetes, autoimmune uveitis, and nephritic syndrome.

In another aspect the invention is a method for reducing TNF levels in vivo, comprising administering to a subject a composition comprising the previously described embodiments of the compound, the oligonucleotide or the nanostructure in an effective amount to reduce TNF levels in vivo.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

In FIG. 4A, the percent TNF-α mRNA expression between Oligo 3657 and its control, Oligo 3661 is shown graphically. FIG. 4B represents the compounds' half maximal inhibitory concentrations ($IC_{50}$), 1.8 nM and >100 nM, respectively.

In FIG. 5A, the percent relative mRNA expression of oligonucleotides with increasing phosphorothioate content is graphed.

FIG. 5B shows a table of the half maximal effective concentration ($EC_{50}$) of each oligonucleotide screened.

In FIG. 6A, the TNF expression, normalized to untreated is shown, while FIG. 6B shows the compounds' $IC_{50}$ values.

FIG. 7 is a structure of a free acid form of a TNF antisense oligonucleotide, which corresponds to SEQ ID NO: 16.

In FIG. 12A, clinical scores of the disease are shown for the vehicle, TNBS, Oligo 227901 in S-SNA format of various dosing amounts. In FIG. 12B, clinical scores of the disease are shown for the vehicle, TNBS, Oligo 227901 in L-SNA format of various dosing amounts. In FIG. 12C, gross pathology scores of disease are shown for the vehicle, TNBS, Oligo 227901 in S-SNA format of various dosing amounts. In FIG. 12D, gross pathology scores of disease are shown for the vehicle, TNBS, Oligo 227901 in L-SNA format of various dosing amounts. * indicates $p<0.05$ vs. Vehicle group using One-Way ANOVA followed by post-hoc Tukey test.

DETAILED DESCRIPTION

Figure 1:
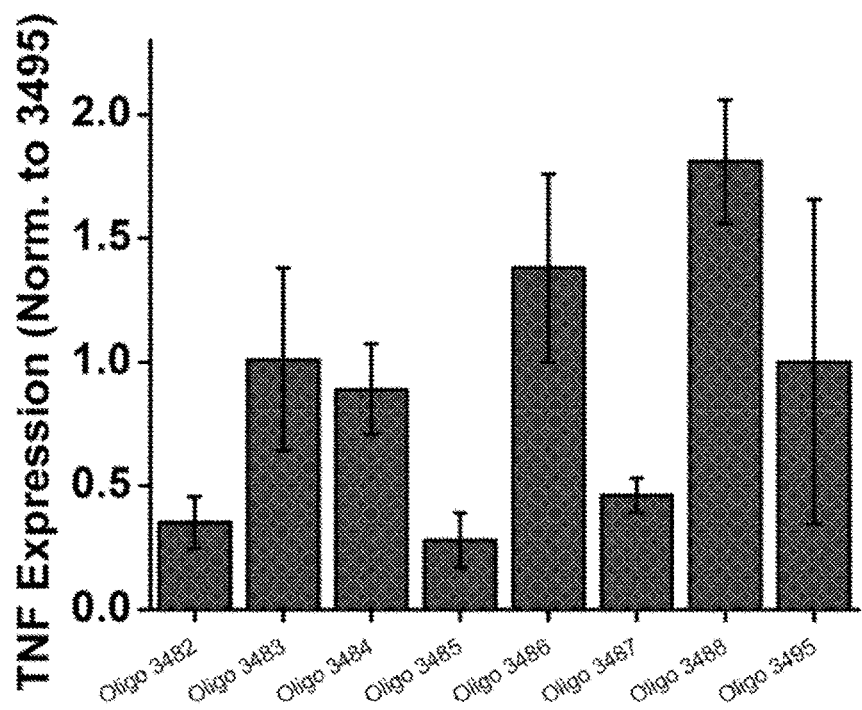
FIG. 1 is a bar graph showing inhibitory activity in primary human keratinocytes of several oligonucleotides including Oligo 3482, 3483, 3484, 3485, 3486, 3487, and 3488, normalized to Oligo 3495 (a scrambled control) on TNF expression.

The invention in some aspects relates to compositions for reducing TNFα and methods for treating a TNF disorder using those compositions. Highly effective TNFα inhibitors have been identified according to aspects of the invention. The TNFα inhibitors are nucleic acid based antisense compositions. The term "TNF-alpha" or "TNF-α" refers to a cytokine that exists as a 17 kD secreted form and a 26 kD membrane associated form, the biologically active form of which is composed of a trimer of noncovalently bound 17 kD molecules.

A "TNFα inhibitor" as used herein refers to a nucleic acid based agent which interferes with TNFα activity. In particular, the TNFα antisense inhibitors or TNFα antisense oligonucleotides of the invention reduce the expression of the TNFα gene.

The TNF inhibitors of the invention are antisense nucleic acids. Antisense nucleic acids typically include modified or unmodified RNA, DNA, or mixed polymer nucleic acids, and primarily function by specifically binding to matching sequences resulting in modulation of peptide synthesis. Antisense nucleic acids bind to target RNA by Watson Crick base-pairing and block gene expression by preventing ribosomal translation of the bound sequences either by steric blocking or by activating RNase H enzyme. Antisense molecules may also alter protein synthesis by interfering with RNA processing or transport from the nucleus into the cytoplasm.

As used herein, the term "antisense nucleic acid" or "antisense oligonucleotide" describes a nucleic acid that hybridizes under physiological conditions to DNA comprising a particular gene or to an mRNA transcript of that gene in this case TNFα and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence.

"Inhibition of gene expression" refers to the absence or observable decrease in the level of protein and/or mRNA product from a target gene, such as the TNFα gene. "Specificity" refers to the ability to inhibit the target gene without manifest effects on other genes of the cell. The consequences of inhibition can be confirmed by examination of the outward properties of the cell or organism or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS).

The antisense oligonucleotides of the invention inhibit TNFα expression. Depending on the assay, quantitation of the amount of gene expression allows one to determine a degree of inhibition which is greater than 5%, 10%, 20%, 30%, 40%, 50%, 60%, 70%, 80%, 90%, 95% or 99% as compared to a cell not treated according to the present invention. As an example, the efficiency of inhibition may be determined by assessing the amount of gene product in the cell.

In some instances the TNFα inhibitor is a compound having the following structure or bioequivalents including salts and prodrugs thereof:

(SEQ ID NO: 16)

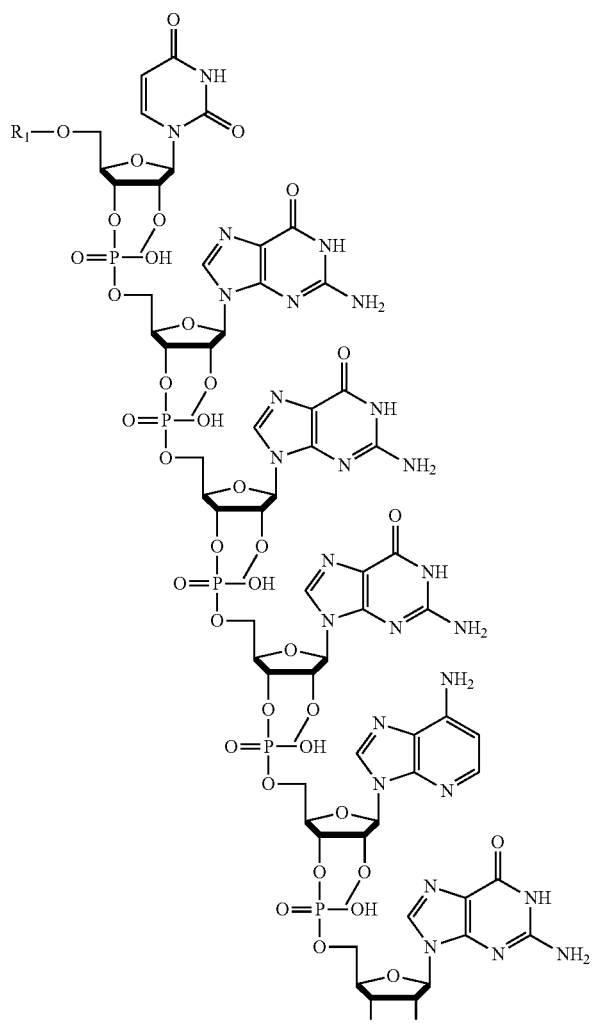

-continued
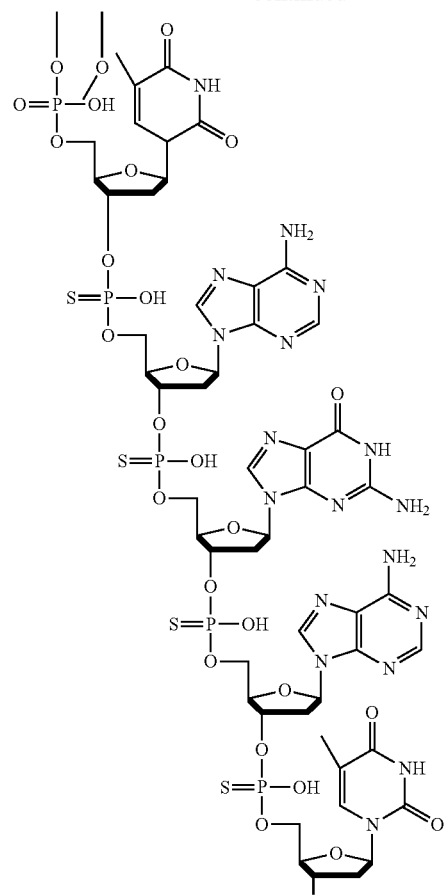
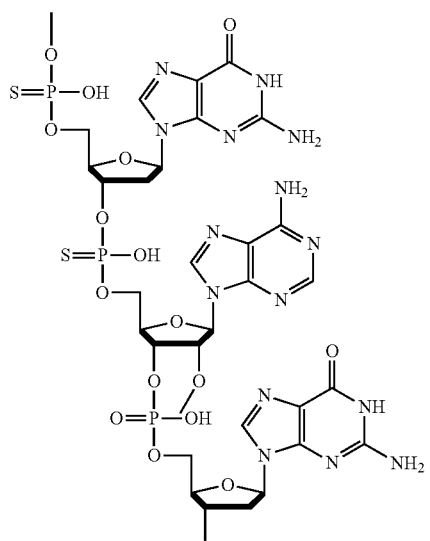

-continued

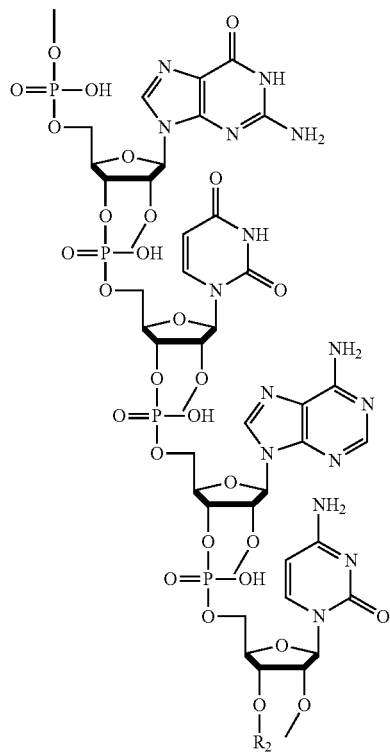

The term bioequivalent compounds, including pharmaceutically acceptable salts and prodrugs as used herein refers to antisense oligonucleotides having the same primary structure as the antisense oligonucleotide of interest, but including salt forms or structures which can be cleaved or modified to have the same type of biological effect as the antisense oligonucleotide of interest. This is intended to encompass any pharmaceutically acceptable salts, esters, or salts of such esters, or any other compound which, upon administration to an animal including a human, is capable of providing (directly or indirectly) the biologically active metabolite or residue thereof.

"Pharmaceutically acceptable salts" are physiologically and pharmaceutically acceptable salts of the nucleic acids of the invention: i.e., salts that retain the desired biological activity of the compound of interest and do not impart undesired toxicological effects thereto. Pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

An example of a salt of the antisense oligonucleotide of the invention is for example a compound which is a sodium salt having the following structure:

(SEQ ID NO: 16)
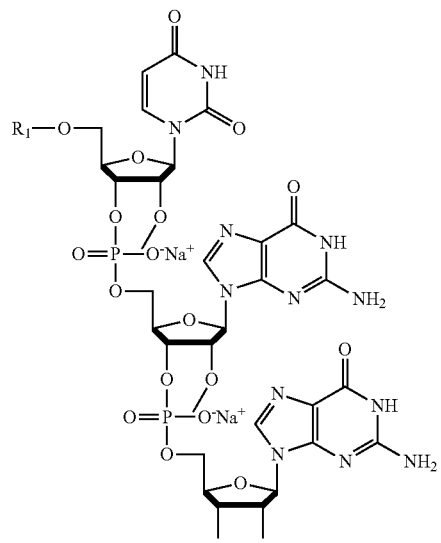
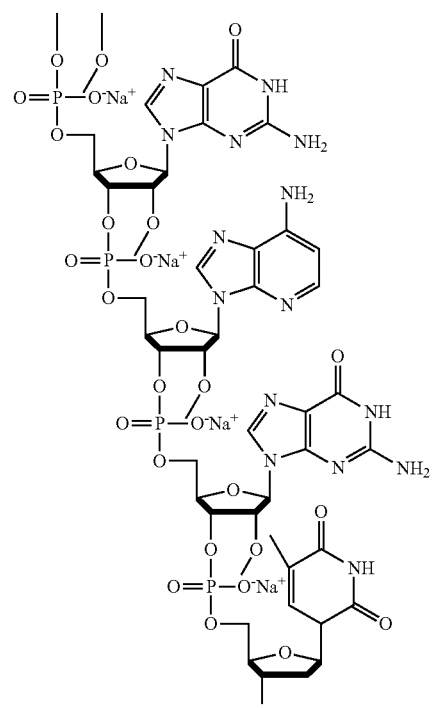

-continued
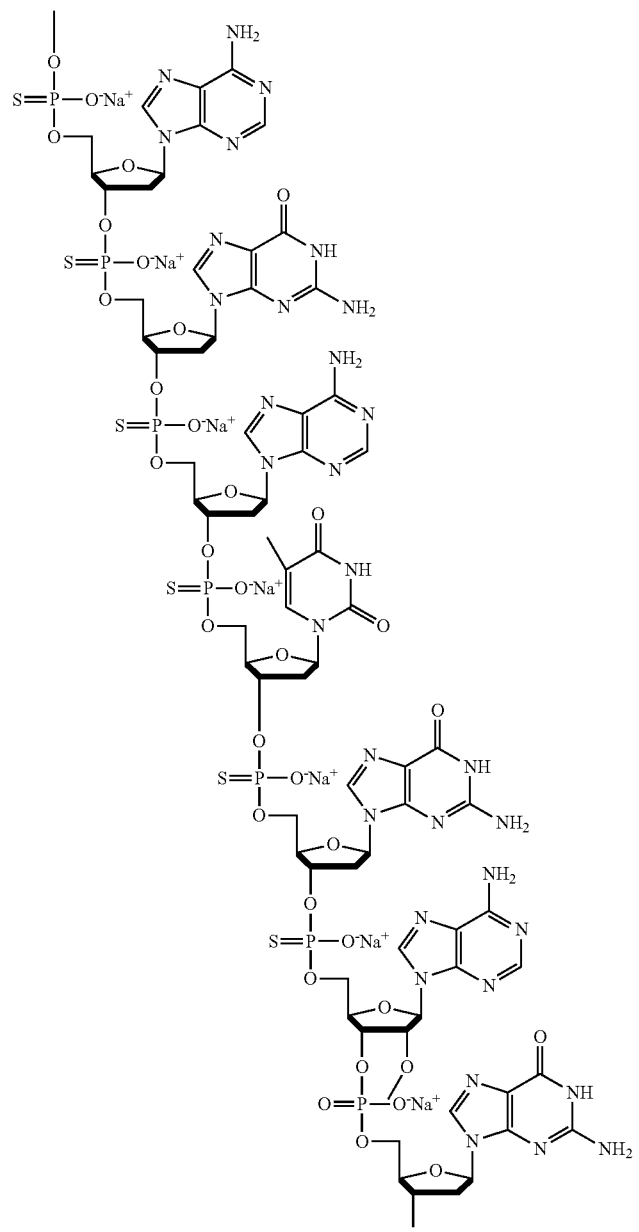

-continued

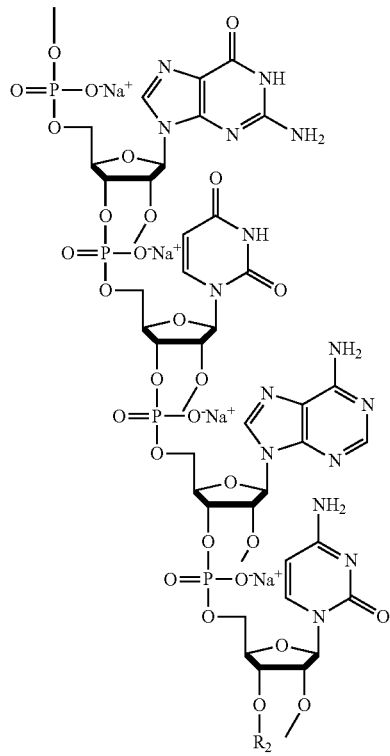

The compounds of the invention may also be prepared to be delivered in a "prodrug" form. A "prodrug" is a therapeutic agent that is prepared in an inactive form that is converted to an active form (i.e., drug) within the body or cells thereof by the action of endogenous enzymes or other chemicals and/or conditions.

The antisense oligonucleotides of the invention are TNFα antisense oligonucleotides. An antisense TNFα oligonucleotide refers to a compound having a sequence of nucleotide bases and a subunit-to-subunit backbone that allows the antisense oligonucleotide to hybridize to a TNFα target sequence typically by Watson-Crick base pairing, to form an RNA:oligomer heteroduplex within the target sequence.

The specific hybridization of an antisense oligonucleotide with its target nucleic acid, TNFα, interferes with the normal function of the nucleic acid, TNFα. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of TNFα protein. In the context of the present invention, "modulation" means a decrease or inhibition in the expression of a gene.

An antisense oligonucleotide "specifically hybridizes" to a target polynucleotide if the oligonucleotide hybridizes to the TNFα target under physiological conditions, with a thermal melting point (Tm) substantially greater than 37° C., preferably at least 45° C., and typically 50° C.–80° C. or higher. Such hybridization preferably corresponds to stringent hybridization conditions, selected to be about 10° C., and preferably about 50° C. lower than the Tm for the specific sequence at a defined ionic strength and pH. At a given ionic strength and pH, the Tm is the temperature at which 50% of a target sequence hybridizes to a complementary polynucleotide.

Polynucleotides are described as "complementary" to one another when hybridization occurs in an antiparallel configuration between two single-stranded polynucleotides. A double-stranded polynucleotide can be "complementary" to another polynucleotide, if hybridization can occur between one of the strands of the first polynucleotide and the second. Complementarity (the degree that one polynucleotide is complementary with another) is quantifiable in terms of the proportion of bases in opposing strands that are expected to form hydrogen bonds with each other, according to generally accepted base-pairing rules. An antisense compound may be complementary to a target region of a target transcript even if the two bases sequences are not 100% complementary, as long as the heteroduplex structure formed between the compound and transcript has the desired Tm stability.

Identifying an antisense oligonucleotide that targets a particular nucleic acid may be a multistep process. The process usually begins with the identification of a nucleic acid sequence whose function is to be modulated. This may be, for example, a cellular gene (or mRNA transcribed from the gene) whose expression is associated with a particular TNFα disorder or disease state. The targeting process also includes determination of a site or sites within this TNFα gene for the antisense interaction to occur such that the desired effect, e.g., detection or modulation of expression of the protein, will result. Within the context of the present invention, a preferred intragenic site is the region encompassing the nucleotide sequence 2283-2300 of SEQ ID NO. 34, ie. gtacctca tctactccca (SEQ ID NO. 35).

Preferred antisense oligonucleotides are designed to target human TNFα, for instance, the nucleotide sequence of SEQ ID NO. 34, set forth below. Human TNF-α cDNA sequence has been published by Nedwin, G. E. et al. (Nucleic Acids Res. 1985, 13, 6361-6373); and is disclosed in Genbank accession number X02910.

```
                                                             (SEQ ID NO. 34)
   1    gaattccggg tgatttcact cccggctgtc caggcttgtc ctgctacccc acccagcctt
  61    tcctgaggcc tcaagcctgc caccaagccc ccagctcctt ctcccgcag  gacccaaaca
 121    caggcctcag gactcaacac agcttttccc tccaacccgt tttctctccc tcaacggact
 181    cagctttctg aagcccctcc cagttctagt tctatctttt tcctgcatcc tgtctggaag
 241    ttagaaggaa acagaccaca gacctggtcc ccaaaagaaa tggaggcaat aggttttgag
 301    gggcatgggg acggggttca gcctccaggg tcctacacac aaatcagtca gtggcccaga
 361    agaccccct  cggaatcgga gcagggagga tggggagtgt gagggtatc  cttgatgctt
 421    gtgtgtcccc aactttccaa atccccgccc ccgcgatgga gaagaaccg  agacagaagg
 481    tgcagggccc actaccgctt cctccagatg agctcatggg tttctccacc aaggaagttt
 541    tccgctggtt gaatgattct ttccccgccc tcctctcgcc ccagggacat ataaaggcag
 601    ttgttggcac acccagccag cagacgctcc ctcagcaagg acagcagagg accagctaag
 661    agggagagaa gcaactacag acccccctg  aaaacaaccc tcagacgcca catcccctga
 721    caagctgcca ggcaggttct cttcctctca catactgacc cacggcttca ccctctctcc
 781    cctggaaagg acaccatgag cactgaaagc atgatccggg acgtggagct ggccgaggag
 841    gcgctcccca agaagacagg ggggcccag  ggctccaggc ggtgcttgtt cctcagcctc
 901    ttctccttcc tgatcgtggc aggcgccacc acgctcttct gcctgctgca ctttggagtg
 961    atcggccccc agagggaaga ggtgagtgcc tggccagcct tcatccactc tcccacccaa
1021    ggggaaatga gagacgcaag agaggagag  agatgggatg ggtgaaagat gtgcgctgat
1081    agggagggat gagagagaaa aaacatgga  gaaagacggg gatgcagaaa gagatgtggc
1141    aagagatggg gaagagagag agagaaagat ggagagacag gatgtctggc acatggaagg
1201    tgctcactaa gtgtgtatgg agtgaatgaa tgaatgaatg aatgaacaag cagatatata
1261    aataagatat ggagacagat gtggggtgtg agaagagaga tggggaaga  aacaagtgat
1321    atgaataaag atggtgagac agaaagagcg ggaaatatga cagctaagga gagagatggg
1381    ggagataagg agagaagaag atagggtgtc tggcacacag aagacactca gggaaagagc
1441    tgttgaatgc tggaaggtga atacacagat gaatggagag agaaaaccag acacctcagg
1501    gctaagagcg caggccagac aggcagccag ctgttcctcc tttaagggtg actccctcga
1561    tgttaaccat tctccttctc cccaacagtt ccccagggac ctctctctaa tcagccctct
1621    ggcccaggca gtcagtaagt gtctccaaac ctctttccta attctgggtt tgggtttggg
1681    ggtagggtta gtaccggtat ggaagcagtg ggggaaattt aaagttttgg tcttggggga
1741    ggatggatgg aggtgaaagt aggggggtat tttctaggaa gtttaagggt ctcagctttt
1801    tctttctct  ctcctcttca ggatcatctt ctcgaacccc gagtgacaag cctgtagccc
1861    atgttgtagg taagagctct gaggatgtgt cttggaactt ggagggctag gatttgggga
1921    ttgaagcccg gctgatggta ggcagaactt ggagacaatg tgagaaggac tcgctgagct
1981    caagggaagg gtggaggaac agcacaggcc ttagtgggat actcagaacg tcatggccag
2041    gtgggatgtg ggatgacaga cagagaggac aggaaccgga tgtggggtgg gcagagctcg
2101    agggccagga tgtggagagt gaaccgacat ggccacactg actctcctct ccctctctcc
2161    ctccctccag caaaccctca agctgagggg cagctccagt ggctgaaccg ccgggccaat
```

```
-continued
2221    gccctcctgg ccaatggcgt ggagctgaga gataaccagc tggtggtgcc atcagagggc 2281    ctgtacctca tctactccca ggtcctcttc aagggccaag gctgccccct cacccatgtg 2341    ctcctcaccc acaccatcag ccgcatcgcc gtctcctacc agaccaaggt caacctcctc 2401    tctgccatca agagccctg ccagagggag accccagagg gggctgaggc caagccctgg 2461    tatgagccca tctatctggg aggggtcttc cagctggaga agggtgaccg actcagcgct 2521    gagatcaatc ggcccgacta tctcgacttt gccgagtctg ggcaggtcta ctttgggatc 2581    attgccctgt gaggaggacg aacatccaac cttcccaaac gcctccctg ccccaatccc 2641    tttattaccc cctccttcag acaccctcaa cctcttctgg ctcaaaaaga gaattggggg 2701    cttagggtcg gaacccaagc ttagaacttt aagcaacaag accaccactt cgaaacctgg 2761    gattcaggaa tgtgtggcct gcacagtgaa gtgctggcaa ccactaagaa ttcaaactgg 2821    ggcctccaga actcactggg gcctacagct ttgatccctg acatctggaa tctggagacc 2881    agggagcctt tggttctggc cagaatgctg caggacttga gaagacctca cctagaaatt 2941    gacacaagtg gaccttaggc cttcctctct ccagatgttt ccagacttcc ttgagacacg 3001    gagcccagcc ctccccatgg agccagctcc ctctatttat gtttgcactt gtgattattt 3061    attatttatt tattatttat ttatttacag atgaatgtat ttatttggga gaccggggta 3121    tcctggggga cccaatgtag gagctgcctt ggctcagaca tgttttccgt gaaaacggag 3181    ctgaacaata ggctgttccc atgtagcccc ctggcctctg tgccttcttt tgattatgtt 3241    ttttaaaata tttatctgat taagttgtct aaacaatgct gatttggtga ccaactgtca 3301    ctcattgctg agcctctgct ccccagggga gttgtgtctg taatcgccct actattcagt 3361    ggcgagaaat aaagtttgct tagaaaagaa acatggtctc cttcttggaa ttaattctgc 3421    atctgcctct tcttgtgggt gggaagaagc tccctaagtc ctctctccac aggctttaag 3481    atccctcgga cccagtccca tccttagact cctagggccc tggagaccct acataaacaa 3541    agcccaacag aatattcccc atcccccagg aaacaagagc ctgaacctaa ttacctctcc 3601    ctcagggcat gggaatttcc aactctggga attc
```

The nanostructures descried herein may be stable self-assembling nanostructures. For instance the nanostructure may be an antisense oligonucleotide of 18-19 nucleotides in length comprising TGGGAGTAGATGAGGTAC (SEQ ID NO. 4), wherein a hydrophobic group at the 3' or 5' terminus self-associates to form the core of the nanostructure in water or other suitable solvents. A hydrophobic group as used herein may include cholesterol, a cholesteryl or modified cholesteryl residue, adamantine, dihydrotesterone, long chain alkyl, long chain alkenyl, long chain alkynyl, olely-lithocholic, cholenic, oleoyl-cholenic, palmityl, heptadecyl, myrisityl, bile acids, cholic acid or taurocholic acid, deoxycholate, oleyl litocholic acid, oleoyl cholenic acid, glycolipids, phospholipids, sphingolipids, isoprenoids, such as steroids, vitamins, such as vitamin E, fatty acids either saturated or unsaturated, fatty acid esters, such as triglycerides, pyrenes, porphyrines, Texaphyrine, adamantane, acridines, biotin, coumarin, fluorescein, rhodamine, Texas-Red, digoxygenin, dimethoxytrityl, t-butyldimethylsilyl, t-butyldiphenylsilyl, cyanine dyes (e.g. Cy3 or Cy5), Hoechst 33258 dye, psoralen, or ibuprofen.

The antisense oligonucleotides typically have a length of 15-20 bases, which is generally long enough to have one complementary sequence in the mammalian genome. Additionally, antisense compounds having a length of at least 12, typically at least 15 nucleotides in length hybridize well with their target mRNA. Thus, the antisense oligonucleotides of the invention are typically in a size range of 8-100 nucleotides, more preferably 12-50 nucleotides in length. In some embodiments of the invention the antisense oligonucleotides are of 18-19 nucleotides in length and comprise TGGGAGTAGATGAGGTAC (SEQ ID NO. 4). Antisense oligonucleotides that comprise SEQ ID NO. 4 may include further nucleotides on the 5' and/or 3' end of the oligonucleotide. However an antisense oligonucleotide that comprises SEQ ID NO. 4 and is limited to 18 nucleotides in length does not have any additional nucleotides on the 5' or 3' end of the molecule. Other non-nucleotide molecules may be linked covalently or non-covalently to the 5' and/or 3' end of the those oligonucleotides.

In some instances, the antisense oligonucleotide is one of the following oligonucleotides: T-G-G-G-A-G-T-A-G-A-T-G-A-G-G-T-A-C (SEQ ID NO. 4), mUmGmGmGmAmG-mUmAmGmAmUmGmAmGmGmUmAmC (SEQ ID NO. 10, Oligo 3742), T*G*G*G*A*G*T*A*G*A*T*G*A*G*G*T*A*C (SEQ ID NO. 9, Oligo 3500), mUmGmGmGmAmGT*A*G*A*T*G*mAmGmGmUmAmC (SEQ ID NO. 16, Oligo 3534), and mU*mG*mG*mG*mA*mG*T*A*G*A*T*G*mA*mG*mG*mU*mA*mC (SEQ ID NO. 18, Oligo 3509) wherein—refers to a phosphodiester bond, * refers to a phosphorothioate bond, and m refers to a O methyl.

The terms "nucleic acid" and "oligonucleotide" are used interchangeably to mean multiple nucleotides (i.e., molecules comprising a sugar (e.g., ribose or deoxyribose) linked to a phosphate group and to an exchangeable organic base, which is either a substituted pyrimidine (e.g., cytosine (C), thymine (T) or uracil (U)) or a substituted purine (e.g., adenine (A) or guanine (G)). As used herein, the terms "nucleic acid" and "oligonucleotide" refer to oligoribonucleotides as well as oligodeoxyribonucleotides. The terms "nucleic acid" and "oligonucleotide" shall also include polynucleosides (i.e., a polynucleotide minus the phosphate) and any other organic base containing polymer. Nucleic acid molecules are preferably synthetic (e.g., produced by nucleic acid synthesis). The oligonucleotides may be any size useful for producing antisense effects. In some embodiments they are 18-23 nucleotides in length. In other embodiments the antisense oligonucleotide is 18 nucleotides in length.

The terms "nucleic acid" and "oligonucleotide" may also encompass nucleic acids or oligonucleotides with substitutions or modifications, such as in the bases and/or sugars. For example, they include nucleic acids having backbone sugars that are covalently attached to low molecular weight organic groups other than a hydroxyl group at the 2' position and other than a phosphate group or hydroxy group at the 5' position. Thus modified nucleic acids may include a 2'-O-alkylated ribose group. In addition, modified nucleic acids may include sugars such as arabinose or 2'-fluoroarabinose instead of ribose. Thus the nucleic acids may be heterogeneous in backbone composition thereby containing any possible combination of polymer units linked together such as peptide-nucleic acids (which have an amino acid backbone with nucleic acid bases). Other examples are described in more detail below.

The oligonucleotides may be DNA, RNA, PNA, LNA, ENA or hybrids including any chemical or natural modification thereof. Chemical and natural modifications are well known in the art. Such modifications include, for example, modifications designed to increase binding to a target strand (i.e., increase their melting temperatures), to assist in identification of the oligonucleotide or an oligonucleotide-target complex, to increase cell penetration, to stabilize against nucleases and other enzymes that degrade or interfere with the structure or activity of the oligonucleotides, to provide a mode of disruption (a terminating event) once sequence-specifically bound to a target, and to improve the pharmacokinetic properties of the oligonucleotide.

Modifications include, but are not limited to, for example, (a) end modifications, e.g., 5' end modifications (phosphorylation dephosphorylation, conjugation, inverted linkages, etc.), 3' end modifications (conjugation, DNA nucleotides, inverted linkages, etc.), (b) base modifications, e.g., replacement with modified bases, stabilizing bases, destabilizing bases, or bases that base pair with an expanded repertoire of partners, or conjugated bases, (c) sugar modifications (e.g., at the 2' position or 4' position) or replacement of the sugar, as well as (d) internucleoside linkage modifications, including modification or replacement of the phosphodiester linkages. To the extent that such modifications interfere with translation (i.e., results in a reduction of 50%, 60%, 70%, 80%, or 90% or more in translation relative to the lack of the modification—e.g., in an in vitro translation assay), the modification may not be optimal for the methods and compositions described herein.

Non-limiting examples of modified internucleoside linkages include phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Modified internucleoside linkages that do not include a phosphorus atom therein have internucleoside linkages that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Substituted sugar moieties include, but are not limited to one of the following at the 2' position: H (deoxyribose); OH (ribose); F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl.

A chemically or naturally modified oligonucleotide may include, for example, at least one nucleotide modified at the 2' position of the sugar, most preferably a 2'-O-alkyl, 2'-O-alkyl-O-alkyl or 2'-fluoro-modified nucleotide or an end cap. In other embodiments, RNA modifications include 2'-fluoro, 2'-amino and 2' O-methyl modifications on the ribose of pyrimidines, abasic residues or an inverted base at the 3' end of the RNA.

The oligonucleotides useful according to the invention may include a single modified nucleoside. In other embodiments the oligonucleotide may include at least two modified nucleosides, at least 3, at least 4, at least 5, at least 6, at least 7, at least 8, at least 9, at least 10, at least 15, at least 20 or more nucleosides, up to the entire length of the oligonucleotide.

Nucleosides or nucleobases include the natural purine bases adenine (A) and guanine (G), and the pyrimidine bases thymine (T), cytosine (C) and uracil (U). Modified nucleosides include other synthetic and natural nucleobases such as inosine, xanthine, hypoxanthine, nubularine, isoguanisine, tubercidine, 2-(halo)adenine, 2-(alkyl)adenine, 2-(propyl)adenine, 2 (amino)adenine, 2-(aminoalkyl)adenine, 2 (aminopropyl)adenine, 2 (methylthio) N6 (isopentenyl)adenine, 6 (alkyl)adenine, 6 (methyl)adenine, 7 (deaza)adenine, 8 (alkenyl)adenine, 8-(alkyl)adenine, 8 (alkynyl)adenine, 8 (amino)adenine, 8-(halo)adenine, 8-(hydroxyl) adenine, 8 (thioalkyl) adenine, 8-(thiol)adenine, N6-(isopentyl)adenine, N6 (methyl)adenine, N6, N6 (dimethyl) adenine, 2-(alkyl)guanine, 2 (propyl)guanine, 6-(alkyl) guanine, 6 (methyl)guanine, 7 (alkyl)guanine, 7 (methyl) guanine, 7 (deaza)guanine, 8 (alkyl)guanine, 8-(alkenyl) guanine, 8 (alkynyl)guanine, 8-(amino)guanine, 8 (halo) guanine, 8-(hydroxyl)guanine, 8 (thioalkyl)guanine, 8-(thiol)guanine, N (methyl)guanine, 2-(thio)cytosine, 3 (deaza) 5 (aza)cytosine, 3-(alkyl)cytosine, 3 (methyl)cytosine, 5-(alkyl)cytosine, 5-(alkynyl)cytosine, 5 (halo)cytosine, 5 (methyl)cytosine, 5 (propynyl)cytosine, 5 (propynyl) cytosine, 5 (trifluoromethyl)cytosine, 6-(azo)cytosine, N4 (acetyl)cytosine, 3 (3 amino-3 carboxypropyl)uracil, 2-(thio)uracil, 5 (methyl) 2 (thio)uracil, 5 (methylaminomethyl)-2 (thio)uracil, 4-(thio)uracil, 5 (methyl) 4 (thio)uracil, 5 (methylaminomethyl)-4 (thio)uracil, 5 (methyl) 2,4 (dithio)uracil, 5 (methylaminomethyl)-2,4 (dithio)uracil, 5 (2-aminopropyl)uracil, 5-(alkyl)uracil, 5-(alkynyl)uracil, 5-(allylamino)uracil, 5 (aminoallyl)uracil, 5 (aminoalkyl) uracil, 5 (guanidiniumalkyl)uracil, 5 (1,3-diazole-1-alkyl) uracil, 5-(cyanoalkyl)uracil, 5-(dialkylaminoalkyl)uracil, 5 (dimethylaminoalkyl)uracil, 5-(halo)uracil, 5-(methoxy)uracil, uracil-5 oxyacetic acid, 5 (methoxycarbonylmethyl)-2-(thio)uracil, 5 (methoxycarbonyl-methyl)uracil, 5 (propynyl)uracil, 5 (propynyl)uracil, 5 (trifluoromethyl)uracil, 6 (azo) uracil, dihydrouracil, N3 (methyl)uracil, 5-uracil (i.e., pseudouracil), 2 (thio)pseudouracil, 4 (thio)pseudouracil,2,4-(dithio)pseudouracil, 5-(alkyl)pseudouracil, 5-(methyl) pseudouracil, 5-(alkyl)-2-(thio)pseudouracil, 5-(methyl)-2-(thio)pseudouracil, 5-(alkyl)-4 (thio)pseudouracil, 5-(methyl)-4 (thio)pseudouracil, 5-(alkyl)-2,4 (dithio) pseudouracil, 5-(methyl)-2,4 (dithio)pseudouracil, 1 substituted pseudouracil, 1 substituted 2(thio)-pseudouracil, 1 substituted 4 (thio)pseudouracil, 1 substituted 2,4-(dithio) pseudouracil, 1 (aminocarbonylethylenyl)-pseudouracil, 1 (aminocarbonylethylenyl)-2(thio)-pseudouracil, 1 (aminocarbonylethylenyl)-4 (thio)pseudouracil, 1 aminocarbonylethylenyl)-2,4-(dithio)pseudouracil, 1 (arninoalkylarninocarbonylethylenyl)-pseudouracil, 1 (arninoalkylarninocarbonylethylenyl)-2(thio)-pseudouracil, 1(arninoalkylarninocarbonylethylenyl)-4 (thio)pseudouracil, 1 (arninoalkylarninocarbonylethylenyl)-2,4-(dithio) pseudouracil, 1,3-(diaza)-2-(oxo)-phenoxazin-1-yl, 1-(aza)-2-(thio)-3-(aza)-phenoxazin-1-yl, 1,3-(diaza)-2-(oxo)-phenthiazin-1-yl, 1-(aza)-2-(thio)-3-(aza)-phenthiazin-1-yl, 7-substituted 1,3-(diaza)-2-(oxo)-phenoxazin-1-yl, 7-substituted 1-(aza)-2-(thio)-3-(aza)-phenoxazin-1-yl, 7-substituted 1,3-(diaza)-2-(oxo)-phenthiazin-1-yl, 7-substituted 1-(aza)-2-(thio)-3-(aza)-phenthiazin-1-yl, 7-(arninoalkylhydroxy)-1,3-(diaza)-2-(oxo)-phenoxazin-1-yl, 7-(arninoalkylhydroxy)-1-(aza)-2-(thio)-3-(aza)-phenoxazin-1-yl, 7-(aminoalkylhydroxy)-1,3-(diaza)-2-(oxo)-phenthiazin-1-yl, 7-(arninoalkylhydroxy)-1-(aza)-2-(thio)-3-(aza)-phenthiazin-1-yl, 7-(guanidiniumalkylhydroxy)-1,3-(diaza)-2-(oxo)-phenoxazin-1-yl, 7-(guanidiniumalkylhydroxy)-1-(aza)-2-(thio)-3-(aza)-phenoxazin-1-yl, 7-(guanidiniumalkyl-hydroxy)-1,3-(diaza)-2-(oxo)-phenthiazin-1-yl, 7-(guanidiniumalkylhydroxy)-1-(aza)-2-(thio)-3-(aza)-phenthiazin-1-yl, 1,3,5-(triaza)-2,6-(dioxa)-naphthalene, inosine, xanthine, hypoxanthine, nubularine, tubercidine, isoguanisine, inosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, 3-(methyl)isocarbostyrilyl, 5-(methyl)isocarbostyrilyl, 3-(methyl)-7-(propynyl)isocarbostyrilyl, 7-(aza)indolyl, 6-(methyl)-7-(aza)indolyl, imidizopyridinyl, 9-(methyl)-imidizopyridinyl, pyrrolopyrizinyl, isocarbostyrilyl, 7-(propynyl)isocarbostyrilyl, propynyl-7-(aza)indolyl, 2,4,5-(trimethyl)phenyl, 4-(methyl)indolyl, 4,6-(dimethyl)indolyl, phenyl, napthalenyl, anthracenyl, phenanthracenyl, pyrenyl, stilbenyl, tetracenyl, pentacenyl, diiluorotolyl, 4-(iluoro)-6-(methyl)benzimidazole, 4-(methyl)benzimidazole, 6-(azo) thymine, 2-pyridinone, 5 nitroindole, 3 nitropyrrole, 6-(aza) pyrimidine, 2 (amino)purine, 2,6-(diamino) purine, 5 substituted pyrimidines, N2-substituted purines, N6-substituted purines, 06-substituted purines, substituted 1,2,4-triazoles, pyrrolo-pyrimidin-2-on-3-yl, 6-phenyl-pyrrolo-pyrimidin-2-on-3-yl, para-substituted-6-phenyl-pyrrolo-pyrimidin-2-on-3-yl, ortho-substituted-6-phenyl-pyrrolo-pyrimidin-2-on-3-yl, bis-ortho-substituted-6-phenyl-pyrrolo-pyrimidin-2-on-3-yl, para-(aminoalkylhydroxy)-6-phenyl-pyrrolo-pyrimidin-2-on-3-yl, ortho-(aminoalkylhydroxy)-6-phenyl-pyrrolo-pyrimidin-2-on-3-yl, bis-ortho-(aminoalkylhydroxy)-6-phenyl-pyrrolo-pyrimidin-2-on-3-yl, pyridopyrimidin-3-yl, 2-oxo-7-amino-pyridopyrimidin-3-yl, 2-oxo-pyridopyrimidine-3-yl, or any O-alkylated or N-alkylated derivatives thereof.

The antisense oligonucleotides of the invention may be chimeric oligonucleotides. Chimeric antisense compounds of the invention may be formed as composite structures of two or more oligonucleotides, modified oligonucleotides, oligonucleotides and/or oligonucleotide mimetics as described above. Such compounds have also been referred to in the art as hybrids or gapmers. In particular a gapmer is an oligonucleotide that has at least three discrete portions, two of which are similar i.e. include one or more backbone modifications, and surround a region that is distinct, i.e., does not include backbone modifications.

The oligonucleotides may include a molecular species at one or both ends, i.e., at the 3' and/or 5' end. A molecular species as used herein refers to any compound that is not a naturally occurring or non-naturally occurring nucleotide. Molecular species include but are not limited to a spacer, a lipid, a sterol, lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, an octadecylamine or hexylamino-carbonyl-oxycholesterol moiety, stearyl, C16 alkyl chain, bile acids, cholic acid, taurocholic acid, deoxycholate, oleyl litocholic acid, oleoyl cholenic acid, glycolipids, phospholipids, sphingolipids, isoprenoids, such as steroids, vitamins, such as vitamin E, saturated fatty acids, unsaturated fatty acids, fatty acid esters, such as triglycerides, pyrenes, porphyrines, Texaphyrine, adamantane, acridines, biotin, coumarin, fluorescein, rhodamine, Texas-Red, digoxygenin, dimethoxytrityl, t-butyldimethylsilyl, t-butyldiphenylsilyl, cyanine dyes (e.g. Cy3 or Cy576), Hoechst 33258 dye, psoralen, or ibuprofen.

The molecular species may be attached at various positions of the oligonucleotide. As described above, the molecular species may be linked to the 3'-end or 5'-end of the oligonucleotide, where it also serves the purpose to enhance the stability of the oligomer against 3'- or 5'-exonucleases. Alternatively, it may be linked to an internal nucleotide or a nucleotide on a branch. The molecular species may be attached to a 2'-position of the nucleotide. The molecular species may also be linked to the heterocyclic base of the nucleotide.

The molecular species may be connected to the oligonucleotide by a linker moiety. Optionally the linker moiety is a non-nucleotidic linker moiety. Non-nucleotidic linkers are e.g. abasic residues (dSpacer), oligoethyleneglycol, such as triethyleneglycol or hexaethylenegylcol, or alkane-diol, such as butanediol. The spacer units are preferably linked by phosphodiester or phosphorothioate bonds. The linker units may appear just once in the molecule or may be incorporated several times, e.g. via phosphodiester, phosphorothioate, methylphosphonate, or amide linkages.

The oligonucleotide of the invention (separate from the linkers connecting nucleotides to the molecular species) may also contain non-nucleotidic linkers, in particular abasic linkers (dSpacers), trietyhlene glycol units or hexaethylene glycol units. Further preferred linkers are alkylamino linkers, such as C3, C6, C12 aminolinkers, and also alkylthiol linkers, such as C3 or C6 thiol linkers.

TNFα plays a role in a wide variety of TNFα-related disorders. A TNFα disorder as used herein refers to a disorder in which TNFα activity is detrimental to a particular physiological function in a subject. As used herein, the term "a disorder in which TNFα activity is detrimental" is intended to include diseases and other disorders in which the levels of TNFα expressed in a subject suffering from the disorder plays a role in the pathophysiology of the disorder or as a factor that contributes to a worsening of or maintenance of the disorder. Accordingly, a disorder in which TNFα activity is detrimental is a disorder in which inhibition of TNFα activity is expected to alleviate at least one symptom and/or progression or worsening of the disorder. Such disorders may be evidenced, for example, by an increase in the concentration of TNFα in a biological fluid of a subject suffering from the disorder (e.g., an increase in the concentration of TNFα in serum, plasma, synovial fluid, etc. of the subject), which can be detected, for example, using a TNFα probe or an anti-TNFα antibody for detecting TNFα message or protein respectively.

TNFα disorders include but are not limited to sepsis, infections, autoimmune diseases, cancer, transplant rejection and graft-versus-host disease, transplant rejection, malignancy, a pulmonary disorder, an intestinal disorder, a cardiac disorder, sepsis, a spondyloarthropathy, a metabolic disorder, anemia, pain, a hepatic disorder, a skin disorder, a nail disorder, rheumatoid arthritis, psoriasis, psoriasis in combination with psoriatic arthritis, ulcerative colitis, Crohn's disease, vasculitis, Behcet's disease, ankylosing spondylitis, asthma, chronic obstructive pulmonary disorder (COPD), idiopathic pulmonary fibrosis (IPF), restenosis, diabetes, anemia, pain, a Crohn's disease-related disorder, juvenile rheumatoid arthritis (JRA), a hepatitis C virus infection, psoriatic arthritis, and chronic plaque psoriasis.

The biological role played by TNFα in several of these diseases is described below. Inhibiting TNFα expression in these diseases provides a therapeutic treatment for the disorder. TNFα plays a role in sepsis. Biological effects include hypotension, myocardial suppression, vascular leakage syndrome, organ necrosis, stimulation of the release of toxic secondary mediators and activation of the clotting cascade.

TNFα has been implicated in autoimmune disease, for example, by activating tissue inflammation and causing joint destruction in rheumatoid arthritis, promoting the death of islet cells and in mediating insulin resistance in diabetes, mediating cytotoxicity to oligodendrocytes and induction of inflammatory plaques in multiple sclerosis, mediating cytotoxicity to oligodendrocytes and induction of inflammatory plaques in multiple sclerosis, and in the development of Crohn's disease.

The biological effects observed in a variety of infectious diseases are due to TNFα. For example, TNFα has been implicated in mediating brain inflammation and capillary thrombosis and infarction in malaria, mediating brain inflammation, inducing breakdown of the blood-brain barrier, triggering septic shock syndrome and activating venous infarction in meningitis, and in inducing cachexia, stimulating viral proliferation and mediating central nervous system injury in acquired immune deficiency syndrome (AIDS).

TNFα has also been implicated as a key mediator of allograft rejection and graft versus host disease (GVHD) and in mediating an adverse reaction that has been observed when the rat antibody OKT3, directed against the T cell receptor CD3 complex, is used to inhibit rejection of renal transplants.

TNFα has been implicated in inducing cachexia, stimulating tumor growth, enhancing metastatic potential and mediating cytotoxicity in malignancies.

Pulmonary disorders are also linked to TNFα. For instance, TNFα plays a role in adult respiratory distress syndrome (ARDS), including stimulating leukocyte-endothelial activation, directing cytotoxicity to pneumocytes and inducing vascular leakage syndrome. The compositions of the invention can be used to treat various pulmonary disorders, including adult respiratory distress syndrome, shock lung, chronic pulmonary inflammatory disease, pulmonary sarcoidosis, pulmonary fibrosis, silicosis, idiopathic interstitial lung disease and chronic obstructive airway disorders. Examples of chronic obstructive airway disorders include asthma and Chronic Obstructive Pulmonary Disease (COPD).

Inflammatory bowel disorders including Crohn's disease are also associated with TNF. Examples of Crohn's disease-related disorders include fistulas in the bladder, vagina, and skin; bowel obstructions; abscesses; nutritional deficiencies; complications from corticosteroid use; inflammation of the joints; erythem nodosum; pyoderma gangrenosum; and lesions of the eye.

TNFα plays a role in cardiac or coronary disorders, including ischemia of the heart. A cardiac disorder in which TNFα activity is detrimental is intended to include coronary and cardiovascular diseases in which the presence of TNFα in a subject suffering from the disorder has been shown to be or is suspected of being either responsible for the pathophysiology of the disorder or a factor that contributes to a worsening of the disorder, including cardiovascular disorders, e.g., restenosis. These disorders refer to any disease, disorder, or state involving the cardiovascular system, e.g., the heart, the blood vessels, and/or the blood. Examples of a cardiovascular disorder include, but are not limited to, coronary artery disease, angina pectoris, myocardial infarction, cardiovascular tissue damage caused by cardiac arrest, cardiovascular tissue damage caused by cardiac bypass, cardiogenic shock, and hypertension, atherosclerosis, coronary artery spasm, coronary artery disease, valvular disease, arrhythmias, and cardiomyopathies.

Inflammatory diseases such as spondyloarthropathies are also aggravated by TNFα. Spondyloarthropathy refers to any one of several diseases affecting the joints of the spine, wherein such diseases share common clinical, radiological, and histological features.

Metabolic disorders, such as diabetes and obesity have been linked to TNFα. The term metabolic disorder refers to diseases or disorders which affect how the body processes substances needed to carry out physiological functions. Examples of diabetes include type 1 diabetes mellitus, type 2 diabetes mellitus, diabetic neuropathy, peripheral neuropathy, diabetic retinopathy, diabetic ulcerations, retinopathy ulcerations, diabetic macrovasculopathy, and obesity.

TNFα has been implicated in the development of anemias. An anemia is an abnormally low number of circulating red cells or a decreased concentration of hemoglobin in the blood. Examples of anemia related to rheumatoid arthritis include, for example, anemia of chronic disease, iron deficiency anemia, and autoimmune hemolytic anemia.

TNFα has also been implicated in a wide variety of pain syndromes. The term "pain" as used herein, refers to all types of pain including acute and chronic pains, such as neuropathic pain and post-operative pain, chronic lower back pain, cluster headaches, herpes neuralgia, phantom limb pain, central pain, dental pain, opioid-resistant pain, visceral pain, surgical pain, bone injury pain, pain during labor and delivery, pain resulting from burns, including sunburn, post-partum pain, migraine, angina pain, and genitourinary tract-related pain including cystitis. The term also includes nociceptive pain or nociception.

Hepatic disorders are also associated with TNFα. Hepatic disorders include diseases and other disorders of the liver or conditions associated with hepatocellular injury or a biliary tract disorders in which the presence of TNFα in a subject suffering from the disorder has been shown to be or is suspected of being either responsible for the pathophysiology of the disorder or a factor that contributes to a worsening of the disorder. Hepatic disorders include disorders associated with hepatocellular injuries, including alcoholic cirrhosis, α1 antitrypsin deficiency, autoimmune cirrhosis, cryptogenic cirrhosis, fulminant hepatitis, hepatitis B and C, and steatohepatitis. Examples of biliary tract disorders include cystic fibrosis, primary biliary cirrhosis, sclerosing cholangitis and biliary obstruction TNFα has been implicated in skin and nail disorders. A skin disorder refers to abnormalities, other than injury wounds, of the skin involving inflammation. Examples of skin disorders include, but are not limited to, psoriasis, pemphigus vulgaris, scleroderma, atopic dermatitis, sarcoidosis, erythema nodosum, hidradenitis suppurative, lichen planus, Sweet's syndrome, and vitiligo.

TNFα has been implicated in vasculitides, a group of disorders which are characterized by the inflammation of blood vessels. Examples of vasculitides in which TNFα activity is detrimental, include but are not limited to Behcet's disease, large vessel diseases such as giant cell arteritis, polymyalgia rheumatica, and Takayasu's disease or arteritis, medium vessel diseases such as classic polyarteritis *nodosa* and Kawasaki's disease or small vessel diseases such as Behcet's Syndrome, Wegner's granulomatosis, microscopic polyangitis, hypersensitivity vasculitis, small vessel vasculitis, Henoch-Schonlein purpura, allergic granulamotosis and vasculitis, and isolated central nervous system vasculitis, and thromboangitis obliterans.

Various other disorders in which TNFα activity is detrimental include but are not limited to juvenile arthritis, endometriosis, prostatitis, choroidal neovascularization, sciatica, Sjogren's Syndrome, uveitis, wet macular degeneration, osteoporosis, osteoarthritis, inflammatory bone disorders, bone resorption disease, coagulation disturbances, burns, reperfusion injury, keloid formation, scar tissue formation, pyrexia, periodontal disease, obesity, radiation toxicity, age-related cachexia, Alzheimer's disease, brain edema, inflammatory brain injury, cancer, chronic fatigue syndrome, dermatomyositis, drug reactions, such as Stevens-Johnson syndrome and Jarisch-Herxheimer reaction, edema in and/or around the spinal cord, familial periodic fevers, Felty's syndrome, fibrosis, glomerulonephritides (e.g. post-streptococcal glomerulonephritis or IgA nephropathy), loosening of prostheses, microscopic polyangiitis, mixed connective tissue disorder, multiple myeloma, cancer and cachexia, multiple organ disorder, myelo dysplastic syndrome, orchitism osteolysis, pancreatitis, including acute, chronic, and pancreatic abscess, polymyositis, progressive renal failure, pseudogout, pyoderma gangrenosum, relapsing polychondritis, rheumatic heart disease, sarcoidosis, sclerosing cholangitis, stroke, thoracoabdominal aortic aneurysm repair (TAAA), TNF receptor associated periodic syndrome (TRAPS), symptoms related to Yellow Fever vaccination, inflammatory diseases associated with the ear, chronic ear inflammation, chronic otitis media with or without cholesteatoma, pediatric ear inflammation, myotosis, ovarian cancer, colorectal cancer, therapy associated with induced inflammatory syndrome (e.g., syndromes following IL-2 administration), and disorders associated with a reperfusion injury.

The oligonucleotides may be administered alone or in conjunction with another therapeutic agent for the treatment of a TNFα disorder. Nonlimiting examples of therapeutic agents with which the TNFα inhibitor of the invention can be combined include the following: non-steroidal anti-inflammatory drug(s) (NSAIDs); cytokine suppressive anti-inflammatory drug(s) (CSAIDs); CDP-571/BAY-10-3356 (humanized anti-TNFα antibody; Celltech/Bayer); cA2/infliximab (chimeric anti-TNFα antibody; Centocor); 75 kdTNFR-IgG/etanercept (75 kD TNF receptor-IgG fusion protein; Immunex; 55 kdTNF-IgG (55 kD TNF receptor-IgG fusion protein; Hoffmann-LaRoche); IDEC-CE9/SB 210396 (non-depleting primatized anti-CD4 antibody; IDEC/SmithKline; DAB 486-IL-2 and/or DAB 389-IL-2 (IL-2 fusion proteins; Seragen; Anti-Tac (humanized anti-IL-2Rα; Protein Design Labs/Roche); IL-4 (anti-inflammatory cytokine; DNAX/Schering); IL-10 (SCH 52000; recombinant IL-10, anti-inflammatory cytokine; DNAX/Schering); IL-4; IL-10 and/or IL-4 agonists (e.g., agonist antibodies); IL-1 RA (IL-1 receptor antagonist; Synergen/Amgen); anakinra (Kineret/Amgen); TNF-bp/s-TNF (soluble TNF binding protein); R973401 (phosphodiesterase Type IV inhibitor; MK-966 (COX-2 Inhibitor; Iloprost; methotrexate; thalidomide and thalidomide-related drugs (e.g., Celgen); leflunomide (anti-inflammatory and cytokine inhibitor; tranexamic acid (inhibitor of plasminogen activation; T-614 (cytokine inhibitor; prostaglandin E1; Tenidap (non-steroidal anti-inflammatory drug; Naproxen (non-steroidal anti-inflammatory drug; Meloxicam (non-steroidal anti-inflammatory drug); Ibuprofen (non-steroidal anti-inflammatory drug); Piroxicam (non-steroidal anti-inflammatory drug); Diclofenac (non-steroidal anti-inflammatory drug); Indomethacin (non-steroidal anti-inflammatory drug); Sulfasalazine; Azathioprine; ICE inhibitor (inhibitor of the enzyme interleukin-1-beta-converting enzyme); zap-70 and/or Ick inhibitor (inhibitor of the tyrosine kinase zap-70 or Ick); VEGF inhibitor and/or VEGF-R inhibitor (inhibitors of vascular endothelial cell growth factor or vascular endothelial cell growth factor receptor; inhibitors of angiogenesis); corticosteroid anti-inflammatory drugs (e.g., SB203580); TNF-convertase inhibitors; anti-IL-12 antibodies; anti-IL-18 antibodies; interleukin-11; interleukin-13; interleukin-17 inhibitors; gold; penicillamine; chloroquine; hydroxychloroquine; chlorambucil; cyclosporine; cyclophosphamide; total lymphoid irradiation; anti-thymocyte globulin; anti-CD4 antibodies; CD5-toxins; orally-administered peptides and collagen; lobenzarit disodium; Cytokine Regulating Agents (CRAs) HP228 and HP466 (Houghten Pharmaceuticals, Inc.); ICAM-1 antisense phosphorothioate oligodeoxynucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline; anti-IL2R antibodies; marine and botanical lipids (fish and plant seed fatty acids; auranofin; phenylbutazone; meclofenamic acid; flufenamic acid; intravenous immune globulin; zileuton; azaribine; mycophenolic acid (RS-61443); tacrolimus (FK-506); sirolimus (rapamycin); amiprilose (therafectin); cladribine (2-chlorodeoxyadenosine); methotrexate; antivirals; and immune modulating agents.

Toxicity and efficacy of the prophylactic and/or therapeutic protocols of the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography. A number of studies have examined the optimal dosages for antisense oligonucleotides.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein.

Subject doses of the compounds described herein typically range from about 0.1 μg to 10,000 mg, more typically from about 1 μg/day to 8000 mg, and most typically from about 10 μg to 100 μg. Stated in terms of subject body weight, typical dosages range from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. The absolute amount will depend upon a variety of factors including the concurrent treatment, the number of doses and the individual patient parameters including age, physical condition, size and weight. These are factors well known to those of ordinary skill in the art and can be addressed with no more than routine experimentation. It is preferred generally that a maximum dose be used, that is, the highest safe dose according to sound medical judgment.

Multiple doses of the molecules of the invention are also contemplated. In some instances, when the molecules of the invention are administered with another therapeutic, for instance, an anti-inflammatory agent, a sub-therapeutic dosage of either the molecules or the other agent, or a sub-therapeutic dosage of both, is used in the treatment of a subject having, or at risk of developing a TNFα disorder. When the two classes of drugs are used together, the other agent may be administered in a sub-therapeutic dose to produce a desirable therapeutic result. A "sub-therapeutic dose" as used herein refers to a dosage which is less than that dosage which would produce a therapeutic result in the subject if administered in the absence of the other agent. Thus, the sub-therapeutic dose of a therapeutic agent is one which would not produce the desired therapeutic result in the subject in the absence of the administration of the molecules of the invention. Therapeutic doses of agents useful for treating TNFα disorders are well known in the field of medicine. These dosages have been extensively described in references such as Remington's Pharmaceutical Sciences; as well as many other medical references relied upon by the medical profession as guidance for the treatment of infectious disease, cancer, and autoimmune disease. Therapeutic dosages of oligonucleotides have also been described in the art.

Dosing regimens may be several times a day, daily, every other day, weekly, biweekly any of the times there between or less frequently. The term "biweekly dosing" as used herein, refers to the time course of administering a substance (e.g., an anti-TNFα nucleic acid) to a subject once every two weeks. The oligonucleotides may be administered every 7-20 days, every 11-17 days, or every 13-15 days, for example.

The oligonucleotides are administered in effective amounts. The effective amount of a compound of the invention in the treatment of a disease described herein may vary depending upon the specific compound used, the mode of delivery of the compound, and whether it is used alone or in combination. The effective amount for any particular application can also vary depending on such factors as the disease being treated, the particular compound being administered, the size of the subject, or the severity of the disease or condition. One of ordinary skill in the art can empirically determine the effective amount of a particular molecule of the invention without necessitating undue experimentation. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject.

The oligonucleotides described herein can be used alone or in conjugates with other molecules such as detection or cytotoxic agents in the detection and treatment methods of the invention, as described in more detail herein.

The oligonucleotide may be, for instance, coupled or conjugated to a detectable label. A detectable label is a moiety, the presence of which can be ascertained directly or indirectly. Generally, detection of the label involves an emission of energy by the label. The label can be detected directly by its ability to emit and/or absorb photons or other atomic particles of a particular wavelength (e.g., radioactivity, luminescence, optical or electron density, etc.). A label can be detected indirectly by its ability to bind, recruit and, in some cases, cleave another moiety which itself may emit or absorb light of a particular wavelength (e.g., epitope tag such as the FLAG epitope, enzyme tag such as horseradish peroxidase, etc.). An example of indirect detection is the use of a first enzyme label which cleaves a substrate into visible products. The label may be of a chemical, peptide or nucleic acid molecule nature although it is not so limited. Other detectable labels include radioactive isotopes such as $P^{32}$ or $H^3$, luminescent markers such as fluorochromes, optical or electron density markers, etc., or epitope tags such as the FLAG epitope or the HA epitope, biotin, avidin, and enzyme tags such as horseradish peroxidase, β-galactosidase, etc. The label may be bound to an oligonucleotide during or following its synthesis. There are many different labels and methods of labeling known to those of ordinary skill in the art. Examples of the types of labels that can be used in the present invention include enzymes, radioisotopes, fluorescent compounds, colloidal metals, chemiluminescent compounds, and bioluminescent compounds. Those of ordinary skill in the art will know of other suitable labels for the oligonucleotides described herein, or will be able to ascertain such, using routine experimentation. Furthermore, the coupling or conjugation of these labels to the oligonucleotides of the invention can be performed using standard techniques common to those of ordinary skill in the art.

Conjugation of the oligonucleotides to a detectable label facilitates, among other things, the use of such agents in diagnostic assays. Another category of detectable labels includes diagnostic and imaging labels (generally referred to as in vivo detectable labels) such as for example magnetic resonance imaging (MRI): Gd(DOTA); for nuclear medicine: $^{201}$Tl, gamma-emitting radionuclide 99mTc; for positron-emission tomography (PET): positron-emitting isotopes, (18)F-fluorodeoxyglucose ((18)FDG), (18)F-fluoride, copper-64, gadodiamide, and radioisotopes of Pb(II) such as 203Pb; 111In. In such instances, the use of the oligonucleotide could be observed as the oligonucleotide provides an antisense effect.

The conjugations or modifications described herein employ routine chemistry, which chemistry does not form a part of the invention and which chemistry is well known to those skilled in the art of chemistry. The use of protecting groups and known linkers such as mono- and hetero-bifunctional linkers are well documented in the literature and will not be repeated here.

As used herein, "conjugated" means two entities stably bound to one another by any physiochemical means. It is important that the nature of the attachment is such that it does not impair substantially the effectiveness of either entity. Keeping these parameters in mind, any covalent or non-covalent linkage known to those of ordinary skill in the art may be employed. In some embodiments, covalent linkage is preferred. Noncovalent conjugation includes hydrophobic interactions, ionic interactions, high affinity interactions such as biotin-avidin and biotin-streptavidin complexation and other affinity interactions. Such means and methods of attachment are well known to those of ordinary skill in the art. A variety of methods may be used to detect the label, depending on the nature of the label and other assay components.

Pharmaceutical compositions of the present invention comprise an effective amount of one or more agents, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. Moreover, for animal (e.g., human) administration, it will be understood that preparations should meet sterility, pyrogenicity, general safety and purity standards as required by FDA Office of Biological Standards. The compounds are generally suitable for administration to humans. This term requires that a compound or composition be nontoxic and sufficiently pure so that no further manipulation of the compound or composition is needed prior to administration to humans.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences (1990), incorporated herein by reference). Except insofar as any conventional carrier is incompatible with the active ingredient, its use in the therapeutic or pharmaceutical compositions is contemplated.

The agent may comprise different types of carriers depending on whether it is to be administered in solid, liquid or aerosol form, and whether it need to be sterile for such routes of administration as injection. The present invention can be administered intravenously, intradermally, intraarterially, intralesionally, intratumorally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in creams, in lipid compositions (e.g., liposomes), or by other method or any combination of the forgoing as would be known to one of ordinary skill in the art (see, for example, Remington's Pharmaceutical Sciences, incorporated herein by reference). In a particular embodiment, intraperitoneal injection is contemplated.

In any case, the composition may comprise various antioxidants to retard oxidation of one or more components. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The agent may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups also can be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

The compounds of the invention may be administered directly to a tissue. Direct tissue administration may be achieved by direct injection. The compounds may be administered once, or alternatively they may be administered in a plurality of administrations. If administered multiple times, the compounds may be administered via different routes. For example, the first (or the first few) administrations may be made directly into the affected tissue while later administrations may be systemic.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

According to the methods of the invention, the compound may be administered in a pharmaceutical composition. In general, a pharmaceutical composition comprises the compound of the invention and a pharmaceutically-acceptable carrier. As used herein, a pharmaceutically-acceptable carrier means a non-toxic material that does not interfere with the effectiveness of the biological activity of the active ingredients.

Pharmaceutically acceptable carriers include diluents, fillers, salts, buffers, stabilizers, solubilizers and other materials which are well-known in the art. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The compounds of the invention may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. Techniques for preparing aerosol delivery systems are well known to those of skill in the art. Generally, such systems should utilize components which will not significantly impair the biological properties of the active agent (see, for example, Sciarra and Cutie, "Aerosols," in Remington's Pharmaceutical Sciences. Those of skill in the art can readily determine the various parameters and conditions for producing aerosols without resort to undue experimentation.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

The compositions of the invention may be formulated in a topical composition for administration to the skin or a body cavity. Suitable topical vehicles and vehicle components are well known in the cosmetic and pharmaceutical arts, and include such vehicles (or vehicle components) as water; organic solvents such as alcohols (particularly lower alcohols readily capable of evaporating from the skin such as ethanol), glycols (such as propylene glycol, butylene glycol, and glycerin), aliphatic alcohols (such as lanolin); mixtures of water and organic solvents (such as water and alcohol), and mixtures of organic solvents such as alcohol and glycerin (optionally also with water); lipid-based materials such as fatty acids, acylglycerols (including oils, such as mineral oil, and fats of natural or synthetic origin), phosphoglycerides, sphingolipids and waxes; protein-based materials such as collagen and gelatin; silicone-based materials (both non-volatile and volatile) such as cyclomethicone, demethiconol and dimethicone copolyol (Dow Corning); hydrocarbon-based materials such as petrolatum and squalane; anionic, cationic and amphoteric surfactants and soaps; sustained-release vehicles such as microsponges and polymer matrices; stabilizing and suspending agents; emulsifying agents; and other vehicles and vehicle components that are suitable for administration to the skin, as well as mixtures of topical vehicle components as identified above or otherwise known to the art. The vehicle may further include components adapted to improve the stability or effectiveness of the applied formulation, such as preservatives, antioxidants, skin penetration enhancers, sustained release materials, and the like. Examples of such vehicles and vehicle components are well known in the art and are described in such reference works as Martindale—The Extra Pharmacopoeia (Pharmaceutical Press, London 1993) and Martin (ed.), Remington's Pharmaceutical Sciences.

The choice of a suitable vehicle will depend on the particular physical form and mode of delivery that the formulation is to achieve. Examples of suitable forms include liquids (e.g., gargles and mouthwashes, including dissolved forms of the strontium cation as well as suspensions, emulsions and the like); solids and semisolids such as gels, foams, pastes, creams, ointments, "sticks" (as in lipsticks or underarm deodorant sticks), powders and the like; formulations containing liposomes or other delivery vesicles; rectal or vaginal suppositories, creams, foams, gels or ointments; and other forms. Typical modes of delivery include application using the fingers; application using a physical applicator such as a cloth, tissue, swab, stick or brush (as achieved for example by soaking the applicator with the formulation just prior to application, or by applying or adhering a prepared applicator already containing the formulation—such as a treated or premoistened bandage, wipe, washcloth or stick—to the skin); spraying (including mist, aerosol or foam spraying); dropper application (as for example with ear drops); sprinkling (as with a suitable powder form of the formulation); and soaking.

Topical formulations also include formulations for rectal and vaginal administration. Formulations for rectal administration may be presented as a suppository with a suitable base comprising, for example, cocoa butter. Formulations suitable for vaginal administration may be presented as tablets, pessaries, tampons, creams, gels, pastes, foams or spray formulations containing in addition to the active ingredient such carriers as are known in the art to be appropriate.

In yet other embodiments, a delivery vehicle is a biocompatible microparticle or implant that is suitable for implantation into the mammalian recipient. Other delivery systems can include time-release, delayed release or sustained release delivery systems. Such systems can avoid repeated administrations of the compound, increasing convenience to the subject and the physician. Many types of release delivery systems are available and known to those of ordinary skill in the art. They include polymer base systems such as poly (lactide-glycolide), copolyoxalates, polycaprolactones, polyesteramides, polyorthoesters, polyhydroxybutyric acid, and polyanhydrides.

In some embodiments the antisense nucleic acids of the invention are formulated as a stable self-assembling nanostructure. The nanostructure includes a TNFα antisense oligonucleotide, wherein the antisense oligonucleotide is associated with a core. The core may be a solid or a hollow core, such as a liposomal core. A solid core is a spherical shaped material that does not have a hollow center. The term spherical as used herein refers to a general shape and does not imply or is not limited to a perfect sphere or round shape. It may include imperfections.

Solid cores can be constructed from a wide variety of materials known to those skilled in the art including but not limited to: noble metals (gold, silver), transition metals (iron, cobalt) and metal oxides (silica). In addition, these cores may be inert, paramagnetic, or superparamagnetic. These solid cores can be constructed from either pure compositions of described materials, or in combinations of mixtures of any number of materials, or in layered compositions of materials. In addition, solid cores can be composed of a polymeric core such as amphiphilic block copolymers, hydrophobic polymers such as polystyrene, poly(lactic acid), poly(lactic co-glycolic acid), poly(glycolic acid), poly (caprolactone) and other biocompatible polymers known to those skilled in the art.

The core may alternatively be a hollow core, which has at least some space in the center region of a shell material. Hollow cores include liposomal cores. A liposomal core as used herein refers to a centrally located core compartment formed by a component of the lipids or phospholipids that form a lipid bilayer. "Liposomes" are artificial, self closed vesicular structure of various sizes and structures, where one or several membranes encapsulate an aqueous core. Most typically liposome membranes are formed from lipid bilayers membranes, where the hydrophilic head groups are oriented towards the aqueous environment and the lipid chains are embedded in the lipophilic core. Liposomes can be formed as well from other amphiphilic monomeric and polymeric molecules, such as polymers, like block copolymers, or polypeptides. Unilamellar vesicles are liposomes defined by a single membrane enclosing an aqueous space. In contrast, oligo- or multilamellar vesicles are built up of several membranes. Typically, the membranes are roughly 4 nm thick and are composed of amphiphilic lipids, such as phospholipids, of natural or synthetic origin. Optionally, the membrane properties can be modified by the incorporation of other lipids such as sterols or cholic acid derivatives.

The lipid bilayer is composed of two layers of lipid molecules. Each lipid molecule in a layer is oriented substantially parallel to adjacent lipid bilayers, and two layers that form a bilayer have the polar ends of their molecules exposed to the aqueous phase and the non-polar ends adjacent to each other. The central aqueous region of the liposomal core may be empty or filled fully or partially with water, an aqueous emulsion, oligonucleotides, or other therapeutic or diagnostic agents.

"Lipid" refers to its conventional sense as a generic term encompassing fats, lipids, alcohol-ether-soluble constituents of protoplasm, which are insoluble in water. Lipids usually consist of a hydrophilic and a hydrophobic moiety. In water lipids can self organize to form bilayers membranes, where the hydrophilic moieties (head groups) are oriented towards the aqueous phase, and the lipophilic moieties (acyl chains) are embedded in the bilayers core. Lipids can comprise as well two hydrophilic moieties (bola amphiphiles). In that case, membranes may be formed from a single lipid layer, and not a bilayer. Typical examples for lipids in the current context are fats, fatty oils, essential oils, waxes, steroid, sterols, phospholipids, glycolipids, sulpholipids, aminolipids, chromolipids, and fatty acids. The term encompasses both naturally occurring and synthetic lipids. Preferred lipids in connection with the present invention are: steroids and sterol, particularly cholesterol, phospholipids, including phosphatidyl, phosphatidylcholines and phosphatidylethanolamines and sphingomyelins. Where there are fatty acids, they could be about 12-24 carbon chains in length, containing up to 6 double bonds. The fatty acids are linked to the backbone, which may be derived from glycerol. The fatty acids within one lipid can be different (asymmetric), or there may be only 1 fatty acid chain present, e.g. lysolecithins. Mixed formulations are also possible, particularly when the non-cationic lipids are derived from natural sources, such as lecithins (phosphatidylcholines) purified from egg yolk, bovine heart, brain, liver or soybean.

The liposomal core can be constructed from one or more lipids known to those in the art including but not limited to: sphingolipids such as sphingosine, sphingosine phosphate, methylated sphingosines and sphinganines, ceramides, ceramide phosphates, 1-0 acyl ceramides, dihydroceramides, 2-hydroxy ceramides, sphingomyelin, glycosylated sphingolipids, sulfatides, gangliosides, phosphosphingolipids, and phytosphingosines of various lengths and saturation states and their derivatives, phospholipids such as phosphatidylcholines, lysophosphatidylcholines, phosphatidic acids, lysophosphatidic acids, cyclic LPA, phosphatidylethanolamines, lysophosphatidylethanolamines, phosphatidylglycerols, lysophosphatidylglycerols, phosphatidylserines, lysophosphatidylserines, phosphatidylinositols, inositol phosphates, LPI, cardiolipins, lysocardiolipins, bis(monoacylglycero) phosphates, (diacylglycero) phosphates, ether lipids, diphytanyl ether lipids, and plasmalogens of various lengths, saturation states, and their derivatives, sterols such as cholesterol, desmosterol, stigmasterol, lanosterol, lathosterol, diosgenin, sitosterol, zymosterol, zymostenol, 14-demethyl-lanosterol, cholesterol sulfate, DHEA, DHEA sulfate, 14-demethyl-14-dehydrlanosterol, sitostanol, campesterol, ether anionic lipids, ether cationic lipids, lanthanide chelating lipids, A-ring substituted oxysterols, B-ring substituted oxysterols, D-ring substituted oxysterols, side-chain substituted oxysterols, double substituted oxysterols, cholestanoic acid derivatives, fluorinated sterols, fluorescent sterols, sulfonated sterols, phosphorylated sterols, and polyunsaturated sterols of different lengths, saturation states, and their derivatives.

The oligonucleotides may be positioned on the exterior of the core, within the walls of the core and/or in the center of the core. An oligonucleotide that is positioned on the core is typically referred to as coupled to the core. Coupled may be direct or indirect. In some embodiments at least 25, 50, 75, 100, 200, 300, 400, 500, 600, 700, 800, 900 or 1,000 oligonucleotides or any range combination thereof are on the exterior of the core. In some embodiments, 1-1000, 10-500, 50-250, or 50-300 oligonucleotides are present on the surface.

The oligonucleotides of the oligonucleotide shell may be oriented in a variety of directions. In some embodiments the oligonucleotides are oriented radially outwards. The orientation of these oligonucleotides can be either 5' distal/3' terminal in relation to the core, or 3' distal/5'terminal in relation to the core, or laterally oriented around the core. In one embodiment one or a multiplicity of different oligonucleotides are present on the same surface of a single SNA. In all cases, at least 1 oligonucleotide is present on the surface but up to 10,000 can be present.

The oligonucleotides may be linked to the core or to one another and/or to other molecules such an active agents either directly or indirectly through a linker. The oligonucleotides may be conjugated to a linker via the 5' end or the 3' end, e.g. [Sequence, 5'-3']-Linker or Linker-[Sequence, 5'-3']. Some or all of the oligonucleotides of the nanostructure may be linked to one another either directly or indirectly through a covalent or non-covalent linkage. The linkage of one oligonucleotide to another oligonucleotide may be in addition to or alternatively to the linkage of that oligonucleotide to liposomal core.

The oligonucleotide shell may be anchored to the surface of the core through one or multiple of linker molecules, including but not limited to: any chemical structure containing one or multiple thiols, such as the various chain length alkane thiols, cyclic dithiol, lipoic acid, or other thiol linkers known to those skilled in the art.

In an embodiment containing a liposomal core, the oligonucleotide shell may be anchored to the surface of the liposomal core through conjugation to one or a multiplicity of linker molecules including but not limited to: tocopherols, sphingolipids such as sphingosine, sphingosine phosphate, methylated sphingosines and sphinganines, ceramides, ceramide phosphates, 1-0 acyl ceramides, dihydroceramides, 2-hydroxy ceramides, sphingomyelin, glycosylated sphingolipids, sulfatides, gangliosides, phosphosphingolipids, and phytosphingosines of various lengths and saturation states and their derivatives, phospholipids such as phosphatidylcholines, lysophosphatidylcholines, phosphatidic acids, lysophosphatidic acids, cyclic LPA, phosphatidylethanolamines, lysophosphatidylethanolamines, phosphatidylglycerols, lysophosphatidylglycerols, phosphatidylserines, lysophosphatidylserines, phosphatidylinositols, inositol phosphates, LPI, cardiolipins, lysocardiolipins, bis(monoacylglycero) phosphates, (diacylglycero) phosphates, ether lipids, diphytanyl ether lipids, and plasmalogens of various lengths, saturation states, and their derivatives, sterols such as cholesterol, desmosterol, stigmasterol, lanosterol, lathosterol, diosgenin, sitosterol, zymosterol, zymostenol, 14-demethyl-lanosterol, cholesterol sulfate, DHEA, DHEA sulfate, 14-demethyl-14-dehydrlanosterol, sitostanol, campesterol, ether anionic lipids, ether cationic lipids, lanthanide chelating lipids, A-ring substituted oxysterols, B-ring substituted oxysterols, D-ring substituted oxysterols, side-chain substituted oxysterols, double substituted oxysterols, cholestanoic acid derivatives, fluorinated sterols, fluorescent sterols, sulfonated sterols, phosphorylated sterols, and polyunsaturated sterols of different lengths, saturation states, and their derivatives.

The oligonucleotide may also be associated with the core by being embedded within the core (liposomal core) or it may be attached or linked, either indirectly (i.e. non-covalently or covalently through other molecules such a linkers) or directly (i.e. covalently).

The invention also includes articles, which refers to any one or collection of components. In some embodiments the articles are kits. The articles include pharmaceutical or diagnostic grade compounds of the invention in one or more containers. The article may include instructions or labels promoting or describing the use of the compounds of the invention.

As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention in connection with treatment of TNFα disorders.

"Instructions" can define a component of promotion, and typically involve written instructions on or associated with packaging of compositions of the invention. Instructions also can include any oral or electronic instructions provided in any manner.

Thus the agents described herein may, in some embodiments, be assembled into pharmaceutical or diagnostic or research kits to facilitate their use in therapeutic, diagnostic or research applications. A kit may include one or more containers housing the components of the invention and instructions for use. Specifically, such kits may include one or more agents described herein, along with instructions describing the intended therapeutic application and the proper administration of these agents. In certain embodiments agents in a kit may be in a pharmaceutical formulation and dosage suitable for a particular application and for a method of administration of the agents.

The kit may be designed to facilitate use of the methods described herein by physicians and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for human administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The compositions of the kit may be provided as any suitable form, for example, as liquid solutions or as dried powders. When the composition provided is a dry powder, the powder may be reconstituted by the addition of a suitable solvent, which may also be provided. In embodiments where liquid forms of the composition are sued, the liquid form may be concentrated or ready to use. The solvent will depend on the compound and the mode of use or administration. Suitable solvents for drug compositions are well known and are available in the literature. The solvent will depend on the compound and the mode of use or administration.

The kits, in one set of embodiments, may comprise a carrier means being compartmentalized to receive in close confinement one or more container means such as vials, tubes, and the like, each of the container means comprising one of the separate elements to be used in the method. For example, one of the containers may comprise a positive control for an assay. Additionally, the kit may include containers for other components, for example, buffers useful in the assay.

The present invention also encompasses a finished packaged and labeled pharmaceutical product. This article of manufacture includes the appropriate unit dosage form in an appropriate vessel or container such as a glass vial or other container that is hermetically sealed. In the case of dosage forms suitable for parenteral administration the active ingredient is sterile and suitable for administration as a particulate free solution. In other words, the invention encompasses both parenteral solutions and lyophilized powders, each being sterile, and the latter being suitable for reconstitution prior to injection. Alternatively, the unit dosage form may be a solid suitable for oral, transdermal, topical or mucosal delivery.

In a preferred embodiment, the unit dosage form is suitable for intravenous, intramuscular or subcutaneous delivery. Thus, the invention encompasses solutions, preferably sterile, suitable for each delivery route.

As with any pharmaceutical product, the packaging material and container are designed to protect the stability of the product during storage and shipment. Further, the products of the invention include instructions for use or other informational material that advise the physician, technician or patient on how to appropriately prevent or treat the TNFα disease or disorder. In other words, the article of manufacture includes instruction means indicating or suggesting a dosing regimen including, but not limited to, actual doses, monitoring procedures and other monitoring information.

More specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material. The invention also provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material. The invention further provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material. The invention further provides an article of manufacture comprising a needle or syringe, preferably packaged in sterile form, for injection of the formulation, and/or a packaged alcohol pad.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

EXAMPLES

Example 1: Inhibitory Oligonucleotide Sequences

Oligonucleotides were synthesized on a MerMade 48 (Bioautomation) using standard phosphoramidite chemistry (reagents from Glen Research and ChemGenes). Three of the sequences were targeted to the start codon of human TNF mRNA (Oligos 3482, 3483, and 3484). Three additional sequences were generated with Sfold (Oligos 3485, 3486, and 3487). One sequence, Oligo 3488, was humanized. Finally, a scrambled control was generated (Oligo 3495). The respective sequences are listed in Table 1:

TABLE 1

List of Oligonucleotide Sequences

| Oligo ID | Oligo Sequence (5' to 3') | SEQ ID NO. |
|---|---|---|
| Oligo 3482 | CATGGTGTCCTTTCCAGG | 1 |
| Oligo 3483 | TCAGTGCTCATGGTGTCC | 2 |
| Oligo 3484 | CATGCTTTCAGTGCTCAT | 3 |
| Oligo 3485 | TGGGAGTAGATGAGGTAC | 4 |
| Oligo 3486 | TTGACCTTGGTCTGGTAG | 5 |
| Oligo 3487 | GATGGCAGAGAGGAGGTT | 6 |
| Oligo 3488 | TTATCTCTCAGCTCCACG | 7 |
| Oligo 3495 | ATGGAGCAAAACCCGCAG | 8 |

The oligonucleotides were then purified with reverse phase high performance liquid chromatography (Aglient). The oligonucleotide product identity was verified with matrix-assisted laser desorption ionization mass spectrometry.

The synthesized oligonucleotides were initially screened for TNF expression. Primary human keratinocytes were plated in 96 well plates. The following day, the cells were transfected with 2 µM of the antisense strand using lipofectamine (Life Technologies) in Optimem (Life Technologies) for 24 hours. After the incubation period, the cells were washed with PBS, their mRNA extracted, cDNA synthesized, and TNF and GAPDH levels were determined with RT-PCR (FIG. 1). Oligonucleotides 3482, 4385 and 3487 were particularly effective at decreasing TNF expression levels.

Figure 2:
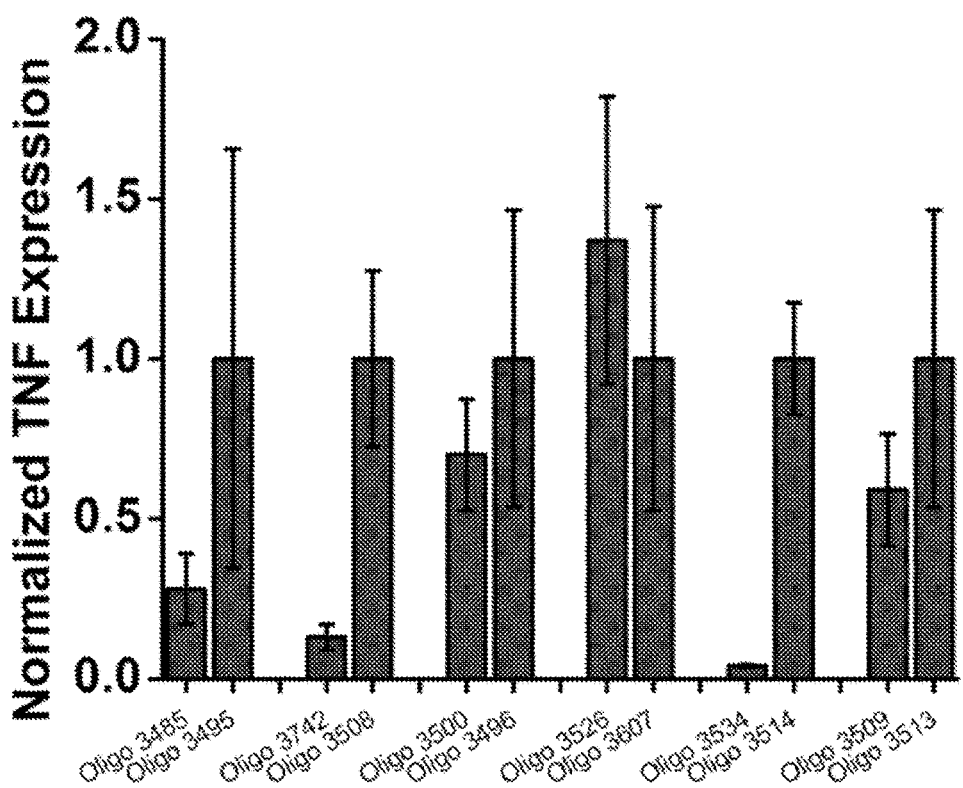
FIG. 2 is a bar graph showing inhibitory activity in primary human keratinocytes of several oligonucleotides including Oligo 3485, 3472, 3508, 3500, 3496, 3526, 3607, 3534, 3514, 3509, 3516 and 3495 on TNF expression.

The same experimental conditions were performed in an additional set of modified sequences. In brief, primary human keratinocytes were plated in 96 well plates. The following day, the cells were transfected with 2 µM of the antisense strand using lipofectamine (Life Technologies) in Optimem (Life Technologies) for 24 hours. After the incubation period, the cells were washed with PBS, their mRNA extracted, cDNA synthesized, and TNF and GAPDH levels were probed with RT-PCR (FIG. 2). Each sequence was paired with a respective control (italicized), as seen in Table 2:

TABLE 2

Modified Oligonucleotide Sequences and their Controls

| Oligo ID | Oligo Name | Oligo Sequence (5' to 3')<br>(m = methylated;<br>* = phosphorothioate linkage) | SEQ ID NO. |
| --- | --- | --- | --- |
| Oligo 3485 | hTNF 568-PO | TGGGAGTAGATGAGGTAC | 4 |
| Oligo 3495 | scr-18 PO | *ATGGAGCAAAACCCGCAG* | 8 |
| Oligo 3742 | hTNF 568-OmePO | mUmGmGmGmAmGmUmAmGmAmUmGmAmG<br>mGmUmAmC | 10 |
| Oligo 3508 | scr-18 OMePO | *mAmUmGmGmAmGmCmAmAmAmAmCmCmCmGm*<br>*CmAmG* | 11 |
| Oligo 3500 | hTNF 568-PS | T*G*G*G*A*G*T*A*G*A*T*G*A*G*G*T*A*C | 12 |
| Oligo 3496 | scr-18 PS | *A*T*G*G*A*G*C*A*A*A*A*C*C*C*G*C*A*G* | 13 |
| Oligo 3526 | hTNF 568-OmePS | mU*mG*mG*mG*mA*mG*mU*mA*mG*mA*mU*<br>mG*mA*mG*mG*mU*mA*mC | 14 |
| Oligo 3607 | scr-18 OMePS | *mA*mU*mG*mG*mA*mG*mC*mA*mA*mA*mA*m*<br>*C*mC*mC*mG*mC*mA*mG* | 15 |
| Oligo 3534 | hTNF 568-<br>Gapmer/OmePO-PS | mUmGmGmGmAmGT*A*G*A*T*G*mAmGmGm<br>UmAmC | 16 |
| Oligo 3514 | scr-18<br>gapmer/OMePO-PS | *mAmUmGmGmAmGC*A*A*A*A*C*mCmCmGmC*<br>mAmG* | 17 |
| Oligo 3509 | hTNF 568-<br>Gapmer/OmePS-PS | mU*mG*mG*mG*mA*mG*T*A*G*A*T*G*mA*<br>mG*mG*mU*mA*mC | 18 |
| Oligo 3513 | scr-18<br>gapmer/OMePS-PS | *mA*mU*mG*mG*mA*mG*C*A*A*A*A*C*mC*mC*<br>mG*mC*mA*mG* | 19 |

Example 2: Inhibition of TNF by Spherical Nucleic Acids (SNAs)

The chemistries of different SNAs were compared with respective oligonucleotide controls. SNAs containing anti-TNF antisense strands were prepared. 13±1 nm diameter gold nanoparticles were prepared by reducing a 490 mL boiling aqueous solution of 0.1969 g of HAuC14.3H2O with 0.570 g of trisodium citrate in 10 mL of water. The particle solution was then filtered through a 0.45 μm cellulose acetate membrane to remove any aggregated nanoparticles. The nanoparticle concentration was 11 nM as prepared.

The gold nanoparticles were then used as is to prepare anti-TNF and control SNAs. The SNA synthesis began by adding a thiolated 5 kDa linear poly(ethylene glycol) to the as-synthesized gold nanoparticles to a final concentration of 5 μM. After mixing, the solution was allowed to stand for 1.5 hours at 37° C., at which point the oligonucleotides were added to the solution at a final concentration of 5 μM. While maintaining the temperature, a solution of sodium chloride was added to the functionalization mixture in two equal aliquots over the course of 1 hour to raise the concentration of NaCl to 150 mM. That mixture was allowed to stand at 37° C. overnight. The following day, centrifugation at 21,000×g precipitated the particles, the supernatant was removed, and the particles were resuspended in sterile PBS. This process was repeated three times to remove excess PEG and oligonucleotide that had not adhered to the particles. The number of oligonucleotides per nanoparticles was measured by liberating the oligonucleotides from the gold core—the nanoparticles were oxidatively dissolved with KCN. Finally, the number of oligonucleotides liberated was measured with a fluorescence based assay (Oligreen, Life Technologies) according to the manufacturer's instructions.

Figure 3:
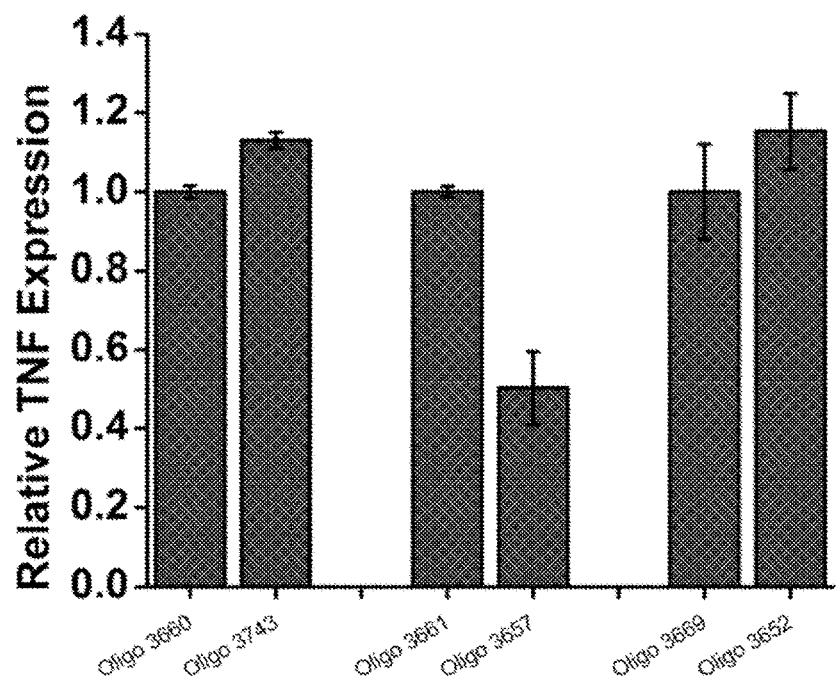
FIG. 3 is a bar graph showing the effect of various chemistries on the inhibitory activity in primary human keratinocytes of several oligonucleotides including Oligo 3660, 3743, 3661, 3657, 3669, and 3652 compared with their respective controls. The oligonucleotides were formulated as spherical nucleic acids (SNAs).

Primary human keratinocytes were plated in 96 well plates. The following day, the cells were transfected with the TNF or control SNAs at an oligonucleotide concentration of 5 μM. The treatment was allowed to proceed overnight. The following day, the cells were washed, the mRNA collected, cDNA prepared, and the expressions of TNF and GAPDH were probed. The results are shown in FIG. 3. Each sequence was paired with a respective control (italicized) as seen in Table 3:

TABLE 3

Oligonucleotide Sequences and Controls Used to Compare SNA Chemistries

| Oligo ID | Oligo Name | Oligo Sequence (5' to 3') (m = methylated; * = phosphorothioate linkage) | SEQ ID NO. |
|---|---|---|---|
| Oligo 3652 | hTNF568-Gapmer-OMePS/PS-SH | mU*mG*mG*mG*mA*mG*T*A*G*A*T*G*mA*mG*mG*mU*mA*mC*/iSp18//iSp18//3ThioMC3-D/ | 20 |
| Oligo 4030 | | mA*mU*mG*mG*mA*mG*C*A*A*A*A*C*mC*mC*mG*mC*mA*Mg/iSp18//iSp18//3ThioMC3-D/ | 21 |
| Oligo 3657 | hTNF568-Gapmer-OMePO/PS-SH | mUmGmGmGmAmGT*A*G*A*T*G*mAmGmGmUmAmC/iSp18//iSp18//3ThioMC3-D/ | 22 |
| Oligo 4028 | | mAmUmGmGmAmGC*A*A*A*A*C*mCmCmGmCmAmG/iSp18//iSp18//3ThioMC3-D/ | 23 |
| Oligo 3743 | hTNF568-PO-SH | TGGGAGTAGATGAGGTAC/iSp18//iSp18//3ThioMC3-D/ | 24 |
| Oligo 3660 | | ATGGAGCAAAACCCGCAG/iSp18//iSp18//3ThioMC3-D/ | 25 |

Figures 4A, 4B:
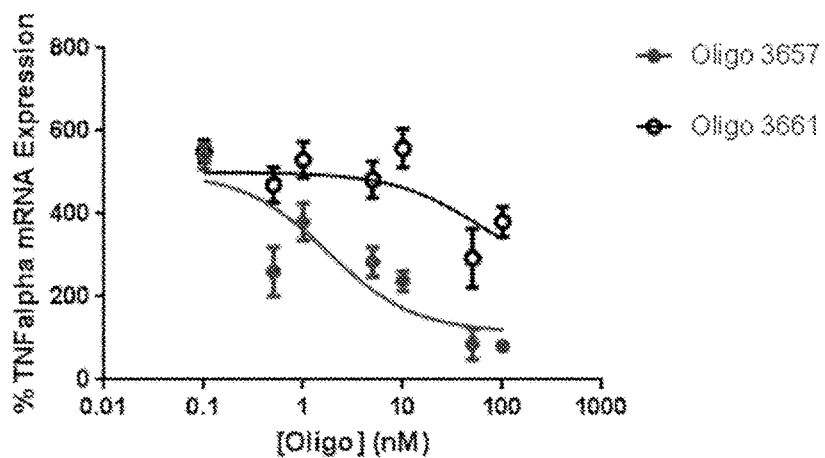
FIGS. 4A-4B show the percent gene knockdown of TNF by SNAs in stimulated human keratinocytes.

Human keratinocytes were plated in 96 well tissue culture plates and allowed to adhere overnight. The next day, they were treated with 50 ng/mL human recombinant TNF for 4 hours prior to treatment with Oligo 3661 modified SNAs or Oligo 3657 (SEQ ID NO:22) SNAs. The treatment was allowed to proceed overnight. The following day the cells were washed, the mRNA collected, cDNA prepared, and the expression of TNF and GAPDH were probed and the percent gene knockdown was calculated (FIG. 4).

Figures 5A, 5B:
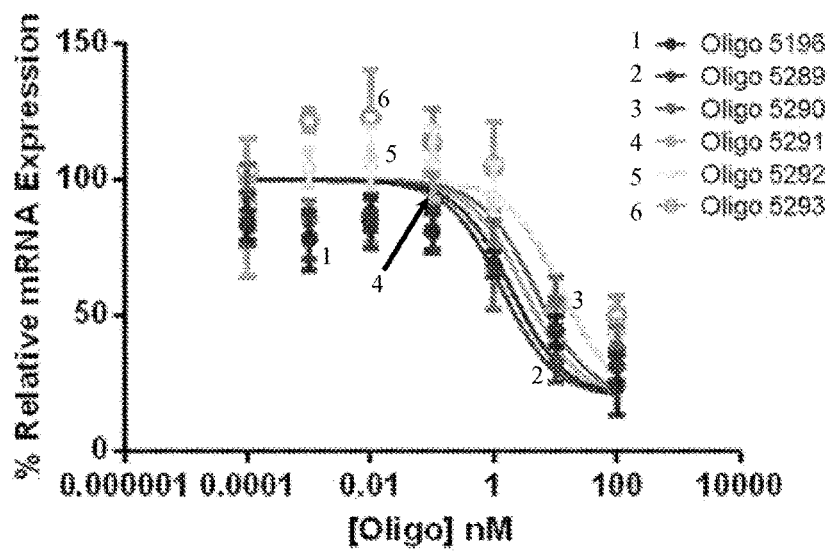
FIGS. 5A-5B show the effects of additional phosphorothioate modifications on Oligo 3657 modified SNAs.
Figures 6A, 6B:
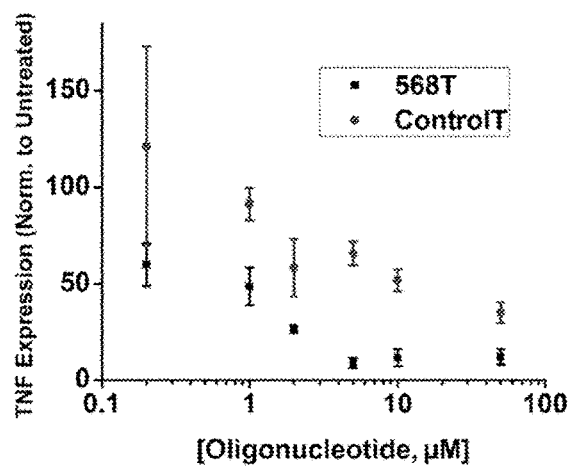
FIGS. 6A-6B show the effect of hollow SNAs on TNF expression.

The effect of additional phosphorothioate modifications on Oligo 3657-modified SNAs was examined. A family of oligonucleotides with increasing phosphorothioate content was prepared as using gold nanoparticles as previously described. The particles were transfected into human keratinocytes overnight. The following day, the cells were washed, the mRNA collected, cDNA prepared, and the expression of TNF and GAPDH were probed and the percent gene knockdown was calculated (FIG. 5). The sequences in Table 4 were analyzed:

phoramidite were prepared (reagents from ChemGenes). Liposomal scaffolds consisting of dioleoylphosphatidylcholine (DOPC) were prepared by dissolving the lipid in DCM at 75 mg/mL, and then the solution dried under a stream of nitrogen and lyophilized. The residual material was dissolved in HEPES (pH 7.3) and 150 mM NaCl at a concentration of 40 mg/mL, and allowed to stand for 30 minutes, followed by three freeze/thaw cycles using liquid nitrogen. That solution was then extruded through polycarbonate membranes containing pores with diameters of 100, 50, and 30 nm. The resultant solution contained liposomes approximately 40 nm in diameter. Functionalization into SNAs occurred by adding the tocopherol-modified oligonucleotides to the liposome solution. The materials were then concentrated with tangential flow filtration and applied to human keratinocytes as described above. The sequences prepared were as in Table 5:

TABLE 4

Oligonucleotides with Increasing Phosphorothioate Content

| Oligo ID | Oligo Name | Oligo Sequence (5' to 3') (m = methylated; * = phosphorothioate linkage) | SEQ ID NO. |
|---|---|---|---|
| Oligo 5196 | hTNF 568-1 PS | mUmGmGmGmAmG*T*A*G*A*T*G*mAmGmGmUmAmC/isp18//isp18//3thiomc3-d/ | 26 |
| Oligo 5289 | hTNF 568-2 PS | mUmGmGmGmA*mG*T*A*G*A*T*G*mAmGmGmUmAmC/isp18//isp18//3thiomc3-d/ | 27 |
| Oligo 5290 | hTNF 568-3 PS | mUmGmGmG*mA*mG*T*A*G*A*T*G*mAmGmGmUmAmC/isp18//isp18//3thiomc3-d/ | 28 |
| Oligo 5291 | hTNF 568-4 PS | mUmGmG*mA*mG*T*A*G*A*T*G*mAmGmGmUmAmC/isp18//isp18//3thiomc3-d/ | 29 |
| Oligo 5292 | hTNF 568-5 PS | mUmG*mG*mA*mG*T*A*G*A*T*G*mAmGmGmUmAmC/isp18//isp18//3thiomc3-d/ | 30 |
| Oligo 5293 | hTNF 568-6 PS | mU*mG*mG*mG*mA*mG*T*A*G*A*T*G*mAmGmGmUmAmC/isp18//isp18//3thiomc3-d/ | 31 |

The effect of hollow SNAs on TNF expression was examined. Oligonucleotides containing a tocopherol phos-

TABLE 5

Oligonucleotide Sequence and its Control for Hollow SNA Investigation

| Oligo ID | Oligo Name | Oligo Sequence (5' to 3') (m = methylated; * = phosphorothioate linkage) | SEQ ID NO |
|---|---|---|---|
| 568T | TNF568-toco | mUmGmGmGmAmGT*A*G*A*T*G*mAmGmGmUmAmC/iSp18//iSp18//toco/ | 32 |
| ControlT | Control-toco | mAmUmGmGmAmGC*A*A*A*A*C*mCmCmGmCmAmG/iSp18//iSp18//toco/ | 33 |

Example 3: The Inhibitory Effect of Antisense SNAs Targeting TNF mRNA

The inhibitory effect of antisense SNAs targeting TNF mRNA on mRNA expression was compared to non-targeting control SNAs. SNAs containing anti-TNF antisense strands, composed of compound 6081, were prepared.

All oligonucleotides were synthesized at the 1 μmole scale employing standard UniLinker (ChemGenes). The DNA, RNA, 2'-O-Me monomers and hexa(ethylene glycol) spacers were obtained from ChemGenes Corporation. The cholesterol modifier was obtained from Glen Research. Linkages were either standard phosphodiesters or phosphorothioates made with 0.2 M phenylacetyl disulfide (PADS) in 1:1 lutidine:ACN as the sulfurization agent. Synthesis was performed DMT-off, in the 5' to 3' direction. After synthesis, the oligonucleotides were cleaved from the support and de-protected using a 4:1 mixture of ammonium hydroxide and ethanol at 55° C. for 16 hours. The oligonucleotides were purified via ion-exchange high performance liquid chromatography (HPLC) techniques. Molecular weights and extinction coefficients were estimated using IDT OligoAnalyzer. Verification of oligonucleotide molecular weight was performed using matrix-assisted laser desorption/ionization (MALDI). Oligonucleotide concentration was determined by UV-absorbance at 260 nm on a microplate reader (BioTek) together with the calculated extinction coefficient from the IDT OligoAnalyzer.

The oligonucleotides were then used to prepare anti-TNF and controls SNAs. The synthesis began by diluting the oligonucleotides to 100 μM in PBS. The oligonucleotides were then stored overnight, protected from light, at 4° C. Due to the electrostatic repulsion of the polar solvent towards the hydrophobic cholesterol tail of the oligonucleotide, structured micelle structures form with a cholesterol core and oligonucleotides extending outward.

Figure 9:
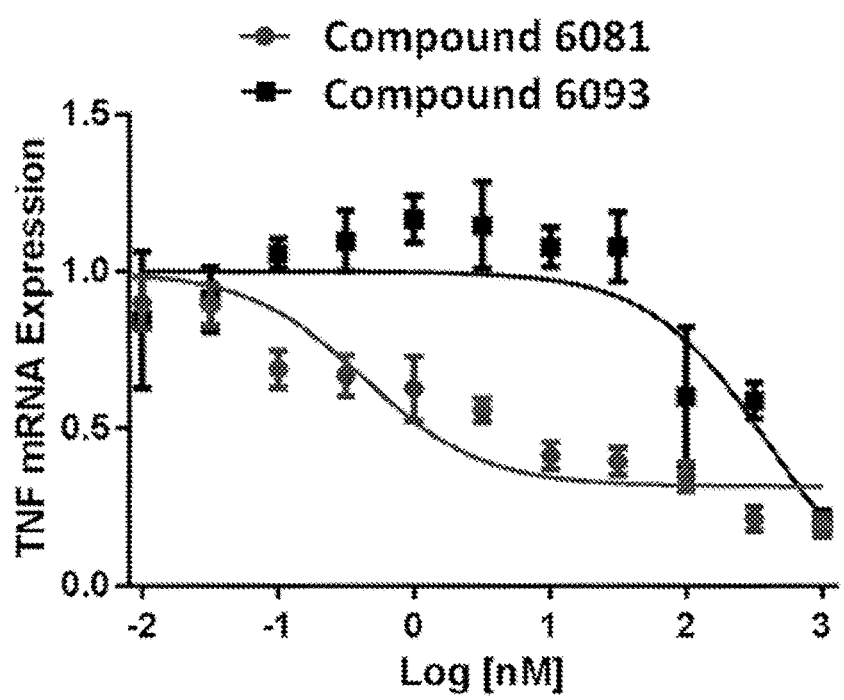
FIG. 9 shows the percent gene knockdown of TNF by SNAs in stimulated human keratinocytes. The percent TNF mRNA expression between Oligo 6081 and its control, Oligo 6093 is shown graphically. Data presented are gene expressions of TNF mRNA relative to cells stimulated with TNF alone (no oligonucleotide, set to 1.0).

Primary human keratinocytes were plated in 96 well plates. The following day, the cells were treated with 50 ng/mL human recombinant TNF for 4 hours prior to being transfected with Oligo ID 6081 or Oligo ID 6093 SNAs at oligonucleotide concentrations of 1000, 333.3, 100, 33.3, 10, 3.3, 1, 0.33, 0.1, 0.03 and 0.01 nM. The treatment was allowed to proceed overnight. The following day, the cells were washed, the mRNA collected, cDNA prepared, and the expressions of TNF and GAPDH were probed and the percent gene expression was calculated (FIG. 9).

Figure 10:
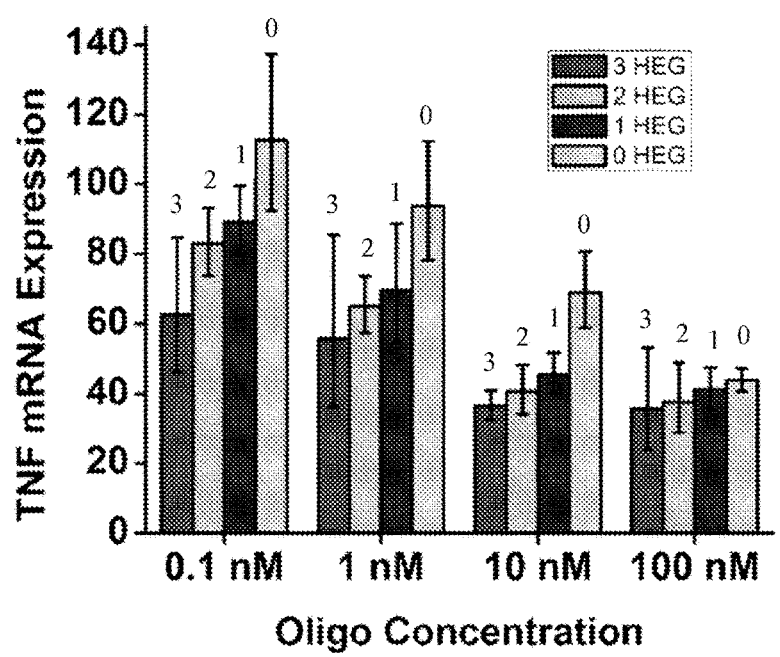
FIG. 10 is a bar graph showing the effect of various hexa(ethylene glycol) spacer lengths on the inhibitory activity of TNF mRNA expression in stimulated primary human keratinocytes. The percent TNF mRNA expression of cells treated with Oligos 6080, 6081, 6082 and 6092 and relative to their respective controls, Oligos 6083, 6093, 6094 and 6095 (set to 100) are shown.

The effect of varying the chain lengths of hexaethylene glycol (HEG) on the antisense activity of Oligo ID 6081 SNAs was examined. Oligonucleotides with increasing HEG spacer lengths were prepared and formulated into self-assembling SNAs. Primary human keratinocytes were plated in 96 well plates. The following day, the cells were treated with 50 ng/mL human recombinant TNF for 4 hours prior to being transfected with Oligo ID 6080, 6081, 6082, 6092, 6083, 6093, 6094 or 6095 SNAs at oligonucleotide concentrations of 100, 10, 1, and 0.1 nM. The treatment was allowed to proceed overnight. The following day, the cells were washed, the mRNA collected, cDNA prepared, and the expressions of TNF and GAPDH were probed and the percent gene expression was calculated (FIG. 10).

TABLE 6

Oligonucleotide Sequences for Hollow SNA Investigation

| Oligo ID | Oligonucleotide Sequence (5' to 3') | SEQ ID NO. |
|---|---|---|
| 6080 | mUmGmGmGmAmGT*A*G*A*T*G*mAmGmGmUmAmC/iSp18//iSp18//iSp18//3CholTEG/ | 35 |
| 6081 | mUmGmGmGmAmGT*A*G*A*T*G*mAmGmGmUmAmC/iSp18//iSp18//3CholTEG/ | 36 |
| 6082 | mUmGmGmGmAmGT*A*G*A*T*G*mAmGmGmUmAmC/iSp18//3CholTEG/ | 37 |
| 6092 | mUmGmGmGmAmGT*A*G*A*T*G*mAmGmGmUmAmC/3CholTEG/ | 38 |
| 6083 | mAmUmGmGmAmGC*A*A*A*A*C*mCmCmGmCmAmG/iSp18//iSp18//3CholTEG/ | 39 |
| 6093 | mAmUmGmGmAmGC*A*A*A*A*C*mCmCmGmCmAmG/iSp18//iSp18//3CholTEG/ | 40 |
| 6094 | mAmUmGmGmAmGC*A*A*A*A*C*mCmCmGmCmAmG/iSp18//3CholTEG/ | 41 |
| 6095 | mAmUmGmGmAmGC*A*A*A*A*C*mCmCmGmCmAmG/3CholTEG/ | 42 |

"*" denotes a phosphorotioate bond,
"m" denotes an O'methylated base,
"/iSp18/" denotes a hexa(ethylene glycol) spacer,
"/3CholTEG/" denotes a 3 tri(ethylene glycol) bound to a cholesterol

Example 4: Testing Ex Vivo Activity in Human Psoriatic Skin

Oligonucleotides were synthesized with a Mermade 48 (Bioautomation) using standard solid phase phosphoramidite methodology. Bases and reagents were purchased from Glen Research and Chemgenes. All oligonucleotides were purified by reverse-phase high performance liquid chromatography (HPLC) and molecular weights were measured using matrix-assisted laser desorption/ionization (MALDI) analysis. The synthesized oligonucleotides are listed in Table 7.

Liposomes were synthesized by extrusion of 1,2-dioleoyl-sn-glycero-3-phosphocholine (DOPC) hydrated in phosphate buffered saline solution (PBS) (137 mM NaCl, 10 M phosphate, 2.7 mM KCl, pH 7.4, hyclone) using 47 mm diameter polycarbonate membranes with 50 nm pores (Sterlitech). Liposome diameters were measured using dynamic light scattering using a Malvern Zetasizer Nano (Malvern Instruments). Lipid concentration was determined using a phospholipid assay kit (Sigma).

L-SNAs were synthesized by mixing oligonucleotides to liposomes in a 100:1 molar ratio, and incubating the mixture at room temperature for 4 hours. L-SNAs were isolated from unreacted materials and concentrated using tangential flow filtration (TFF) using a MiniKros Pilot i System (Spectrum Labs) with a 30 kD molecular weight cutoff modified polyethersulfone (mPES) hollow fiber filter module. Retentate containing L-SNAs were analyzed for lipid concentration using a phospholipid assay kit (Sigma). L-SNAs were diluted in 90% methanol to dissolve liposomes to release surface functionalized oligonucleotides whose concentration was measured using a Cary UV/vis spectrophotometer (Agilent). The average number of oligonucleotides conjugated to a nanoparticle was calculated by dividing the concentration of oligonucleotides by the concentration of liposomes. L-SNA diameters were measured using dynamic light scattering using a Malvern Zetasizer Nano (Malvern Instruments).

The gene regulatory effects of applying L-SNAs containing Oligo 4831.1 on human psoriatic ex vivo skin cultures was examined. Experimental groups are listed in Table 8.

Four 3 mm diameter skin biopsies were taken from psoriatic plaques of 5 different patients with mild to moderate plaque psoriasis. Each replicate was taken from a different patient for accurate representation and against a patient specific response. Explants were cultured in the following manner. Holes were punched into the center of Corning 12-well cell culture filter inserts. The dermal (bottom) portion of the explants were pushed into the hole in the filter such that the biopsy was embedded in the filter. The epidermis was exposed in the inner chamber, and the dermis was exposed in the outer chamber. These filters were immersed in 1 ml cell culture medium (DMEM, 1% FBS, 1.25 µg/mL amphotericin B, 50 µg/mL gentamicin, 0.1 U/mL penicillin/streptomycin) such that the dermis contacted the medium in the well and the epidermis was exposed to air. Cultures were treated in the following manner: 2 µL of each compound was applied in PBS to the top (stratum corneum) of each biopsy using a pipette. Biopsies were incubated for 16 hours at 37° C.

Figure 11:
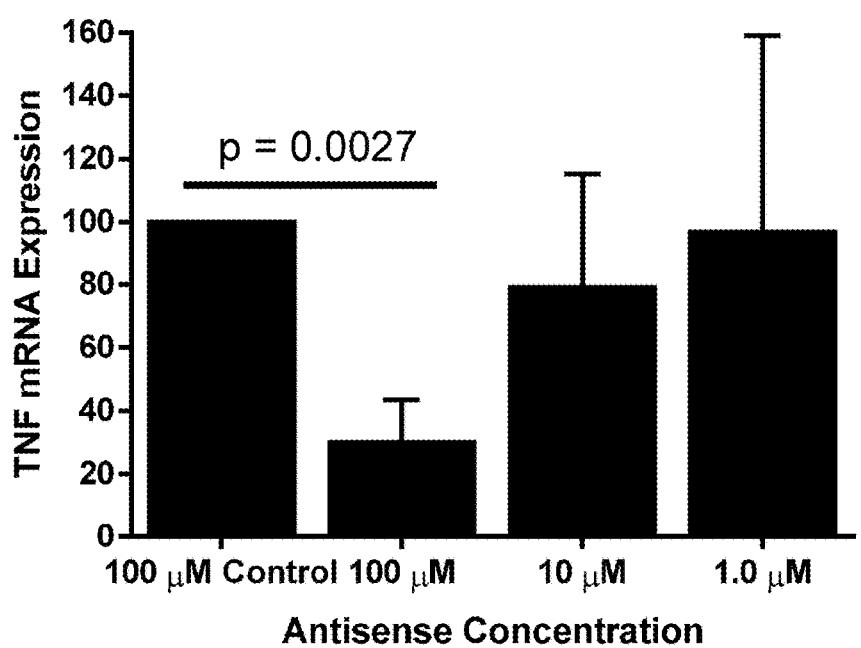
FIG. 11 is a bar graph showing L-SNAs knock down TNF in psoriatic ex vivo explants.
Figure 12A:
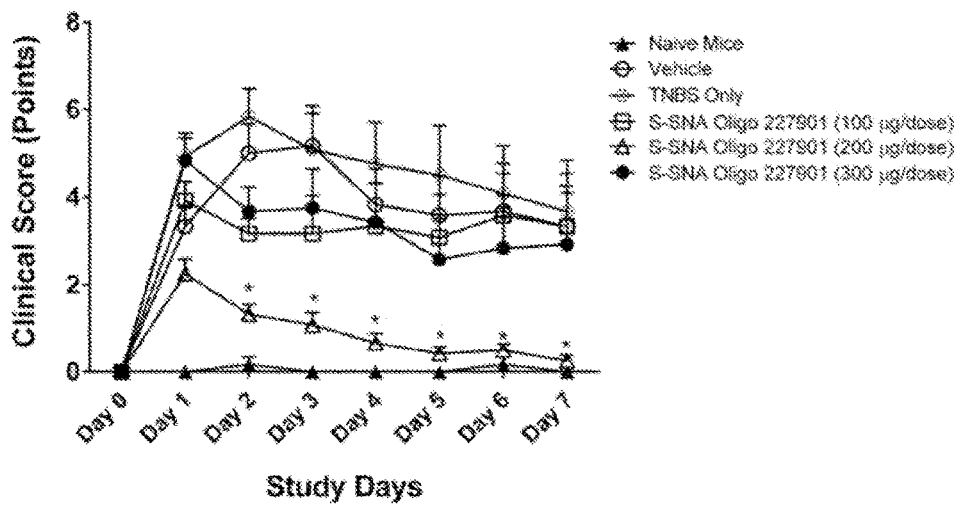
FIGS. 12A-12D show the reduced clinical and gross pathology scores for S-SNA (self-assembled SNA) and L-SNA (liposomal SNA) forms of TNF antisense oligonucleotides in Inflammatory Bowel Disease (IBD) containing mice.
Figure 12B:
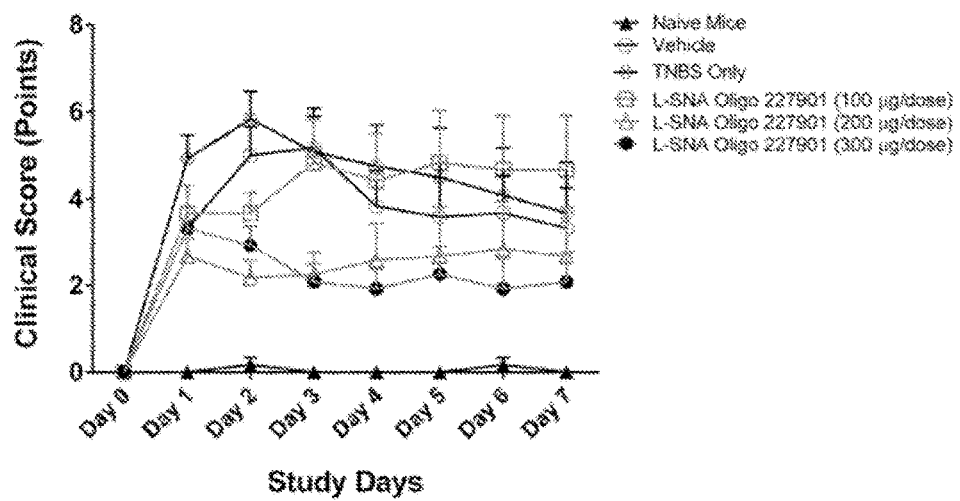
Figure 12C:
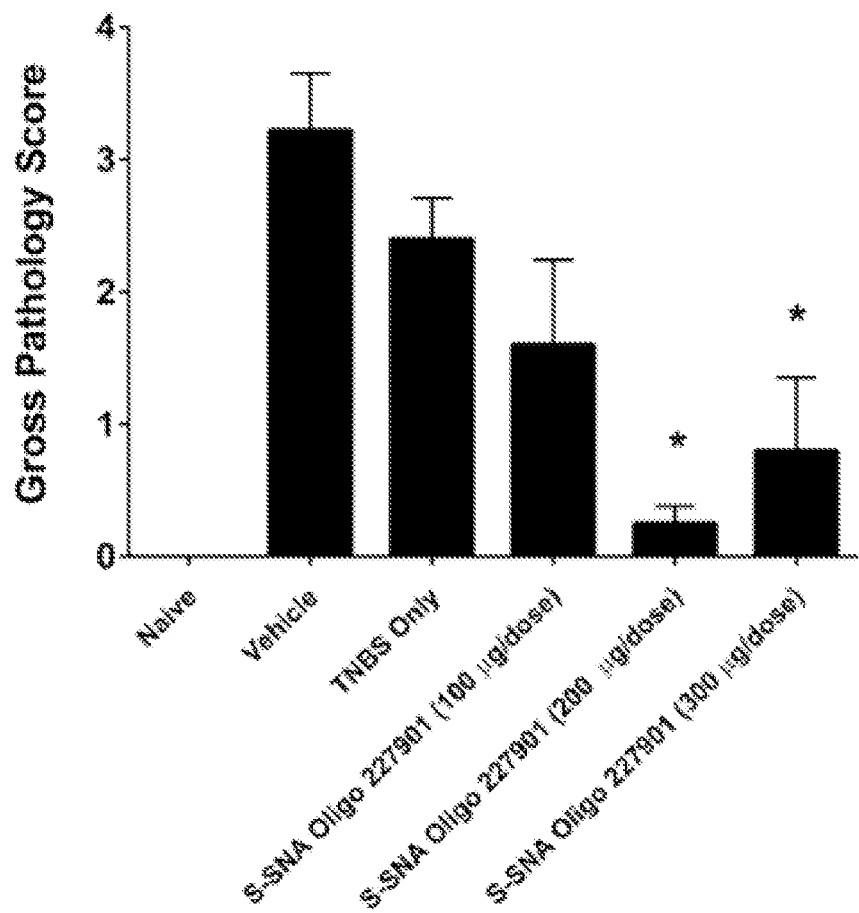
Figure 12D:
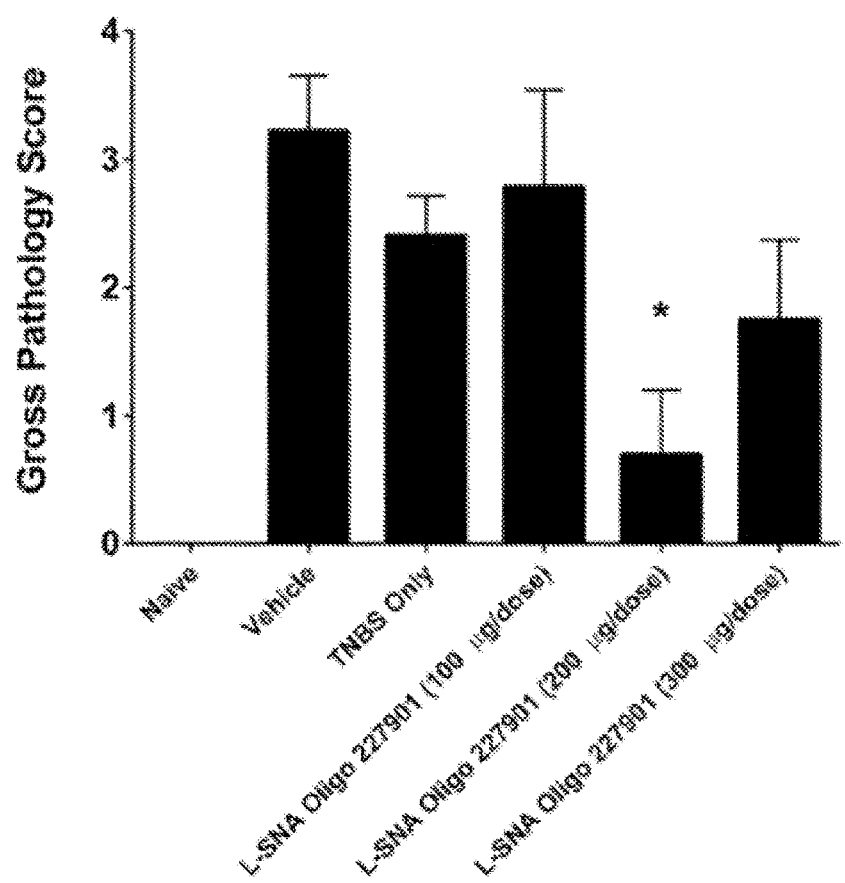

Samples were homogenized immediately in 300 µL of RLT buffer (Qiagen) in 2 mL screw cap vials filled with 3 mm diameter zirconia ball bearings using a ball bearing homogenizer. Homogenized samples were immediately flash frozen and stored at −80° C. Lysates were processed using a Qiagen 96 well RNeasy plate extraction kit. RTPCR was performed on a Lightcycler (Roche Diagnostics) using probes and primers against hTNF and hGAPDH (Roche Diagnostics) and TNF gene expression was measured (FIG. 11).

TABLE 7

Oligonucleotide sequences

| Name | Oligo ID | Sequence (5' to 3') | SEQ ID NO. |
|---|---|---|---|
| Control | Oligo4832.1 | mGmUmU mUmCmA C*C*A*C*C*C* mAmAmUmUmCmC/iSp18//iSp18//3Toco/ | 43 |
| TNF Antisense | Oligo4831.1 | mUmGmGmGmAmG T*A*G*A*C*A* mAmGmGmUmAmC/iSp18//iSp18//3Toco/ | 44 |

Special bases used in the oligonucleotides are as follows: mX = 2' O-methyl RNA, /iSp18/ = Spacer18 phosphoramidite, /3Toco/ = 3' tocopherol, * = phosphorothioate

TABLE 8

Ex Vivo psoriatic skin groups and treatments

| Groups | Tissue Source | Oligo | Target | Type | Concentration |
|---|---|---|---|---|---|
| 1 | Patient A | Oligo 4832.1 | Control | L-SNA | 100 µM |
| 2 | Patient A | Oligo 4831.1 | TNF | L-SNA | 100 µM |

TABLE 8-continued

Ex Vivo psoriatic skin groups and treatments

| Groups | Tissue Source | Oligo | Target | Type | Concentration |
|---|---|---|---|---|---|
| 3 | Patient A | Oligo 4831.1 | TNF | L-SNA | 10 µM |
| 4 | Patient A | Oligo 4831.1 | TNF | L-SNA | 1 µM |
| 5 | Patient B | Oligo 4832.1 | Control | L-SNA | 100 µM |
| 6 | Patient B | Oligo 4831.1 | TNF | L-SNA | 100 µM |
| 7 | Patient B | Oligo 4831.1 | TNF | L-SNA | 10 µM |
| 8 | Patient B | Oligo 4831.1 | TNF | L-SNA | 1 µM |

Example 5: Testing the Efficacy of Anti-TNF SNAs and L-SNAs in TNBS-Induced Inflammatory Bowel Disease (IBD) Mouse Model The effect of Oligo 227901 (Table 9) was assessed in a TNBS-induced IBD mice model. Oligo 227901 was synthesized with cholesterol at its 3'end (reagents from ChemGenes). In example 6, we show the formation of self-assembled SNA structure of this oligonucleotide using Cryo-EM. In addition, an L-SNA form of Oligo 227901 has been prepared by adding oligonucleotide to 50 nm DOPC liposome solutions. S—SNAs and L-SNAs were brought to pH 9.5 in bicarbonate solution for using in animals.

Studies of TNBS-induced colitis were performed in 6-7 weeks old Balb/c mice. For the induction of colitis, 10 mg of TNBS dissolved in 80% ethanol was administered per animal intra rectally on study day 0. Controls mice consisted of mice treated with vehicle only and untreated naïve mice.

To examine therapeutic effect of S-SNAs and L-SNA of Oligo 227901 on TNBS-induced colitis study, mice were treated with compounds on day 1, 2, 3 and 4 (total 4 doses) from 100 µg/dose/mice to 300 µg/dose/mice by oral gavage after the induction of colitis. The mice were monitored daily up to 7 days for clinical score observations, and euthanized on day 7 for analysis of gross pathology.

Clinical scores for the control mice and treated mice were assigned by considering the parameters: body weight, stool consistency and bleeding per rectum and any abnormalities observed in fur coat and abdomen.

Gross pathology scores were assigned to the control and treated mice on the last day of study from the colons removed from the animals after euthanization. Gross pathology scores from 0 to 5 were assigned based on the observations: No abnormalities detected (score 0); edema and redness in one location (score 1); edema and redness in more than one location (score 2); One ulcer (score 3); more than one ulcer or severe ulcer (score 4); and edema and redness in more than one location, and one or more than one ulcer (score 5).

The results of the study are represented in FIG. 12. The statistical significance of the groups was calculated using one way ANOVA followed by Tukey's post-hoc test. An increase in clinical score and gross pathology score in the TNBS-only group suggests that rectal administration of TNBS established colitis disease in all of the groups except naïve mice. A significant reduction in the mean clinical score compared to the relevant vehicle group was observed for the group treated with S-SNA form of Oligo 227901 at an amount 200 µg/dose of total 4 doses from day 1 to day 4 after colitis induction with TNBS on day 0. Animals that were treated from day 1 until day 4 with four doses of S-SNA (200 µg/dose and 300 µg/dose) and L-SNA (200 µg/dose) showed significant reduction in gross pathology score compared to vehicle group. Overall, the results suggest that oral administration of S-SNA had a positive effect on disease symptoms reflecting lower clinical score, lower pathology score and higher animal survival rate.

TABLE 9

Oligonucleotide Sequence in Inflammatory Bowel Disease (IBD) Investigation

| Oligo ID | Oligo Name | Oligo Sequence (5' to 3') (m = methylated; * = phosphorothioate linkage) | SEQ ID NO. |
|---|---|---|---|
| 227901 | TNF568-chol | mUmGmGmGmAmGT*A*G*A*T*G*mAmGmGmUmAmC/iSp18//iSp18//chol/ | 45 |

Example 6: Cryo-TEM of Self-Assembling SNA

CryoTEM imaging was performed on a solution of Oligo 6307 Self-Assembling Spherical Nucleic Acids (S-SNAs) (Table 10). S-SNA were prepared in phosphate buffered saline solution (PBS) (137 mM NaCl, 10 M phosphate, 2.7 mM KCl, pH 7.4, Hyclone) using a 2.4 mM oligonucleotide solution. The sample was preserved in vitrified ice supported by holey carbon films on 400-mesh copper grids. Each sample was prepared by applying a 30 drop of sample suspension to a cleaned grid, blotting away with filter paper, and immediately proceeding with vitrification in liquid ethane. Grids were stored under liquid nitrogen until transferred to the electron microscope for imaging.

Electron microscopy was performed using an FEI Tecnai T12 electron microscope, operating at 120 keV equipped with an FEI Eagle 4K×4 k CCD camera. Vitreous ice grids were transferred into the electron microscope using a cryostage that maintains the grids at a temperature below −170° C. High magnification image was acquired at a nominal magnification of 110,000× (0.10 nm/pixel). Image was acquired at a nominal underfocus of ~5 μm to −3 μm and electron doses of 10 to 40 e-/A².

Figure 13:
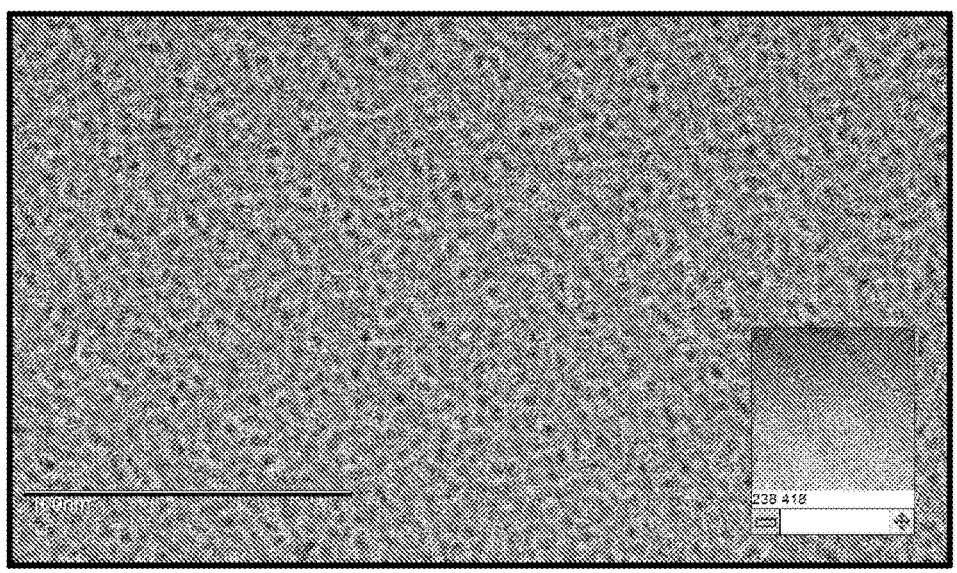
FIG. 13 shows a cryo-TEM of Oligo 6307 self-assembling SNA.
Figure 14A:
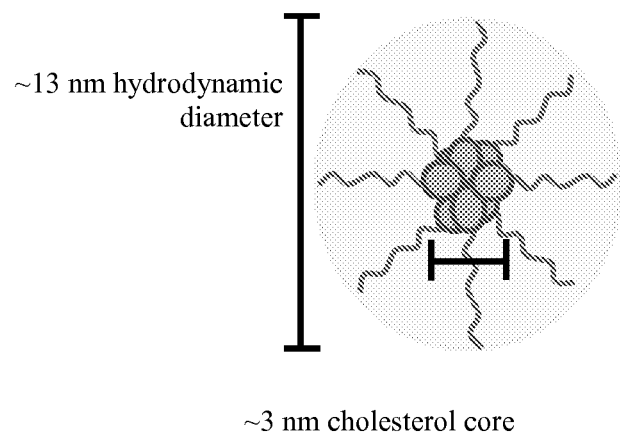
FIGS. 14A-14B depict a schematic representation of cryo-TEM of oligo 6307 self-assembling SNA. Schematic of individual (FIG. 14A) and collection of SNA (FIG. 14B) are shown.
Figure 14B:
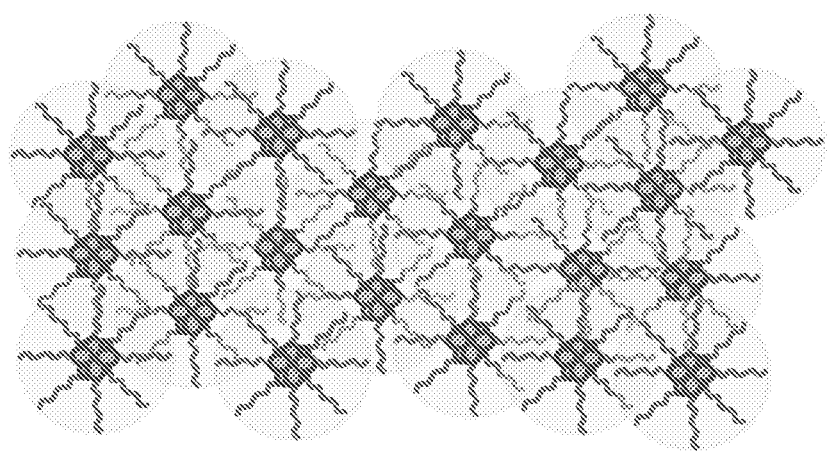

The sample is primarily composed of many small ~3 nm round particles throughout the field (FIG. 13). These round particles correspond to the diameter of a cluster of cholesterol molecules that make up hydrophobic core of the S-SNA particle. The small ~3 nm round particles are evenly spaced by 3 to 5 nm gaps which likely correspond to the oligonucleotide corona arrayed in a spherical orientation around the hydrophobic core (FIG. 14A). The oligonucleotide corona or shell defines the hydrodynamic radius of the S-SNA which is approximately 13 nm, resulting in the even spacing between the electron dense hydrophobic cores (FIG. 14B).

TABLE 10

Oligonucleotide Sequence

| Oligo ID | Sequence (5' to 3') | SEQ ID NO. |
|---|---|---|
| Oligo 6307 | mUmGmGmGmAmG T*A*G*A*C*A*mAmGmGmUmAmC/iSp18//iSp18//3Chol/ | 46 |

What is claimed is:

1. A compound comprising the structure depicted in FIG. 7, SEQ ID NO. 16, or salts thereof, of 18-19 nucleotides in length wherein the compound includes at least one phosphorothioate modification.

2. The compound of claim 1, wherein the compound is 18 nucleotides in length.

3. The compound of claim 1, formulated in a composition with a carrier.

4. The compound of claim 1, wherein the compound is a sodium salt.

Figure 8:
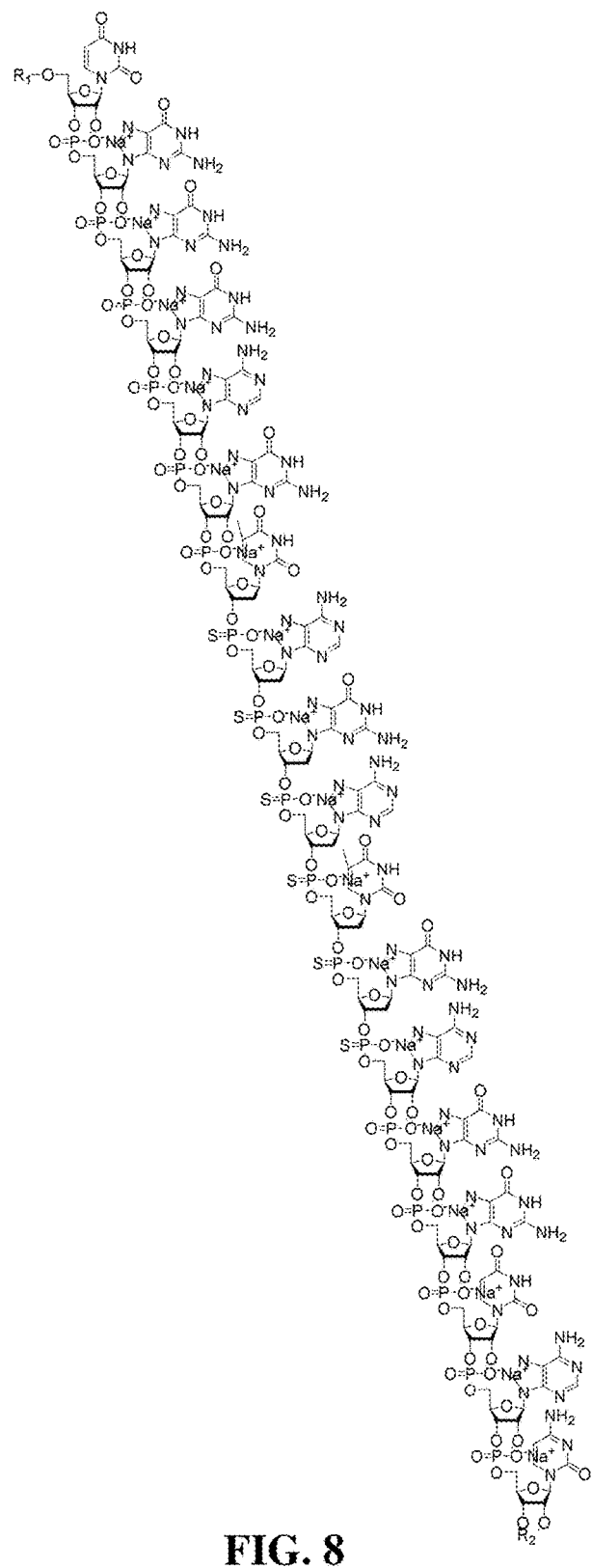
FIG. 8 is a structure of a salt form of a TNF antisense oligonucleotide, which corresponds to SEQ ID NO: 16.

5. The compound of claim 1, wherein the compound is the structure depicted in FIG. 8, SEQ ID NO.16.

6. The compound of claim 1, wherein the compound further comprises a molecular species at one of the ends.

7. The compound of claim 1, wherein the compound further comprises a molecular species at both ends.

8. The compound of claim 6, wherein the molecular species is selected from the group consisting of a spacer, a lipid, a sterol, cholesterol, stearyl, C16 alkyl chain, bile acids, cholic acid, taurocholic acid, deoxycholate, oleyl litocholic acid, oleoyl cholenic acid, glycolipids, phospholipids, sphingolipids, isoprenoids, such as steroids, vitamins, such as vitamin E, saturated fatty acids, unsaturated fatty acids, fatty acid esters, such as triglycerides, pyrenes, porphyrines, Texaphyrine, adamantane, acridines, biotin, coumarin, fluorescein, rhodamine, Texas-Red, digoxygenin, dimethoxytrityl, t-butyldimethylsilyl, t-butyldiphenylsilyl, cyanine dyes (e.g. Cy3 or Cy5), Hoechst 33258 dye, psoralen, and ibuprofen.

9. The compound of claim 6, wherein the molecular species is a selected from the group consisting of a lipophilic moiety; a folic acid radical; a steroid radical; a carbohydrate radical; a vitamin A radical; a vitamin E radical; or a vitamin K radical.

10. The compound of claim 6, wherein the molecular species is connected directly to the compound through a linkage selected from the group consisting of phosphodiester, phosphorothioate, methylphosphonate, and amide linkages.

11. The compound of claim 6, wherein the molecular species is connected indirectly to the compound through a linker.

12. The compound of claim 11, wherein the linker is a non-nucleotidic linker selected from the group consisting of abasic residues (dSpacer), oligoethyleneglycol, such as triethyleneglycol (spacer 9) or hexaethylenegylcol (spacer 18), and alkane-diol, such as butanediol.

13. An oligonucleotide comprising mUmGmGmGmAmGT*A*G*A*T*G*mAmGmGmUm AmC (SEQ ID NO. 16), wherein the oligonucleotide is 18 nucleotides in length, wherein m is a 2'O methyl, and wherein * is a phosphorothioate modification.

14. The oligonucleotide of claim 13, wherein the oligonucleotide is formulated in a composition with a carrier.

15. The oligonucleotide of claim 14, wherein the carrier is a lipid based carrier.

16. The oligonucleotide of claim 14, wherein the carrier is a nanoparticle.

17. The oligonucleotide of claim 13, wherein the oligonucleotide further comprises a molecular species at the 3' or 5' end.

18. The oligonucleotide of claim 13, wherein the oligonucleotide further comprises a molecular species at both the 3' and 5' ends.

19. The oligonucleotide of claim 17, wherein the molecular species is selected from the group consisting of a spacer, a lipid, a sterol, cholesterol, stearyl, C16 alkyl chain, bile acids, cholic acid, taurocholic acid, deoxycholate, oleyl litocholic acid, oleoyl cholenic acid, glycolipids, phospholipids, sphingolipids, isoprenoids, such as steroids, vitamins, such as vitamin E, saturated fatty acids, unsaturated fatty acids, fatty acid esters, such as triglycerides, pyrenes, porphyrines, Texaphyrine, adamantane, acridines, biotin, coumarin, fluorescein, rhodamine, Texas-Red, digoxygenin, dimethoxytrityl, t-butyldimethylsilyl, t-butyldiphenylsilyl, cyanine dyes (e.g. Cy3 or Cy5), Hoechst 33258 dye, psoralen, and ibuprofen.

20. The oligonucleotide of claim 17, wherein the molecular species is a selected from the group consisting of a lipophilic moiety; a folic acid radical; a steroid radical; a carbohydrate radical; a vitamin A radical; a vitamin E radical; or a vitamin K radical.

21. The oligonucleotide of claim 17, wherein the molecular species is connected directly to the compound through a linkage selected from the group consisting of phosphodiester, phosphorothioate, methylphosphonate, and amide linkages.

22. The oligonucleotide of claim 17, wherein the molecular species is connected indirectly to the compound through a linker.

23. The oligonucleotide of claim 22, wherein the linker is a non-nucleotidic linker selected from the group consisting of abasic residues (dSpacer), oligoethyleneglycol, such as triethyleneglycol (spacer 9) or hexaethylenegylcol (spacer 18), and alkane-diol, such as butanediol.

24. An oligonucleotide comprising 5' TGGGAGTAGAT-GAGGTAC 3' (SEQ ID NO. 4), wherein the oligonucleotide is 18-19 nucleotides in length, wherein 4-6 nucleotides at the 5' end and 4-6 nucleotides at the 3' end of the oligonucleotide include a 2'O methyl, and wherein 4-10 nucleotides have a phosphorothioate modification.

25. The oligonucleotide of claim 24, wherein the 6 nucleotides at the 5' end and 6 nucleotides at the 3' end of the oligonucleotide include a 2'O methyl.

26. The oligonucleotide of claim 24, wherein 6, 7, or 8 nucleotides have a phosphorothioate modification, and wherein the phosphorothioate modified nucleotides are in a central region of the oligonucleotide.

27. A stable self-assembling nanostructure, comprising an antisense oligonucleotide of 18-19 nucleotides in length comprising TGGGAGTAGATGAGGTAC (SEQ ID NO. 4), wherein the antisense oligonucleotide is associated with a core.

28. The nanostructure of claim 27, wherein the antisense oligonucleotide is indirectly linked to the core through a linker.

29. The nanostructure of claim 27, wherein the antisense oligonucleotide is indirectly linked to the core through more than one linker.

30. The nanostructure of claim 27, wherein the core is a hollow core.

31. A stable self-assembling nanostructure, comprising an antisense oligonucleotide of 18-19 nucleotides in length comprising TGGGAGTAGATGAGGTAC (SEQ ID NO. 4), wherein a hydrophobic group at the 3' or 5' terminus self-associates to form the core of the nanostructure in water or other suitable solvents.

32. The nanostructure of claim 30, wherein the hollow core is a liposome.

33. The oligonucleotide of claim 24, wherein the internucleotide linkage associated with the seventh, eighth, ninth, tenth, eleventh, and twelfth nucleotide from the 5' end of the oligonucleotide is phosphorothioate modified.

34. The oligonucleotide of claim 24, wherein each nucleotide has either a 2'O methyl modification or phosphorothioate internucleotide linkage.

35. The nanostructure of claim 27, wherein the antisense oligonucleotide is 18 nucleotides in length.

36. The nanostructure of claim 27, wherein the antisense oligonucleotide has 2'O methyl modifications.

37. The nanostructure of claim 27, wherein the antisense oligonucleotide has 17 internucleotide linkages and wherein the 6 central internucleotide linkages are phosphorothioate.

38. The nanostructure of claim 27, wherein the antisense oligonucleotide is linked to the exterior of the core.

39. The nanostructure of claim 27, wherein the nanostructure includes 2-1,000 copies of the antisense oligonucleotide.

40. The nanostructure of claim 27, wherein the antisense oligonucleotide is positioned laterally on the surface of the nanostructure.

41. The nanostructure of claim 27, wherein the core is a liposomal core.

42. The stable self-assembling nanostructure of claim 31, wherein the oligonucleotide is at concentrations above 5 µM in DNase and RNase free water or other suitable solvents.

* * * * *